US011421021B2

(12) United States Patent
Kort et al.

(10) Patent No.: US 11,421,021 B2
(45) Date of Patent: Aug. 23, 2022

(54) IMMUNOGENIC COMPOSITIONS COMPRISING *STAPHYLOCOCCUS AUREUS* LEUKOCIDIN LUKA AND LUKB DERIVED POLYPEPTIDES

(71) Applicant: INTEGRATED BIOTHERAPEUTIC VACCINES, INC., Rockville, MD (US)

(72) Inventors: Thomas Kort, Rockville, MD (US); Nils Williston, Rockville, MD (US); Shweta Kailasan, Rockville, MD (US); Hatice Karauzum, Rockville, MD (US); Rajan P. Adhikari, Rockville, MD (US); Mohammad Javad Aman, Rockville, MD (US)

(73) Assignee: INTEGRATED BIOTHERAPEUTIC VACCINES, INC., Rockville, MD (US)

( * ) Notice: Subject to any disclaimer, the term of this patent is extended or adjusted under 35 U.S.C. 154(b) by 0 days.

(21) Appl. No.: 16/621,444

(22) PCT Filed: Jun. 13, 2018

(86) PCT No.: PCT/US2018/037376
§ 371 (c)(1),
(2) Date: Dec. 11, 2019

(87) PCT Pub. No.: WO2018/232014
PCT Pub. Date: Dec. 20, 2018

(65) Prior Publication Data
US 2020/0317759 A1    Oct. 8, 2020

Related U.S. Application Data

(60) Provisional application No. 62/518,641, filed on Jun. 13, 2017.

(51) Int. Cl.
C07K 16/12      (2006.01)
A61K 39/085     (2006.01)
A61K 39/00      (2006.01)

(52) U.S. Cl.
CPC ........ *C07K 16/1271* (2013.01); *A61K 39/085* (2013.01); *A61K 2039/575* (2013.01); *C07K 2317/76* (2013.01)

(58) Field of Classification Search
CPC ............ C07K 2317/76; C07K 16/1271; C07K 14/31; A61K 38/00; A61K 39/085; A61K 2039/575
See application file for complete search history.

(56) References Cited

U.S. PATENT DOCUMENTS 6,942,868 B2   9/2005   Edwards et al.
8,431,687 B2   4/2013   Torres et al.
(Continued)

FOREIGN PATENT DOCUMENTS

WO    2014187746 A2    11/2014
WO    2016197071 A1    12/2016

OTHER PUBLICATIONS

Badarau et al., "Structure-Function Analysis of Heterodimer Formation, Oligomerization, and Receptor Binding of the *Staphylococcus aureus* Bi-component Toxin LukGH"The Journal of Biological Chemistry. Jan. 2, 2015, Epub Nov. 14, 2014, vol. 290, No. 1, pp. 142-156. (Year: 2014).*

(Continued)

*Primary Examiner* — Jana A Hines
(74) *Attorney, Agent, or Firm* — Thompson Coburn LLP; William A. Holtz

(57) ABSTRACT

The present disclosure provides immunogenic compositions useful in prevention and treatment of *Staphylococcus aureus* infection. In particular, the disclosure provides methods of (Continued)

Figure 1:
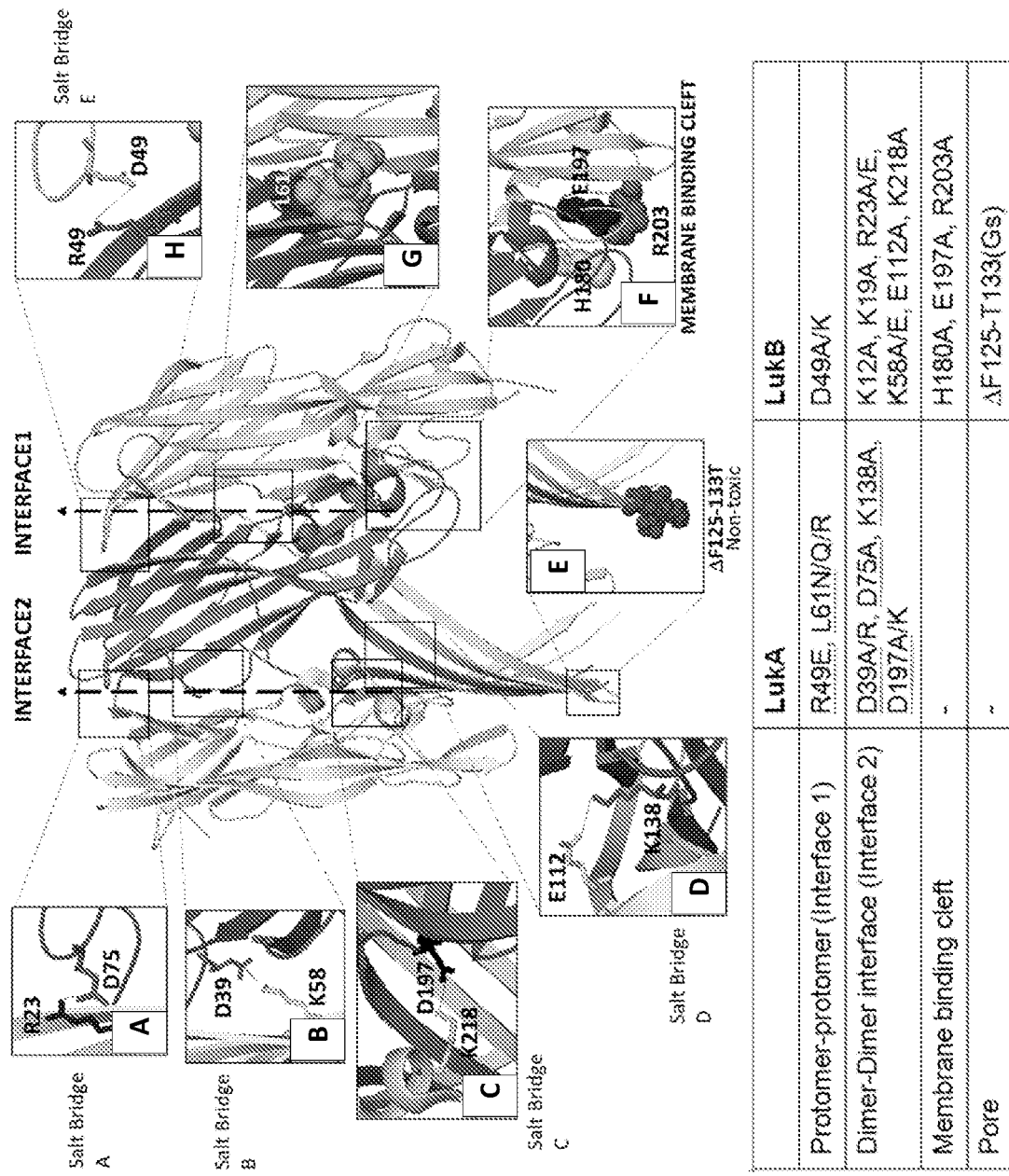

inducing an immune response against a LukAB-expressing *S. aureus*, methods of preventing or treating *S. aureus* infections, and composition for preventing or treating *S. aureus* infections.

21 Claims, 27 Drawing Sheets

Specification includes a Sequence Listing.

(56) References Cited

U.S. PATENT DOCUMENTS

| | | |
|---|---|---|
| 2005/0008633 A1 | 1/2005 | Vanbever et al. |
| 2011/0274693 A1* | 11/2011 | Torres et al. ........... A61P 29/00 424/139.1 |
| 2015/0086539 A1 | 3/2015 | Nagy et al. |
| 2016/0340415 A1 | 11/2016 | Nagy et al. |

OTHER PUBLICATIONS

Badarau et al., (J of Biol Chem vol. 290, Issue 1, Jan. 2, 2015, pp. 142-156) (Year: 2015).*

Alonzo et al., "*Staphylococcus aureus* Leukocidin ED Contributes to Systemic Infection by Targeting Neutrophils and Promoting Bacterial Growth in vivo", Mol Microbial, 2012, pp. 423-435, Vo. 83, Issue 2.

Badarau et al., "Context Matters: The Importance of Dimerization-Induced Conformation of the LukGH Leukocidin of *Staphylococcus aureus* for the Generation of Neutralizing Antibodies", MAbs, Jul. 28, 2016, pp. 1347-1360, vol. 8, No. 7.

Badarau et al., "Structure and Function of the Two-Component Cytotoxins of *Staphylococcus aureus*—Learning for Designing Novel Therapeutics", Advances in Experimental Medicine and Biology—Protein Reviews, 2017, pp. 15-35, vol. 966.

Badarau et al., "Structure-Function Analysis of Heterodimer Formation, Oligomerization, and Receptor Binding of the *Staphylococcusaureus* Bi-Component Toxin LukGH," Journal of Biological Chemistry, Jan. 2015, pp. 142-156, vol. 290, No. 1.

Bubeck-Wardenburg et al., "Surface Proteins and Exotoxins Are Required for the Pathogenesis of *Staphylococcus aureus* Pneumonia", Infection and Immunity, 2007, pp. 1040-1044, vol. 75, Issue 2.

Coler et al., "A Synthetic Adjuvant to Enhance and Expand Immune Responses to Influenza Vaccines", PLoS One, Oct. 2010, 11 pages, vol. 5, Issue 10, e13677.

Coler et al., "Development and Characterization of Synthetic Glucopyranosyl Lipid Adjuvant System as a Vaccine Adjuvant", PLoS One, Jan. 2011, 12 pages, vol. 6, Issue 1, e16333.

Dumont et al., "Identification of a Crucial Residue Required for *Staphylococcus aureus* LukAB Cytotoxicity and Receptor Recognition", Infection and Immunity, Mar. 2014, pp. 1268-1276, vol. 82, Issue 3.

Enkhbaatar et al., "Novel Ovine Model of Methicillin-Resistant *Staphylococcus aureus*-Induced Pneumonia and Sepsis," Shock, 2008, pp. 642-649, vol. 25, Issue 5.

Ferreras et al., "The Interaction of *Staphylococcus aureus* bi-component g-hemolysins and leucocidins with Cells and Lipid Membranes", Biochim Biophys Acta 1414, 1998, pp. 108-126.

Guillet et al., "Crystal Structure of Leucotoxin S Component", The Journal of Biological Chemistry, 2004, pp. 41028-41037, vol. 279, Issue 39.

International Search Report and Written Opinion for PCT/US2018/037376 dated Nov. 16, 2018.

Jursch et al., "Histidine Residues Near the N Terminus of Staphylococcal Alpha-Toxin as Reporters of Regions That Are Critical for Oligomerization and Pore Formation", Infection and Immunity, Jun. 1994, pp. 2249-2256, vol. 62, Issue 6.

Kaneko et al., "Bacterial Two-component and Hetero-heptameric Pore-forming Cytolytic Toxins: Structures, Pore-forming Mechanism, and Organization of the Genes", Bioscience, Biotechnology, and Biochemistry, 2004, pp. 981-1003, vol. 68, Issue 5.

Kephart et al., "Comparison of the Investigational drug, LY146032, with vancomycin in experimental pneumonia due to methicillin-resistant *Staphylococcus aureus*", J Antimicrob Chemother., 1988, pp. 33-39, vol. 21.

Malachowa et al., "Global Changes in *Staphylococcus aureus* Gene Expression in Human Blood", PLoS One, Apr. 2011, 13 pages, vol. 6, Issue 4, e18617.

McElroy et al., "Alpha-Toxin Damages the Air-Blood Barrier of the Lung in a Rat Model of *Staphylococcus aureus*-Induced Pneumonia", Infection and Immunity, Oct. 1999, pp. 5541-5544, vol. 67, Issue 10.

Miles et al., "Properties of Bacillus cereus hemolysin II: A heptameric transmembrane pore", Protein Science, 2002, pp. 894-902, vol. 11, Issue 4.

Mullen et al., "Phase 1 Trial of MAM1-C1/Alhydrogel plus CPG 7909: An Asexual Blood-Stage Vaccine for Plasmodium falciparum Malaria", PLoS One, Aug. 2008, 13 pages, vol. 3, Issue 8, e2940.

Pedelacq et al., "Crystal structure of the F component of the Panton-Valentine leucocidin", Internalational Journal of Medical Microbioly, Oct. 2000. 290(4-5): p. 395-401.

Prevost et al., "Panton-Valentine Leucocidin and Gamma-Hemolysin from *Staphylococcus aureus* ATCC 49775 Are Encoded by Distinct Genetic Loci and Have Different Biological Activities", Infection and Immunity, Oct. 1995, pp. 4121-4129, vol. 63, Issue 10.

Reyes-Robles et al., "Exploiting Dominant-Negative Toxins to Combat *Staphylococcus aureus* Pathogenesis", EMBO Reports, Mar. 2016, pp. 428-440, vol. 17, No. 3.

Thomsen et al., "Children with Invasive *Staphylococcus aureus* Disease Exhibit a Potently Neutralizing Antibody Response to the Cytotoxin LukAB", Infection and Immunity, Mar. 2014, pp. 1234-1242, vol. 82, Issue 3.

Ventura et al., "Identification of a Novel *Staphylococcus aureus* Two-Component Leukotoxin Using Cell Surface Proteomics", PLoS One, 2010, 11 pages, vol. 5, Issue 7, e11634.

Verghese et al., "LY146032 in a Hamster Model of *Staphylococcus aureus* Pneumonia—Effect on in vivo Clearance and Mortality and in vitro Opsonophagocytic Killing", Chemotherapy, 1988, pp. 497-503, vol. 34.

Yang et al., "Overcoming Immunity to a Viral Vaccine by DNA Priming before Vector Boosting," J Virol., 2003, pp. 799-803, vol. 77, Issue 1.

Kailasan et al., "Rational Design of Toxoid Vaccine Candidates for *Staphylococcus aureus* Leukocidin AB (LukAB)", Toxins, 2019, pp. 1-21, vol. 11, No. 6.

* cited by examiner

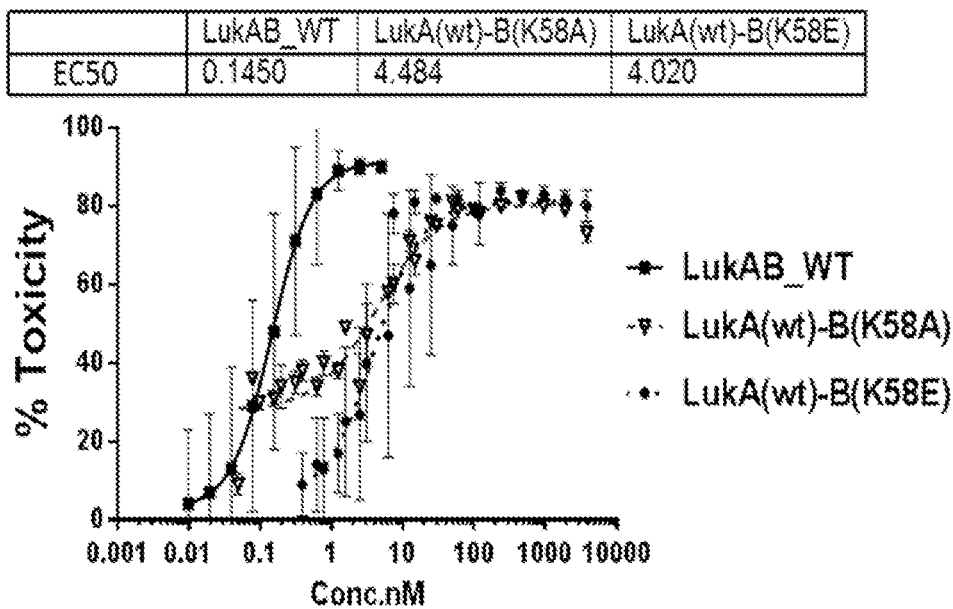
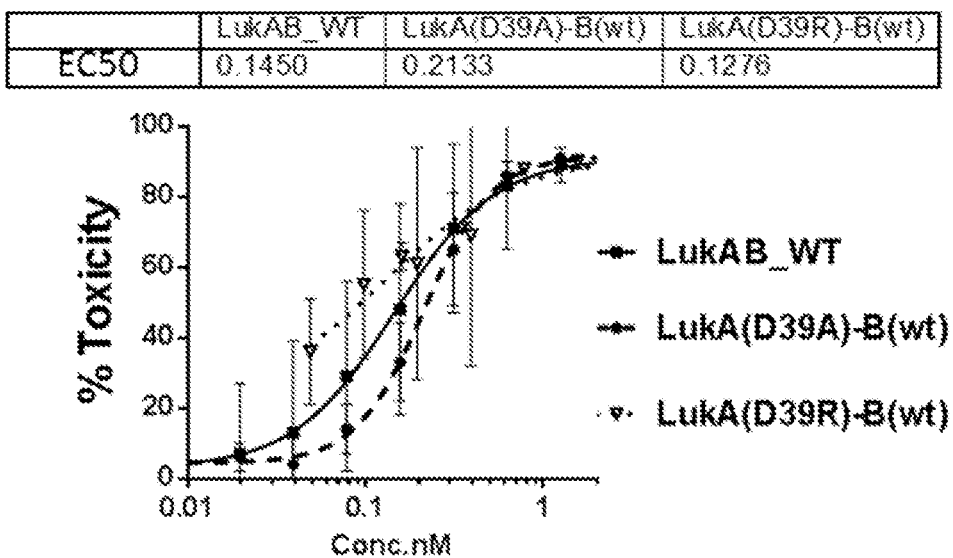
Figure 7A, B

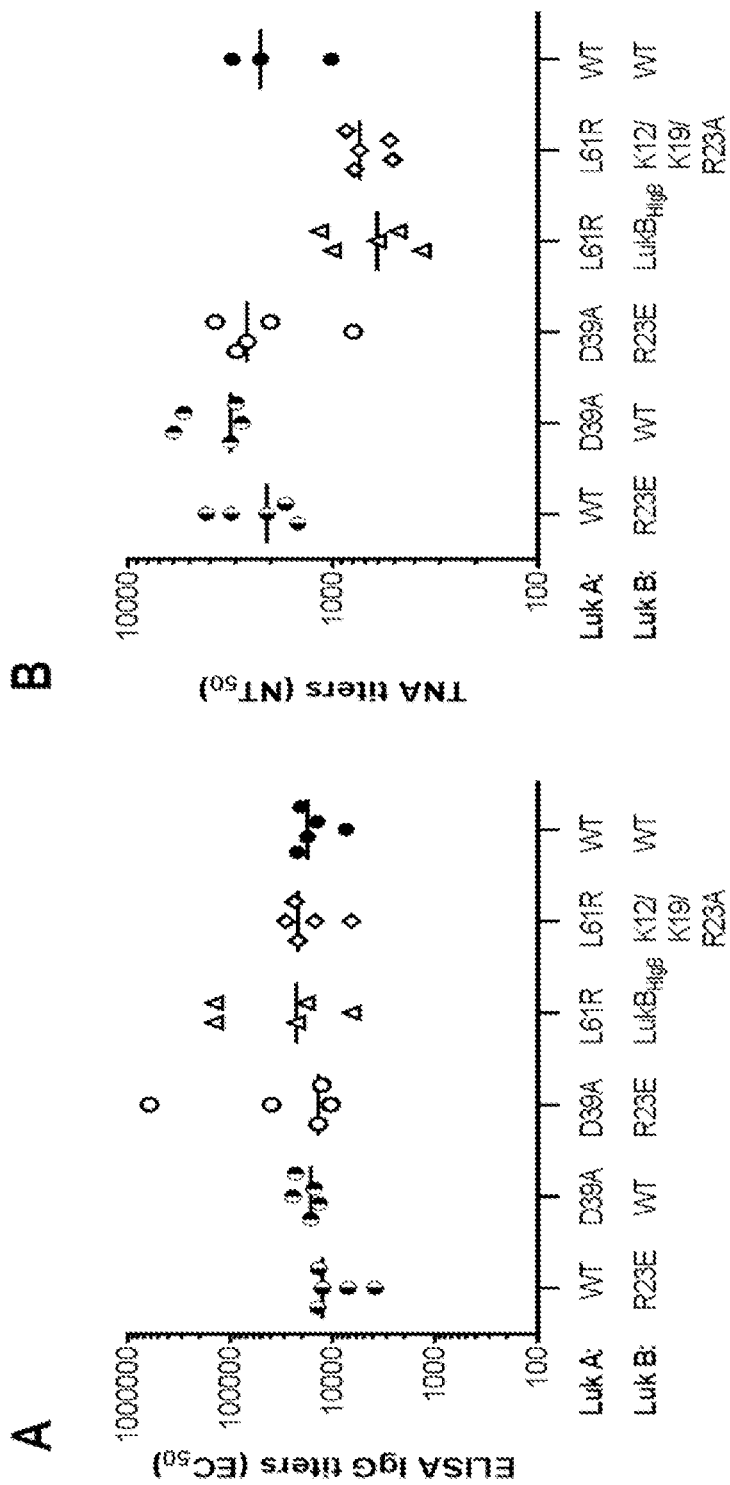
Figure 11A, B

IMMUNOGENIC COMPOSITIONS COMPRISING *STAPHYLOCOCCUS AUREUS* LEUKOCIDIN LUKA AND LUKB DERIVED POLYPEPTIDES

CROSS-REFERENCE TO RELATED APPLICATIONS

This application is a U.S. National Phase application of PCT/US2018/037376, filed on Jun. 13, 2018, which claims the benefit of U.S. Provisional Application No. 62/518,641, filed on Jun 13, 2017, both of which are incorporated herein by reference in their entireties.

GOVERNMENT RIGHTS

This invention was made with Government support under R01AI111205 awarded by the National Institutes of Health. The Government has certain rights in the invention.

BACKGROUND

This disclosure relates to the treatment and prevention of *Staphylococcus aureus* (*S. aureus*) infection. In particular, the disclosure provides compositions and methods for preventing *S. aureus* infection and treating a disease caused by a leukocidin, e.g., LukAB, LukED, Panton-Valentine leukocidin (PVL), or gamma-hemolysin expressing *S. aureus* infection.

*Staphylococcus aureus* (SA) is a gram positive human pathogen that is associated with or causes a wide range of pathologies ranging from skin and soft tissue infections to life-threatening systemic infections, e.g., skin infections such as pimples, impetigo, boils (furuncles), cellulitis folliculitis, carbuncles, scalded skin syndrome, and abscesses, to life-threatening deep infections such as pneumonia, sepsis, endocarditis, meningitis, post-operative wound infections, septicemia, and toxic shock syndrome (Nizet, V., J Allergy Clin Immunol, 2007. 120(1): p. 13-22; Kotzin, et al., Adv Immunol, 1993. 54: p. 99-166; Meyer et al., Int J Infect Dis, 2001. 5(3): p. 163-6; Schuberth et al., Vet Microbiol, 2001. 82(2): p. 187-99; and Silverstein et al., in Microbiology, Davis et al., eds. (Lippincott, Philadelphia, 1990), pp. 485-506).

Pneumonia is one of the most severe and prominent complications of *S. aureus* infection leading with 50,000 cases per year in the U.S. alone (Kuehnert, et al., Emerg. Infect. Dis. 11:868-872, 2005). *S. aureus* pneumonia has been traditionally ventilator associated but in recent years it has been recognized also as a major cause of community acquired pneumonia primarily in otherwise healthy children and young individuals.

The range of SA-associated pathologies reflects the diverse abilities of this microbe to escape the innate and adaptive immune response using multiple virulence factors including coagulase, capsular polysaccharides, adhesins, proteases, exoproteins that inactivate the complement system, pore-forming toxins, and other innate response mediators (Nizet, V., J Allergy Clin Immunol, 2007. 120(1): p. 13-22; Tristan et al., J Hosp Infect, 2007. 65 Suppl 2: p. 105-9). The rapid spread of methicillin resistant SA (MRSA) underscores the importance of developing vaccines for prevention or reduction of severity of MRSA infections. Most previous approaches for vaccine development have ignored the importance of including attenuated toxin components to disarm the immune evasion strategies of SA.

A significant increase in *S. aureus* isolates that exhibit resistance to most of the antibiotics currently available to treat infections has been observed in hospitals throughout the world. While MRSA strains were initially limited to health care settings, recent epidemics of community associated *S. aureus* (CA-MRSA) have been reported that cause severe disease in an otherwise healthy population. To date, five CA-MRSA clonal lineages are associated with these outbreaks: the Midwest clone (USA400, CC1), the European clone (CC80), the Southwest-Pacific Oceania clone (CC30), the Pacific clone (CC59), and the Pandemic clone (USA300, CC8). In addition to SCCmec IV, a characteristic feature of these major CA-MRSA lineages is that they have the lukPV operon encoding the Panton Valentine Leukocidin (PVL) (Diep, B.A. and M. Otto, Trends Microbiol, 2008. 16(8): p. 361-9), carried by the lysogenic phages φSLT, φPVL, φSA2MW and φSA2usa (Diep et al., Lancet, 2006. 367 (9512): p. 731-9; Kaneko et al., Gene, 1998. 215(1): p. 57-67; Narita et al., Gene, 2001. 268(1-2): p. 195-206). The development of penicillin to combat *S. aureus* was a major advance in infection control and treatment. Unfortunately, penicillin-resistant organisms quickly emerged and the need for new antibiotics was paramount. With the introduction of every new antibiotic, *S. aureus* has been able to counter with β-lactamases, altered penicillin-binding proteins, and mutated cell membrane proteins allowing the bacterium to persist. Consequently, methicillin-resistant *S. aureus* (MRSA) and multidrug resistant organisms have emerged and established major footholds in hospitals and nursing homes around the world. (Chambers, H. F., Clin Microbiol Rev., 1:173, 1988; and Mulligan, M. E., et al., Am J Med., 94:313, 1993). Today, almost half of the Staphylococcal strains causing nosocomial infections are resistant to all antibiotics except vancomycin and linezolid. Since many vancomycin intermediate resistant *S. aureus* (VISA) among MRSA, and a few vancomycin resistant *S. aureus*, have been reported in the literature, it appears to be only a matter of time before vancomycin will become ineffective as well. (Appelbaum P C., Clin Microbiol Infect., 12 Suppl 1:16-23, 2006).

Natural immunity to *S. aureus* infections remains poorly understood. Typically, healthy humans and animals exhibit a high degree of innate resistance to *S. aureus* infections. Protection is attributed to intact epithelial and mucosal barriers and normal cellular and humoral responses. Titers of antibodies to *S. aureus* components are elevated after severe infections (Ryding et al., J Med Microbiol, 43(5):328-334, 1995), however to date there is no serological evidence of a correlation between these acquired antibody titers and human immunity.

Pore forming toxins that are secreted by *S. aureus* are crucial to its immune evasion. These toxins can create a survival advantage for the bacteria by forming pores into the membrane of target cells, inducing cell death and weakening the host during the first stages of infection. Because of the limited treatment modalities for *S. aureus* infection, the emergence of methicillin-resistant *S. aureus* poses a tremendous public health threat. While the molecular basis of the disease remains unclear, community-associated MRSA infection is closely linked to leukotoxins. Leukotoxins consist of a family of five potent bi-component toxins: PVL, HlgAB, HlgCB, LukED, and LukAB. Leukotoxins kill human neutrophils, monocytes, and macrophage and some, primarily PVL, also induce a very strong inflammatory response that can have a pathophysiological impact. PVL is a key virulence factor of USA300 and several other pandemic clones. HlgAB and HlgCB promote the SA survival in blood, and Hlg−/− mutants show reduced mortality in mouse bacteremia models. Similarly, LukED and LukAB have been shown to play a critical role in SA virulence in various animal models. Recent reports indicate that LukAB and Hlg play a synergistic role in promoting macrophage dysfunction and facilitating SA biofilm formation in vivo.

LukAB (also referred to in the field as LukGH) has been shown to be highly expressed during the acute phase of *S. aureus* invasive disease in children (Thomsen et al., Infect Immun. 82(3):1234-42, 2014). LukAB is also highly expressed in USA300, the strain currently responsible for >60% cases of SA invasive disease in the United States.

Accordingly, there remains a need in the art for compositions and methods that can safely confer immunity to leukotoxin-expressing *S. aureus*.

SUMMARY

The present disclosure provides methods of inducing an immune response against a LukAB-expressing *S. aureus*, methods of preventing or treating LukAB-expressing *S. aureus* infections, and compositions for preventing or treating LukAB-expressing *S. aureus* infections. In certain aspects, the disclosure provides attenuated mutants of LukA and LukB as vaccines for *S. aureus* infections.

Provided for herein is an isolated mutant staphylococcal leukocidin subunit polypeptide comprising a wild-type staphylococcal LukA subunit, a wild-type staphylococcal LukB subunit, or a wild-type staphylococcal LukAB dimer, except for having one or more amino acid substitutions, deletions, or a combination thereof at conserved residues in the LukA subunit, the LukB subunit, or in the LukAB dimer. In certain aspects, the amino acid substitutions, deletions, or a combination thereof are at conserved residues in the LukAB protomer/protomer interface region, the LukAB dimer/dimer interface region, the LukB membrane-binding cleft region, the LukB pore forming region, or any combination thereof, such that the ability of the leukocidin subunits to form dimers, to oligomerize, to form pores on the surface of eukaryotic cells, or any combination thereof is disrupted. In certain aspects, this results in a reduction in the toxicity of the mutant leukocidin subunit or the mutant LukAB dimer relative to the corresponding wild-type leukocidin subunit or LukAB dimer. In certain aspects, the substitutions do not significantly reduce the immunogenicity of the mutant leukocidin subunit relative to the corresponding wild-type leukocidin subunit. In certain aspects, the mutant is immunogenic and elicits antibodies that can neutralize the action of the wild type toxin. In certain aspects, the mutant is immunogenic and elicits antibodies that can more effectively neutralize the action of the wild type toxin relative to the corresponding wild-type leukocidin subunit.

Provided for herein is a mutant staphylococcal leukocidin subunit comprising a mutation in the LukAB protomer/protomer interface region. In certain aspects, such mutation results in the formation of incomplete, larger leukocidin octamer rings, reduces or abolishes hemolytic activity of the toxin, or a combination thereof. In certain aspects, the mutation is at a LukA position corresponding to amino acid L61 of SEQ ID NO: 28, a LukB position corresponding to D49 of SEQ ID NO: 29, or a combination thereof. In certain aspects, the LukA position corresponding to L61 of SEQ ID NO: 28 is substituted with asparagine (N), glutamine (Q), or arginine (R). In certain aspects, such mutation can disrupt the hydrophobic pocket found within the LukAB protomer/protomer interface. In certain aspects, the LukB position corresponding to D49 of SEQ ID NO: 29 is substituted with alanine (A) or lysine (K). In certain aspects, substitution with alanine (A) or lysine (K) at the LukB position corresponding to D49 of SEQ ID NO: 29 can disrupt the salt bridge between LukB D49, corresponding to D49 of SEQ ID NO: 29, and LukA R49, corresponding to R49 of SEQ ID NO: 28.

Provided for herein is a mutant staphylococcal leukocidin subunit comprising a mutation in the LukAB dimer/dimer interface region. In certain aspects, such mutation can disrupt LukAB dimer formation, can disrupt LukAB oligomerization on the surface of a eukaryotic cell, can disrupt LukAB pore formation on the surface of a eukaryotic cell, or a combination thereof. In certain aspects, the mutation is at a LukA position corresponding to amino acid D39 of SEQ ID NO: 28, a LukA position corresponding to amino acid D75 of SEQ ID NO: 28, a LukA position corresponding to amino acid K138 of SEQ ID NO: 28, a LukA position corresponding to amino acid D197 of SEQ ID NO: 28, a LukB position corresponding to K12 of SEQ ID NO: 29, a LukB position corresponding to K19 of SEQ ID NO: 29, a LukB position corresponding to R23 of SEQ ID NO: 29, a LukB position corresponding to K58 of SEQ ID NO: 29, a LukB position corresponding to E112 of SEQ ID NO: 29, a LukB position corresponding to K218 of SEQ ID NO: 29, or any combination thereof. In certain aspects, the LukA position corresponding to D39 of SEQ ID NO: 28 is substituted with alanine (A) or arginine (R). In certain aspects, substitution with alanine (A) or arginine (R) at the LukA position corresponding to D39 of SEQ ID NO: 28 can disrupt the salt bridge between LukA D39, corresponding to D39 of SEQ ID NO: 28, and LukB K58, corresponding to K58 of SEQ ID NO: 29. In certain aspects, substitution with alanine (A) at the LukA position corresponding to D75 of SEQ ID NO: 28 can disrupt the salt bridge between LukA D75, corresponding to D75 of SEQ ID NO: 28, and LukB R23, corresponding to R23 of SEQ ID NO: 29. In certain aspects, the LukA position corresponding to K138 of SEQ ID NO: 28 is substituted with alanine (A). In certain aspects, substitution with alanine (A) at the LukA position corresponding to K138 of SEQ ID NO: 28 can disrupt the salt bridge between LukA K138, corresponding to K138 of SEQ ID NO: 28, and LukB E112, corresponding to E112 of SEQ ID NO: 29. In certain aspects, the LukA position corresponding to D197 of SEQ ID NO: 28 is substituted with alanine (A) or lysine (K). In certain aspects, substitution with alanine (A) or lysine (K) at the LukA position corresponding to D197 of SEQ ID NO: 28 can disrupt the salt bridge between LukA D197, corresponding to D197 of SEQ ID NO: 28, and LukB K218, corresponding to K218 of SEQ ID NO: 29. In certain aspects, the LukB position corresponding to K12 of SEQ ID NO: 29 is substituted with alanine (A). In certain aspects, the LukB position corresponding to K19 of SEQ ID NO: 29 is substituted with alanine (A). In certain aspects, the LukB position corresponding to R23 of SEQ ID NO: 29 is substituted with alanine (A) or glutamate (E). In certain aspects, substitution with alanine (A) or glutamate (E) at the LukB position corresponding to R23 of SEQ ID NO: 29 can disrupt the salt bridge between LukB R23, corresponding to R23 of SEQ ID NO: 29, and LukA D75, corresponding to D75 of SEQ ID NO: 28. In certain aspects, substitution with alanine (A) at the LukB position corresponding to K12, substitution with alanine (A) at the LukB position K19 of SEQ ID NO: 29, and substitution with alanine (A) or glutamate (E) at the LukB position corresponding to R23 of SEQ ID NO: 29 (LukB K12A/K19A/R23A or LukB K12A/K19A/R23E triple mutant), can disrupt at least the salt bridge between LukB R23, corresponding to R23 of SEQ ID NO: 29, and LukA D75, corresponding to D75 of SEQ ID NO: 28. In certain aspects, the LukB position corresponding to K58 of SEQ ID NO: 29 is substituted with alanine (A) or glutamate (E). In certain aspects, substitution with alanine (A) or glutamate (E) at the LukB position corresponding to K58 of SEQ ID NO: 29 can disrupt the salt bridge between LukB K58, corresponding to K58 of SEQ ID NO: 29, and LukA D39, corresponding to D39 of SEQ ID NO: 28. In certain aspects, the LukB position corresponding to E112 of SEQ ID NO: 29 is substituted with alanine (A). In certain aspects, substitution with alanine (A) at the LukB position corresponding to E112 of SEQ ID NO: 29 can disrupt the salt bridge between LukB E112, corresponding to E112 of SEQ ID NO: 29, and LukA K138, corresponding to K138 of SEQ ID NO: 28. In certain aspects, the LukB position corresponding to K218 of SEQ ID NO: 29 is substituted with alanine (A). In certain aspects, substitution with alanine (A) at the LukB position corresponding to K218 of SEQ ID NO: 29 can disrupt the salt bridge between LukB K218, corresponding to K218 of SEQ ID NO: 29, and LukA D197, corresponding to D197 of SEQ ID NO: 28.

Provided for herein is a mutant staphylococcal leukocidin subunit comprising a mutation in the LukB membrane-binding cleft region. In certain aspects, such mutation can disrupt interaction of LukB with the polar head groups of the lipid bilayer of a eukaryotic cell. In certain aspects, the mutation is at a LukB position corresponding to H180 of SEQ ID NO: 29, a LukB position corresponding to E197 of SEQ ID NO: 29, a LukB position corresponding to R203 of SEQ ID NO: 29, or any combination thereof. In certain aspects, the LukB position corresponding to H180 of SEQ ID NO: 29 is substituted with alanine (A). In certain aspects, the LukB position corresponding to E197 of SEQ ID NO: 29 is substituted with alanine (A). In certain aspects, the LukB position corresponding to R203 of SEQ ID NO: 29 is substituted with alanine (A).

Provided for herein is a mutant staphylococcal leukocidin subunit comprising a mutation in the LukB pore forming region. In certain aspects, such mutation can obstruct the cytoplasmic edge of the LukAB pore formed in a eukaryotic cell, thereby obstructing pore formation. In certain aspects, the mutation in the pore forming region comprises deletion of the amino acids corresponding to F125 to T133 of SEQ ID NO: 29, and in some aspects further comprises the insertion of one, two, three, four, or five glycine (G) residues after the amino acid corresponding to D124 of SEQ ID NO: 29.

In certain aspects, any of the aforementioned mutant staphylococcal leukocidin subunits is less toxic in a neutrophil toxicity assay compared to the corresponding wild-type leukocidin subunit.

In certain aspects, the wild-type LukA subunit comprises an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44.

In certain aspects, the wild-type LukB subunit comprises an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55.

Certain aspects provide for a polypeptide complex comprising a mutant LukA subunit described anywhere herein, a mutant LukB subunit described anywhere herein, a mutant LukAB dimer described anywhere herein, or any combination thereof. In certain aspects, the polypeptide complex further comprises an additional mutant staphylococcal leukocidin subunit polypeptide, wherein the additional mutant staphylococcal leukocidin subunit polypeptide is less toxic than the corresponding wild-type staphylococcal leukocidin subunit polypeptide. In certain aspects, the additional mutant staphylococcal leukocidin subunit polypeptide is a mutant LukA subunit, a mutant LukB subunit, a mutant LukS-PV subunit, a mutant LukF-PV subunit, a mutant LukE subunit, a mutant LukD subunit, a mutant Gamma hemolysin A, a mutant Gamma hemolysin B, a mutant Gamma hemolysin C, or any combination thereof. In certain aspects of the polypeptide complex of the disclosure, the mutant staphylococcal leukocidin subunit polypeptides are linked via peptide bonds or chemical conjugation.

In certain aspects, a mutant staphylococcal leukocidin subunit as described anywhere herein or a polypeptide complex as described anywhere herein further comprise a heterologous amino acid sequence. In certain aspects, the heterologous amino acid sequence encodes a peptide selected from a group consisting of a His-tag, a ubiquitin tag, a NusA tag, a chitin binding domain, a B-tag, a HSB-tag, green fluorescent protein (GFP), a calmodulin binding protein (CBP), a galactose-binding protein, a maltose binding protein (MBP), cellulose binding domains (CBD's), an avidin/streptavidin/Strep-tag, trpE, chloramphenicol acetyltransferase, lacZ(β-Galactosidase), a FLAG™ peptide, an S-tag, a T7-tag, a fragment of any of said heterologous peptides, and a combination of two or more of said heterologous peptides. In certain aspects, the heterologous amino acid sequence encodes an immunogen, a T-cell epitope, a B-cell epitope, a fragment of any of said heterologous peptides, and a combination of two or more of said heterologous peptides.

Certain aspects provide for a nucleic acid which encodes a mutant staphylococcal leukocidin subunit as described anywhere herein or a polypeptide complex as described anywhere herein. In certain aspects, the polynucleotide encoding a mutant subunit or a polypeptide complex further comprises a heterologous nucleic acid. In certain aspects, the heterologous nucleic acid comprises a promoter operably associated with the nucleic acid encoding the polypeptide.

Certain aspects provide for a vector comprising the aforementioned polynucleotide. In certain aspects, the vector is a plasmid. Further, certain aspects provide for a host cell comprising such vector. In certain aspects, the host cell is a bacterium, an insect cell, a mammalian cell, yeast or a plant cell. In certain aspects, the host cell is *Escherichia coli*.

Certain aspects provide for a method of producing a mutant staphylococcal leukocidin subunit polypeptide, comprising culturing a host cell disclosed anywhere herein, and recovering the polypeptide.

Certain aspects provide for a composition comprising a mutant staphylococcal leukocidin subunit as disclosed anywhere herein or a polypeptide complex as disclosed anywhere herein, and a carrier. In certain aspects, the composition further comprises an adjuvant. In certain aspects, the composition further comprises an additional staphylococcal antigen, and in certain aspects, the additional staphylococcal antigen is an alpha-hemolysin subunit polypeptide.

Certain aspects provide for a method of inducing a host immune response against a *Staphylococcus aureus* strain, comprising administering to a subject in need of the immune response an effective amount of any of the aforementioned compositions. In certain aspects, the immune response is an antibody response. In certain aspects, the immune response selected from the group consisting of an innate response, a humoral response, an antibody response a T cell response, and a combination of two or more of said immune responses. In certain aspects, the immune response results in at least 20%, at least 30%, at least 40%, at least 50%, at least 60%, at least 70% or at least 80% neutralization of a wild-type staphylococcal leukocidin toxin.

Certain aspects provide for a method of preventing or treating a Staphylococcal disease or infection in a subject comprising administering to a subject in need thereof any of the aforementioned compositions comprising a mutant subunit or a polypeptide complex. In certain aspects, the method further comprises administering a composition comprising an anti-leukocidin subunit antibody and/or an anti-a-hemolysin subunit antibody. In certain aspects, the Staphylococcal infection is a localized or systemic infection of skin, soft tissue, blood, or an organ, or is auto-immune in nature. In certain aspects, the Staphylococcal disease is a respiratory disease. In certain aspects, the respiratory disease is pneumonia. In certain aspects, the infection is a systemic infection of blood. In certain aspects, the subject is a vertebrate. In certain aspects, the vertebrate is a mammal. In certain aspects, the mammal is a human. In certain aspects, the composition is administered via intramuscular injection, intradermal injection, intraperitoneal injection, subcutaneous injection, intravenous injection, oral administration, mucosal administration, intranasal administration, or pulmonary administration.

Certain aspects provide for a method of producing a vaccine against *S. aureus* infection. The method comprises first isolating a mutant leukocidin subunit as disclosed anywhere herein or a polypeptide complex as disclosed anywhere herein and combining the mutant leukocidin subunit or polypeptide complex with an adjuvant. In certain aspects, the method further comprises combining the mutant leukocidin subunit or polypeptide complex with an additional staphylococcal antigen, and in certain aspects, the additional staphylococcal antigen is an alpha-hemolysin subunit polypeptide.

BRIEF DESCRIPTION OF THE DRAWINGS/FIGURES

FIG. 1 illustrates a portion of a LukAB octamer showing the protomer/protomer interface (Interface 1), the dimer/dimer interface (Interface 2), the membrane-binding cleft region, and the pore-forming region. Illustrative examples of substitutions of conserved amino acid residues in Interface 1, Interface 2, and the membrane-binding cleft region are shown. Deletion of a portion of the pore-forming region is also shown. Inset A shows dimer/dimer interface interactions between LukB R23 and LukA D75. Inset B shows dimer/dimer interface interactions between LukB K58 and LukA D39. Inset C shows dimer/dimer interface interactions between LukB K218 and LukA D197. Inset D shows dimer/dimer interface interactions between LukB E112 and LukA K138. Inset E shows deletion of LukB residues F125 to T133 in the LukB pore forming region. Inset F shows the LukB amino acid residues LukB H180, LukB E197, and LukB R203 in the LukB membrane-binding cleft region. Inset G shows the amino acid residue LukA L61 in the protomer/protomer interface region. Inset H shows protomer/protomer interface interactions between LukB D49 and LukA R49. The table at the bottom of FIG. 1 lists representative examples of mutations to LukA and/or LukB.

FIG. 2 is an alignment containing the amino acid sequence of a consensus majority LukA sequence (SEQ ID NO: 1), and the wild-type LukA polypeptides from thirteen (13) different strains of *S. aureus* to which it corresponds (SEQ ID NOs: 2-14). SEQ ID NO: 28 is a mature peptide version of SEQ ID NO: 1, i.e., absent the 27 amino acid signal sequence.

FIG. 3 is an alignment containing the amino acid sequence of a consensus majority LukB sequence (SEQ ID NO: 15), and the wild-type LukB polypeptides from twelve (12) different strains of *S. aureus* to which it corresponds (SEQ ID NOs: 16-27). SEQ ID NO: 29 is a mature peptide version of SEQ ID NO: 15, i.e., absent the 29 amino acid signal sequence.

FIG. 4 illustrates the toxicity of LukAB mutants containing mutations of LukA L61 within the Protomer-Protomer interaction interface as determined in HL60 cells differentiated into neutrophils. Data for mutants are an average of 2-8 experiments. Wild-type data are an average of 37 replicates in multiple experiments. Non-linear 4 parameter logistic (4PL) curve fit regression was used to fit the data.

FIG. 5 illustrates the toxicity of LukAB mutants containing mutations of LukB D49 involved in a salt bridge within the Protomer-Protomer interaction interface as determined in HL60 cells differentiated into neutrophils. Data are an average of duplicate experiments for the mutants. Non-linear 4 parameter logistic (4PL) curve fit regression was used to fit the data.

FIG. 6 illustrates the LukB mutations in Salt Bridge A. Toxicity of LukAB mutants containing mutations of LukB R23 or LukB K12/K19/R23 involved in a salt bridge within the Dimer-Dimer interaction interface was determined in HL60 cells differentiated into neutrophils. The number of replicates for wt LukB and mutants was 37 and 4, respectively. Non-linear 4 parameter logistic (4PL) curve fit regression was used to fit the data.

FIG. 7 illustrates the LukB mutations in Salt Bridge B. Toxicity of LukAB mutants containing mutations of LukB K58 (A) or LukA D39 (B) involved in a salt bridge within the Dimer-Dimer interaction interface was determined in HL60 cells differentiated into neutrophils. The number of replicates for wt LukAB, K58A, K58E, D39A, and D39R mutants was 37, 2, 6, 6, and 4, respectively. Non-linear 4 parameter logistic (4PL) curve fit regression was used to fit the data.

FIG. 8 illustrates the LukA mutation in Salt Bridge C. Toxicity of LukAB mutants containing alanine substitution of LukA (D197) involved in a salt bridge within the Dimer-Dimer interaction interface was determined in HL60 cells differentiated into neutrophils. The number of replicates for wt LukAB and mutant was 37 and 4, respectively. Non-linear 4 parameter logistic (4PL) curve fit regression was used to fit the data.

FIG. 9 illustrates the LukB mutation in Salt Bridge D. Toxicity of LukAB mutant containing alanine substitution of LukB (E112) involved in a salt bridge within the Dimer-Dimer interaction interface was determined in HL60 cells differentiated into neutrophils. The number of replicates for wt LukAB and mutant was 37 and 4, respectively. Non-linear 4 parameter logistic (4PL) curve fit regression was used to fit the data.

FIG. 10 illustrates the LukB mutations in the membrane binding cleft. Toxicity of LukAB mutant containing alanine substitution of LukB H180, E197, and R203 presumably involved in phosphocholine binding was determined in HL60 cells differentiated into neutrophils. The number of replicates for wt LukAB and mutant was 37 and 4, respectively. Non-linear 4 parameter logistic (4PL) curve fit regression was used to fit the data.

FIG. 11 illustrates the immunogenicity of select toxoids: The indicated combined mutant toxoids (at least one mutation in each subunit) were formulated with ALHYDROGEL® and used to immunize groups of 5 mice. Serum ELISA binding (A) and neutralization (B) titers were determined.

DETAILED DESCRIPTION

Disclosed herein are mutant staphylococcal leukocidin subunit polypeptides, e.g., a mutant LukA subunit polypeptide, a mutant LukB subunit polypeptide, or a mutant LukAB dimer, compositions comprising one or more mutant leukocidin subunits as disclosed herein, and methods of eliciting an immune response against staphylococci, e.g. *S. aureus*, or treating or preventing a staphylococcal infection in a subject, comprising administering to a subject an effective amount of a mutant staphylococcal leukocidin subunit polypeptide as disclosed herein.

In this disclosure, reference is made to the LukAB dimer, and separately, the LukA subunit and LukB subunit. One of ordinary skill in the art would understand that LukA is also referred to as LukH and that LukB is also referred to as LukG in the field of this disclosure, e.g., see U.S. Pat. No. 8,431,687 (LukAB), Badarau A. et al., J. Biol. Chem. 290(1): 142-56 (2015) (LukGH), and Badarau A. et al. MABS 9(7): 1347-60 (2016) (LukGH).

It is to be noted that the term "a" or "an" entity refers to one or more of that entity; for example, "a polypeptide," is understood to represent one or more polypeptides. As such, the terms "a" (or "an"), "one or more," and "at least one" can be used interchangeably herein.

The terms "nucleic acid" or "nucleic acid fragment" refers to any one or more nucleic acid segments, e.g., DNA or RNA fragments, present in a polynucleotide or construct. Two or more nucleic acids of the disclosure can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., Gene Therapy 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide," a "protein," an "amino acid chain," an "amino acid sequence," or any other term used to refer to a chain or chains of two or more amino acids, are included in the definition of a "polypeptide," (even though each of these terms can have a more specific meaning) and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The terms "staphylococcal leukocidin subunit polypeptide," "staphylococcal leukocidin subunit," "LukA subunit," "LukA polypeptide," "LukB subunit," "LukB polypeptide," and the like, as used herein, encompass mature or full length staphylococcal leukocidin subunits (e.g., LukA or LukB), and fragments, variants or derivatives of mature or full length staphylococcal leukocidin subunits (e.g., LukA and LukB), and chimeric and fusion polypeptides comprising mature or full length staphylococcal leukocidin subunits (e.g., LukA and LukB) or one or more fragments of mature or full length staphylococcal leukocidin subunits (e.g., LukA and LukB). In certain aspects, staphylococcal leukocidin subunits as disclosed herein are mutant staphylococcal leukocidin subunits, which are reduced in toxicity relative to a corresponding wild-type leukocidin subunit and/or are not significantly reduced in immunogenicity relative to a corresponding wild-type leukocidin subunit. By "corresponding wild-type leukocidin subunit" is meant the native leukocidin subunit from which the mutant leukocidin subunit was derived.

Pore forming toxins, e.g., single-component alpha-hemolysin and the bi-component hemolysins and leukotoxins, play an important role in staphylococcal immune evasion. These toxins kill key immune cells and cause tissue destruction, thereby often weakening the host during the first stage of infection and promoting bacterial dissemination and metastatic growth. The bi-component toxin LukAB, comprising LukA and LukB subunits, is unique in that it is secreted as a dimer which then octamerizes on the surface of the cells to form pores. In contrast, for example, the two PVL components, LukS-PV and LukF-PV, are secreted separately and form the pore-forming octameric complex upon binding of LukS-PV to its receptor and subsequent binding of LukF-PV to LukS-PV (Miles et al., Protein Sci, 2002. 11(4): p. 894-902; Pedelacq et al., Int J Med Microbiol, 2000. 290(4-5): p. 395-401). Targets of PVL include, e.g., polymorphonuclear neutrophils (PMN), monocytes, and macrophages.

Other bi-component toxins have been characterized in *S. aureus*: S components HlgA and HlgC and the F component HlgB for γ-hemolysin; LukS-PV, LukF-PV, LukE (S) and LukD (F); and LukM (S) and LukF-PV-like (F) (PCT Publication No. WO 2011/112570, which is incorporated herein by reference). Due to their close similarity, these S components can combine with an F component and form an active toxin with different target specificity (Ferreras et al., Biochim Biophys Acta, 1998. 1414(1-2): p. 108-26; Prevost et al., Infect Immun, 1995. 63(10): p. 4121-9). γ-Hemolysin is strongly hemolytic and 90% less leukotoxic than PVL, while PVL is non-hemolytic. However, HlgA or HlgC paired with LukF-PV promotes leukotoxic activity (Prevost et al., Infect Immun, 1995. 63(10): p. 4121-9). PVL and other leukotoxins lyse neutrophils, and Hlg is hemolytic (Kaneko et al., Biosci Biotechnol Biochem, 2004. 68(5): p. 981-1003) and was also reported to lyse neutrophils (Malachowa et al., PLoS One, 2011. 6(4): p. e18617). While PVL subunits are phage derived (the F&S leukocidin), Hlg proteins are derived from Hlg locus (hlg) and found in 99% of clinical isolates (Kaleko et al.). Hlg subunits are strongly upregulated during S. aureus growth in blood (Malachowa et al.), and Hlg was shown to be involved in survival of S. aureus in blood (Malachowa et al., Virulence, 2011. 2(6)). The mutant USA300 A-hlgABC has reduced capacity to cause mortality in a mouse bacteremia model (Malachowa et al., PLoS One, 2011. 6(4): p. e18617). Alonzo et al. have shown that LukED toxin is critical for bloodstream infections in mice (Alonzo et al., Mol Microbiol, 2012. 83(2): p. 423-35). LukAB has been described to synergize with PVL to enhance human PMN lysis (Ventura et al., PLoS One, 2010. 5(7): p. e11634; LukAB referred to as LukGH therein).

The terms "fragment," "analog," "derivative," or "variant" when referring to a staphylococcal leukocidin subunit (e.g., LukA or LukB) of the present disclosure include any polypeptide which retains at least some of the immunogenicity or antigenicity of the source protein. Fragments of staphylococcal leukocidin subunits (e.g., LukA or LukB) as described herein include proteolytic fragments, deletion fragments and in particular, fragments of staphylococcal leukocidin subunits (e.g., LukA or LukB) which exhibit increased solubility during expression, purification, or administration to an animal. Fragments of staphylococcal leukocidin subunits (e.g., LukA or LukB) as described herein further include proteolytic fragments or deletion fragments which exhibit reduced pathogenicity or toxicity when delivered to a subject. Polypeptide fragments further include any portion of the polypeptide which comprises an antigenic or immunogenic epitope of the source polypeptide, including linear as well as three-dimensional epitopes.

An "epitopic fragment" of a polypeptide antigen is a portion of the antigen that contains an epitope. An "epitopic fragment" can, but need not, contain amino acid sequence in addition to one or more epitopes.

The term "variant," as used herein, refers to a polypeptide that differs from the recited polypeptide due to amino acid substitutions, deletions, insertions, and/or modifications. Non-naturally occurring variants can be produced using art-known mutagenesis techniques. In some aspects, variant polypeptides differ from an identified sequence by substitution, deletion or addition of three amino acids or fewer. Such variants can generally be identified by modifying a polypeptide sequence, and evaluating the antigenic or pathogenic properties of the modified polypeptide using, for example, the representative procedures described herein. In some aspects, variants of a wild-type staphylococcal leukocidin subunit (e.g., LukA, LukB, or both) form a protein complex which is less toxic than the wild-type complex.

Polypeptide variants disclosed herein exhibit at least about 85%, 90%, 94%, 95%, 96%, 97%, 98%, 99% or 99.9% sequence identity with an identified polypeptide. Variant polypeptides can comprise conservative or non-conservative amino acid substitutions, deletions or insertions. Variants can comprise staphylococcal leukocidin subunits (e.g., LukA or LukB, or both) identical to a wild-type leukocidin subunit except for having one or more substitutions, deletions, or a combination thereof, where the substitutions, deletions, or combination thereof render a leukocidin complex comprising the variant leukocidin subunit less toxic than a corresponding wild-type protein complex and/or the substitutions do not significantly reduce the immunogenicity of a leukocidin complex comprising the variant leukocidin subunit relative to a corresponding wild-type protein complex. In certain aspects, the mutant is immunogenic and elicits antibodies that can neutralize the action of the wild type toxin. In certain aspects, the mutant is immunogenic and elicits antibodies that can more effectively neutralize the action of the wild type toxin relative to the corresponding wild-type leukocidin subunit. In certain aspects, the variants can comprise staphylococcal leukocidin subunits (e.g., LukA or LukB, or both) identical to a wild-type leukocidin subunit except for having 1, 2, 3, 4, 5, 6, 7, 8, 9, 10, 11, 12, 13, 14, 15, 16, or 17 amino acid substitutions, deletions, or a combination thereof. Derivatives of staphylococcal leukocidin subunits (e.g., LukA and LukB) as described herein are polypeptides which have been altered so as to exhibit additional features not found on the native polypeptide. Examples include fusion proteins. An analog is another form of a staphylococcal leukocidin subunit (e.g., LukA and LukB) described herein. An example is a proprotein which can be activated by cleavage of the proprotein to produce an active mature polypeptide.

Variants can also, or alternatively, contain other modifications, whereby, for example, a polypeptide can be conjugated or coupled, e.g., fused to a heterologous amino acid sequence, e.g., a signal (or leader) sequence at the N-terminal end of the protein which co-translationally or post-translationally directs transfer of the protein. The polypeptide can also be conjugated or produced coupled to a linker or other sequence for ease of synthesis, purification or identification of the polypeptide (e.g., 6-His), or to enhance binding of the polypeptide to a solid support. For example, the polypeptide can be conjugated or coupled to an immunoglobulin Fc region. The polypeptide can also be conjugated or coupled to a sequence that imparts or modulates the immune response to the polypeptide (e.g., a T-cell epitope, B-cell epitope, cytokine, chemokine, etc.) and/or enhances uptake and/or processing of the polypeptide by antigen presenting cells or other immune system cells. The polypeptide can also be conjugated or coupled to other polypeptides/epitopes from Staphylococcus sp. and/or from other bacteria and/or other viruses to generate a hybrid immunogenic protein that alone or in combination with various adjuvants can elicit protective immunity to other pathogenic organisms. The polypeptide can also be conjugated or coupled to moieties which confer greater stability or improve half-life such as, but not limited to albumin, an immunoglobulin Fc region, polyethylene glycol (PEG), and the like. The polypeptide can also be conjugated or coupled to moieties (e.g., immunogenic carbohydrates, e.g., a capsular polysaccharide or a surface polysaccharide) from Staphylococcus sp. and/or from other bacteria and/or other viruses to generate a modified immunogenic protein that alone or in combination with one or more adjuvants can enhance and/or synergize protective immunity. In certain aspects, the polypeptide described herein further comprises an immunogenic carbohydrate. In one embodiment, the immunogenic carbohydrate is a saccharide.

The term "saccharide" throughout this specification can indicate polysaccharide or oligosaccharide and includes both. Polysaccharides as provided herein can be isolated from bacteria and can be sized by known methods. For example, full length polysaccharides can be "sized" (e.g., their size can be reduced by various methods such as acid hydrolysis treatment, hydrogen peroxide treatment, sizing by EMULSIFLEX® followed by a hydrogen peroxide treatment to generate oligosaccharide fragments or microfluidization). Polysaccharides can be sized in order to reduce viscosity in polysaccharide samples and/or to improve filterability for conjugated products. Oligosaccharides have a low number of repeat units (e.g., 5-30 repeat units) and are typically hydrolyzed polysaccharides. Polysaccharides as provided herein can be produced recombinantly.

S. aureus capsular antigens are surface associated, limited in antigenic specificity, and highly conserved among clinical isolates. In one embodiment, the immunogenic carbohydrate as provided by the disclosure is a capsular polysaccharide (CP) of S. aureus. In one embodiment, a capsular saccharide can be a full length polysaccharide, however in other aspects it can be one oligosaccharide unit, or a shorter than native length saccharide chain of repeating oligosaccharide units. Serotyping studies of staphylococcal isolates have revealed several putative capsular serotypes, with types 5 and 8 (CPS and CP8) being the most prevalent among isolates from clinical infections, accounting for about 25% and 50% of isolates recovered from humans, respectively (O'Riordan and Lee, Clinical Microbiology Reviews, January 2004, p. 218-234, Vol. 17, No. 1; Poutrel and Sutra, J Clin Microbiol. 1993 Feb; 31(2):467-9). The same isolates were also recovered from poultry, cows, horses and pigs (Tollersrud et al., J Clin Microbiol. 2000 August; 38(8):2998-3003; Cunnion K M et al., Infect Immun. 2001 November; 69(11):6796-803). Type 5 and 8 capsular polysaccharides purified from the prototype strains Reynolds and Becker, respectively, are structurally very similar to each other and to the capsule made by strain T, described previously by Wu and Park (Wu and Park. 1971. J. Bacteriol. 108:874-884). Type 5 has the structure $(\rightarrow A)$-3-O-Ac-$\beta$-D-ManNAcA-$(1\rightarrow 4)$-$\alpha$-L-FucNAc-$(1\rightarrow 3)$-$\beta$-D-FucNAc-$(1\rightarrow)_n$ (Fournier, J. M., et al., 1987. Ann. Inst. Pasteur Microbiol. 138:561-567; Moreau, M., et al., 1990. Carbohydr. Res. 201:285-297), and type 8 has the structure $(\rightarrow 3)$-4-O-Ac-$\beta$-D-ManNAcA-$(1\rightarrow 3)$-$\alpha$-L-FucNAc-$(1\rightarrow 3)$-$\beta$-D-FucNAc-$(1\rightarrow)_n$ (Fournier, J. M., et al., 1984. Infect. Immun. 45:87-93). Type 5 and 8 polysaccharides differ only in the linkages between the sugars and in the sites of 0-acetylation of the mannosaminuronic acid residues, yet they are serologically distinct.

Type 5 and 8 CP conjugated to a detoxified recombinant Pseudomonas aeruginosa exotoxin A carrier were shown to be highly immunogenic and protective in a mouse model (A Fattom et al., Infect Immun. 1993 March; 61(3): 1023-1032; A Fattom et al., Infect Immun. 1996 May; 64(5): 1659-1665) and passive transfer of the CPS-specific antibodies from the immunized animals induced protection against systemic infection in mice (Lee et al., Infect Immun. 1997 October; 65(10): 4146-4151) and against endocarditis in rats challenged with a serotype 5 S. aureus (Shinefield H et al., N Engl J Med. 2002 Feb. 14; 346(7):491-6). A bivalent CP5 and CP8 conjugate vaccine (StaphVAX®, Nabi Biopharmaceutical) was developed that provided 75% protection in mice against S. aureus challenge. The vaccine has been tested on humans (Fattom A I et al., Vaccine. 2004 Feb. 17; 22(7):880-7; Maira-Litran T et al., Infect Immun. 2005 October; 73(10):6752-62). In certain aspects, the oligopeptide of the disclosure is combined with or conjugated to an immunogenic carbohydrate (e.g., CP5, CP8, a CP fragment or a combination thereof).

Immunization with poly-N-acetylglucosamine (PNAG) (McKenney D. et al., Science. 1999 May 28;284(5419): 1523-7) or poly-N-succinyl glucosamine (PNSG) (Tuchscherr L P. et al., Infect Immun. 2008 December; 76(12): 5738-44. Epub 2008 Sep 22), both S. aureus surface carbohydrates, has been shown to generate at least partial protection against S. aureus challenge in experimental animal models. PNSG was identified as the chemical form of the S. epidermidis capsular polysaccharide/adhesin (PS/A) which mediates adherence of coagulase-negative staphylococci (CoNS) to biomaterials, serves as the capsule for strains of CoNS that express PS/A, and is a target for protective antibodies. PNSG is also made by S. aureus, where it is an environmentally regulated, in vivo-expressed surface polysaccharide and similarly serves as a target for protective immunity (McKenney D. et al., J. Biotechnol. 2000 Sep. 29; 83(1-2): 37-44). In certain aspects, the immunogenic carbohydrate can be a surface polysaccharide, e.g., poly-N-acetylglucosamine (PNAG), poly-N-succinyl glucosamine (PNSG), a surface polysaccharide fragment or a combination thereof.

Wall Teichoic Acid (WTA) is a prominent polysaccharide widely expressed on S. aureus strains (Neuhaus, F. C. and J. Baddiley, Microbiol Mol Biol Rev, 2003. 67(4):686-723) and antisera to WTA have been shown to induce opsonophagocytic killing alone and in presence of complement ((Thakker, M., et al., Infect Immun, 1998. 66(11): 5183-9), and Fattom et al, U.S. Pat. No. 7,754,225). WTA is linked to peptidoglycans and protrudes through the cell wall becoming prominently exposed on non-encapsulated strains such as USA300 responsible for most cases of community acquired MRSA (CA MRSA) in the US (Hidron, A. I., et al., Lancet Infect Dis, 2009. 9(6):384-92).

Lipoteichoic acid (LTA) is a constituent of the cell wall of Gram-positive bacteria, e.g., Staphylococcus aureus. LTA can bind to target cells non-specifically through membrane phospholipids, or specifically to CD14 and to Toll-like receptors. Target-bound LTA can interact with circulating antibodies and activate the complement cascade to induce a passive immune kill phenomenon. It also triggers the release from neutrophils and macrophages of reactive oxygen and nitrogen species, acid hydrolases, highly cationic proteinases, bactericidal cationic peptides, growth factors, and cytotoxic cytokines, which can act in synergy to amplify cell damage.

In certain aspects, a surface polysaccharide is combined with or conjugated to a polypeptide of the disclosure. In certain aspects the surface polysaccharide is, e.g., poly-N-acetylglucosamine (PNAG), poly-N-succinyl glucosamine (PNSG), Wall Teichoic Acid (WTA), Lipoteichoic acid (LPA), a fragment of any of said surface polysaccharides, or a combination of two or more of said surface polysaccharides.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window and a homologous polypeptide from another isolate. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which is available from the National Center for Biotechnology Information as of September 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The term "epitope," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind its antigen as determined by any method well known in the art. Immunospecific binding excludes non-specific binding but does not necessarily exclude cross-reactivity with other antigens. Whereas all immunogenic epitopes are antigenic, antigenic epitopes need not be immunogenic.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host. Various species exhibit particular bias for certain codons of a particular amino acid.

The term "composition," or "pharmaceutical composition" can include compositions containing immunogenic polypeptides of the disclosure along with e.g., adjuvants or pharmaceutically acceptable carriers, excipients, or diluents, which are administered to an individual already suffering from S. aureus infection or an individual in need of immunization against S. aureus infection.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some aspects, the polypeptides, polynucleotides, compositions, and vaccines described herein are pharmaceutically acceptable.

An "effective amount" is that amount the administration of which to an individual, either in a single dose or as part of a series, is effective for treatment or prevention. An amount is effective, for example, when its administration results in a reduced incidence of S. aureus infection relative to an untreated individual, as determined, e.g., after infection or challenge with infectious S. aureus, including, but is not limited to reduced bacteremia, reduced toxemia, reduced sepsis, reduced symptoms, increased immune response, modulated immune response, or reduced time required for recovery. This amount varies depending upon the health and physical condition of the individual to be treated, the taxonomic group of individual to be treated (e.g., human, non-human primate, primate, etc.), the responsive capacity of the individual's immune system, the extent of treatment or protection desired, the formulation of the vaccine, a professional assessment of the medical situation, and other relevant factors. It is expected that the effective amount will fall in a relatively broad range that can be determined through routine trials. Typically a single dose is from about 10 µg to 10 mg/kg body weight of purified polypeptide or an amount of a modified carrier organism or virus, or a fragment or remnant thereof, sufficient to provide a comparable quantity of recombinantly expressed mutant staphylococcal leukocidin subunit (e.g., LukA or LukB, or both), as described herein. The term "peptide vaccine" or "subunit vaccine" refers to a composition comprising one or more polypeptides described herein, which when administered to an animal are useful in stimulating an immune response against staphylococcal (e.g., S. aureus) infection.

The term "subject" is meant any subject, particularly a mammalian subject, for whom diagnosis, prognosis, immunization, or therapy is desired. Mammalian subjects include, but are not limited to, humans, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In one embodiment, the subject is a human subject.

As used herein, a "subject in need thereof" refers to an individual for whom it is desirable to treat, i.e., to prevent, cure, retard, or reduce the severity of staphylococcal (e.g., S. aureus) disease symptoms, or result in no worsening of disease cause by S. aureus over a specified period of time, or both.

The terms "priming" or "primary" and "boost" or "boosting" as used herein to refer to the initial and subsequent immunizations, respectively, i.e., in accordance with the definitions these terms normally have in immunology. However, in certain aspects, e.g., where the priming component and boosting component are in a single formulation, initial and subsequent immunizations may not be necessary as both the "prime" and the "boost" compositions are administered simultaneously.

Mutant Polypeptides

Disclosed herein is an isolated mutant staphylococcal leukocidin subunit polypeptide comprising, consisting of, or consisting essentially of, a wild-type staphylococcal LukA subunit, a wild-type staphylococcal LukB subunit, or a wild-type staphylococcal LukAB dimer, except for having one or more mutations, e.g., amino acid substitutions, deletions, or a combination thereof at conserved residues in the LukA subunit, the LukB subunit, or in the LukAB dimer. In certain aspects, the one or more mutations comprises 1, 2, 3, 4, 5, 6, 7, 8, 9, 10, 11, 12, 13, 14, 15, 16, or 17 amino acid substitutions, deletions, insertions, or a combination thereof. In certain aspects, the amino acid substitutions, deletions, insertions, or a combination thereof are at conserved residues in the LukAB protomer/protomer interface region (also referred to as Interface 1 herein; FIG. 1), the dimer/dimer interface region (also referred to as Interface 2 herein; FIG. 1), the LukB membrane-binding cleft region (FIG. 1), the LukB pore forming region (PORE; FIG. 1), or any combination thereof. In certain aspects, the ability of the leukocidin subunits to form dimers, to oligomerize, to form pores on the surface of eukaryotic cells, or any combination thereof is disrupted. Thus, in certain aspects, the toxicity of the mutant leukocidin subunit or the mutant LukAB dimer relative to the corresponding wild-type LukA subunit, wild-type LukB subunit, or LukAB dimer is reduced. In certain aspects, the substitutions, deletions, or a combination thereof do not significantly reduce the immunogenicity of the mutant LukA subunit, mutant LukB subunit, or the mutant LukAB dimer relative to the corresponding wild-type leukocidin subunit or dimer.

Figure 2:
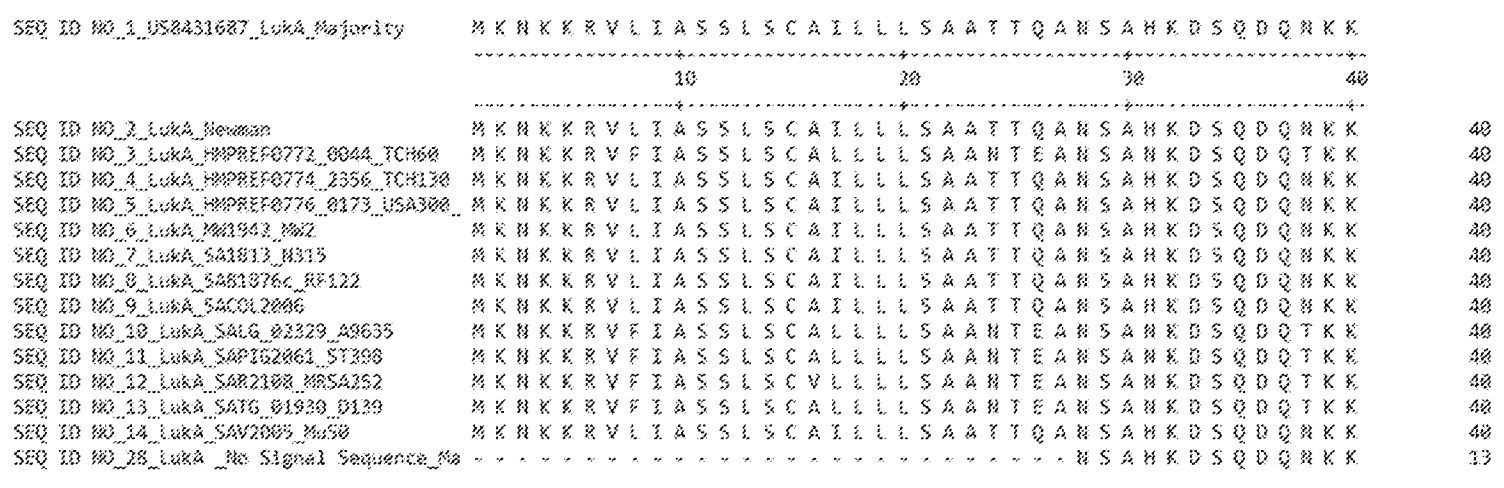
Figure 2:
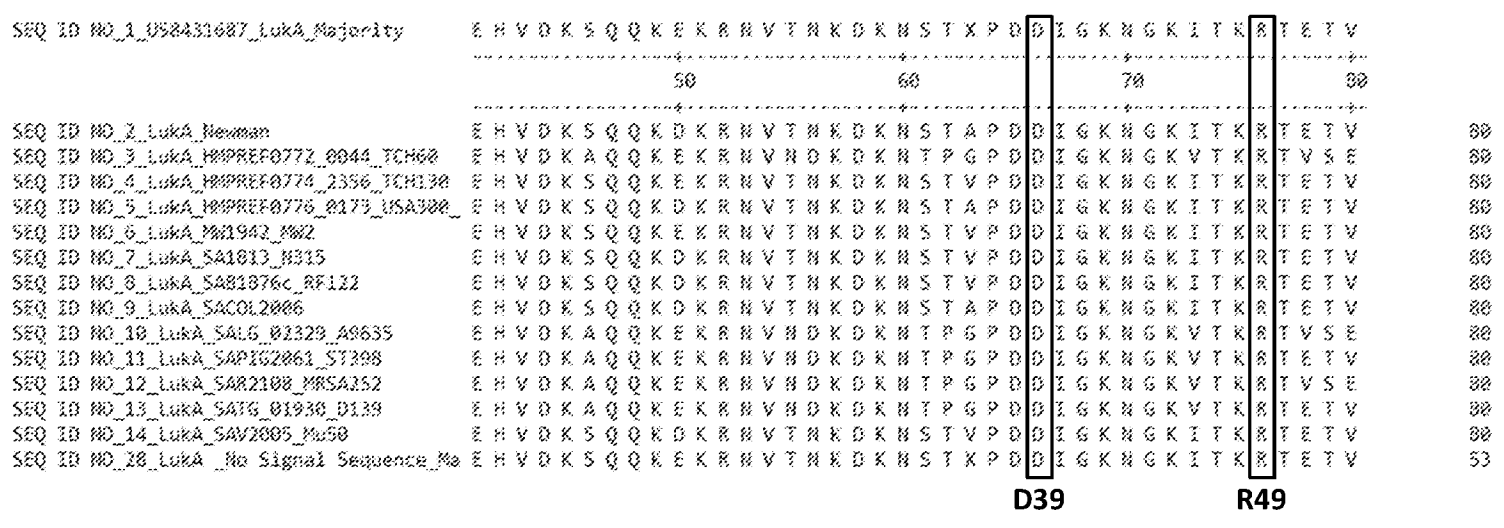
Figure 2:
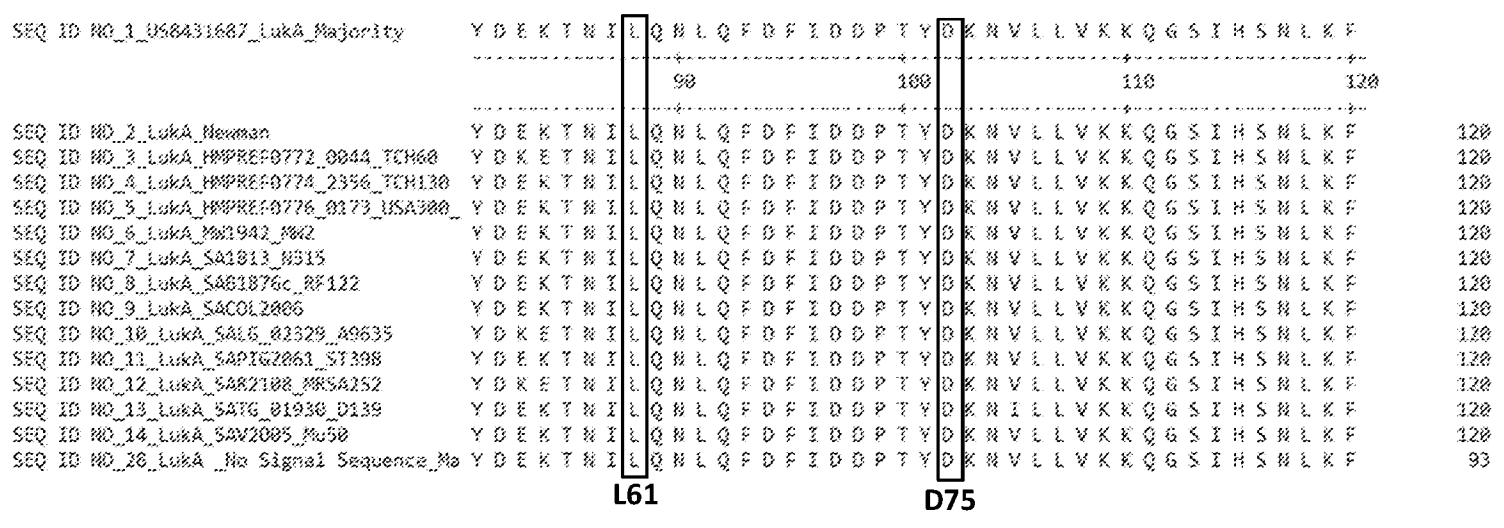
Figure 2:
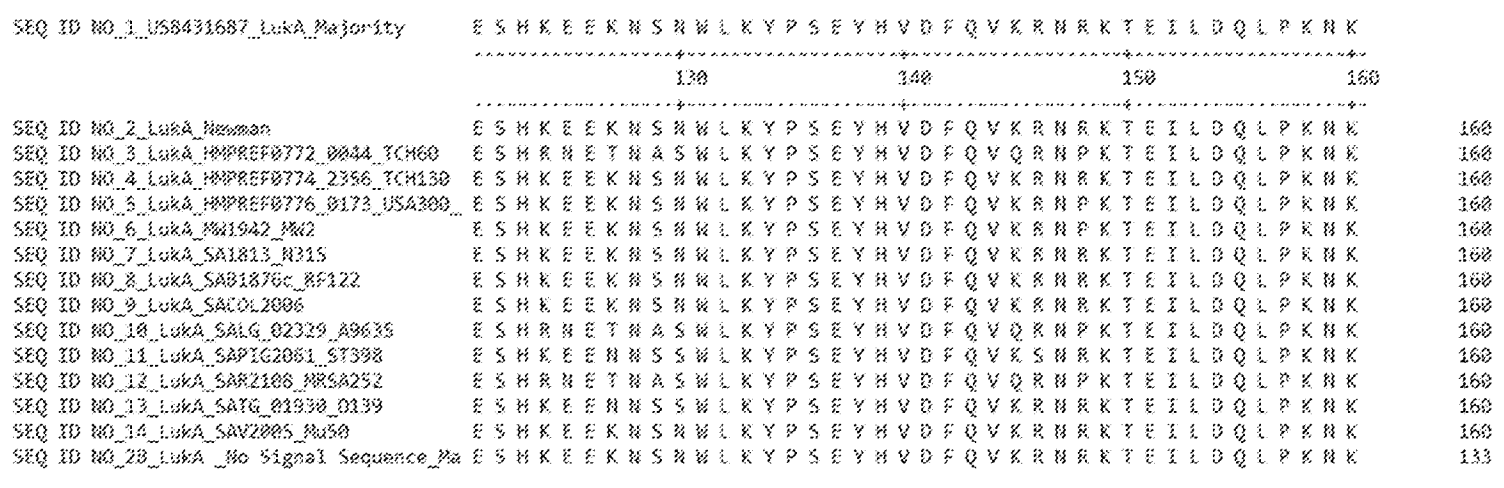
Figure 2:
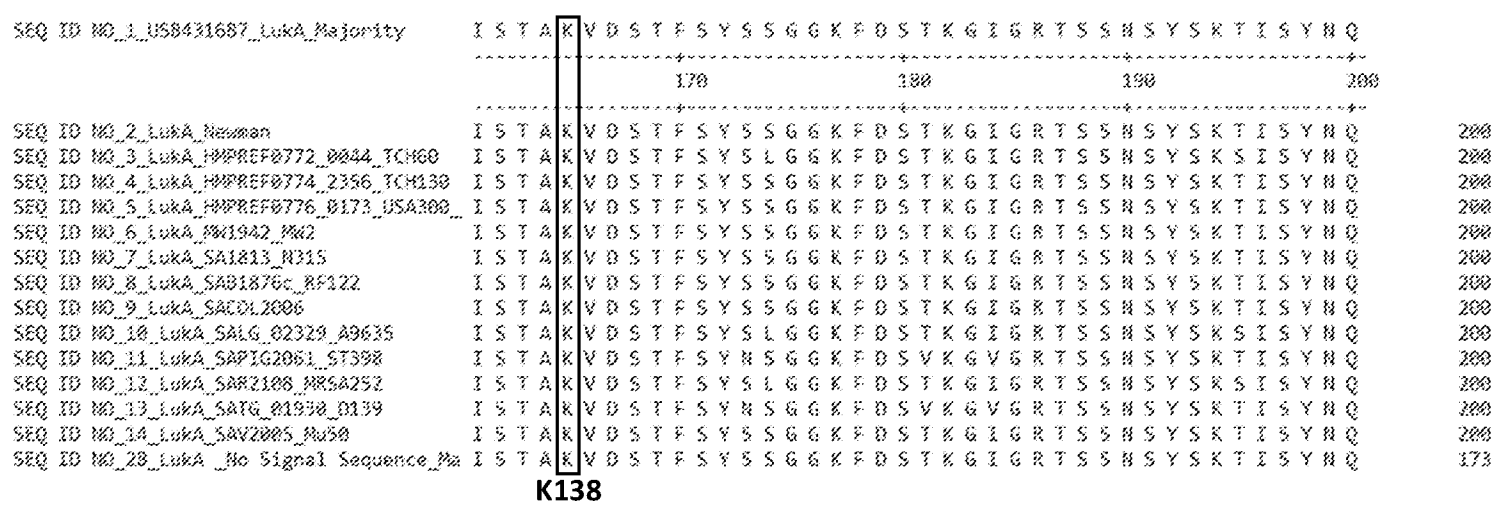
Figure 2:
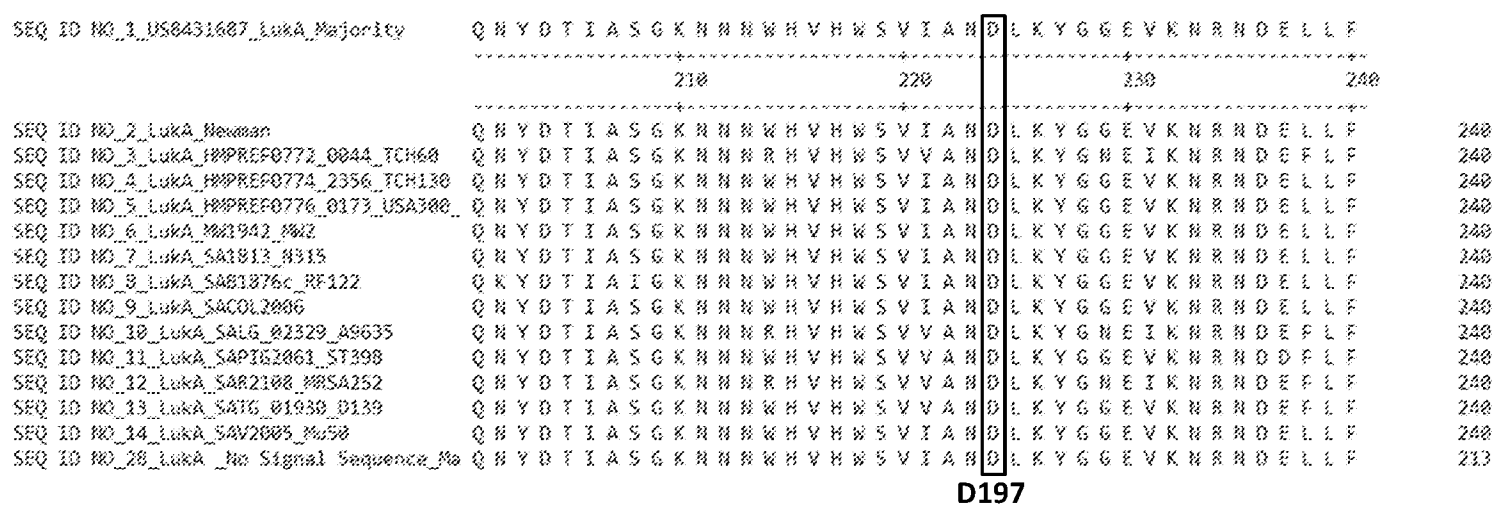
Figure 2:
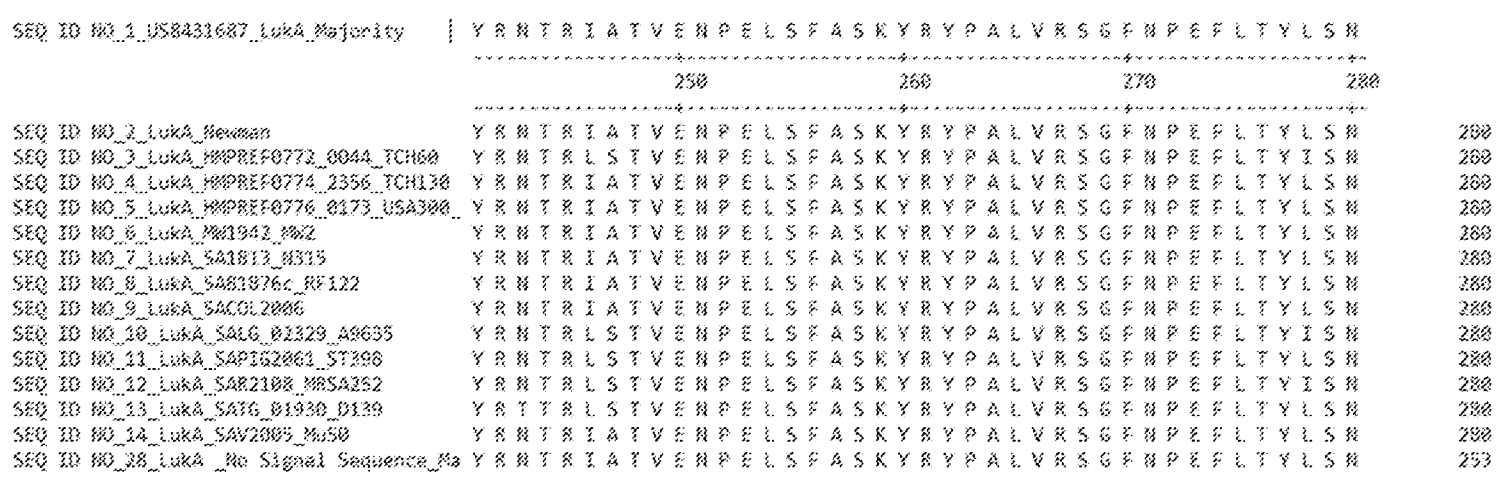
Figure 2:
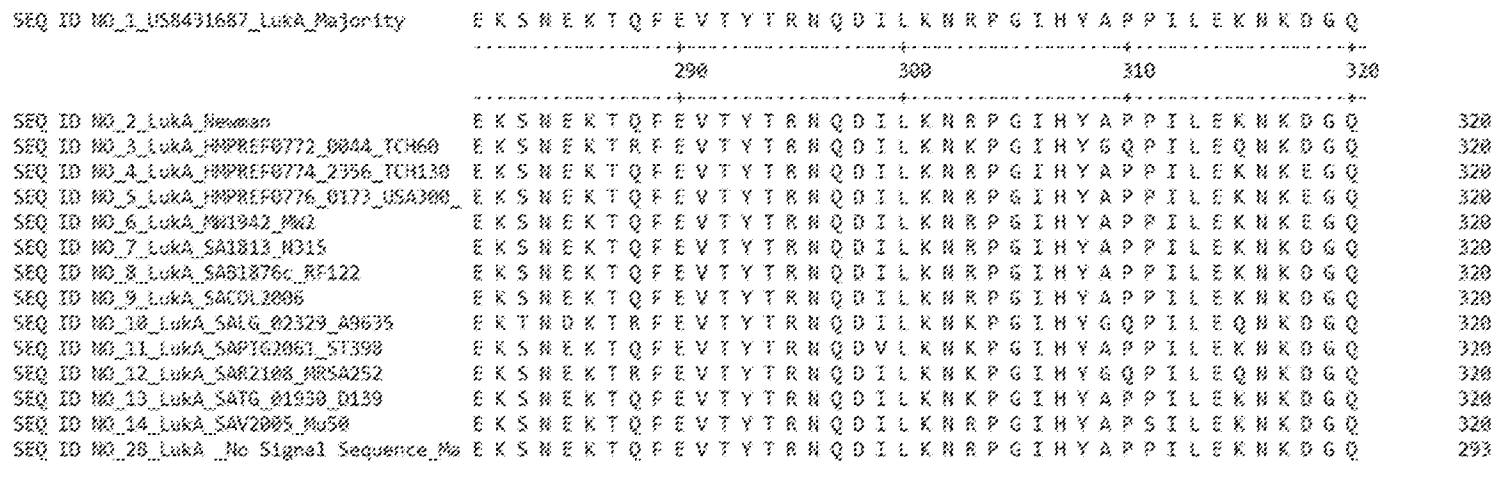
Figure 2:
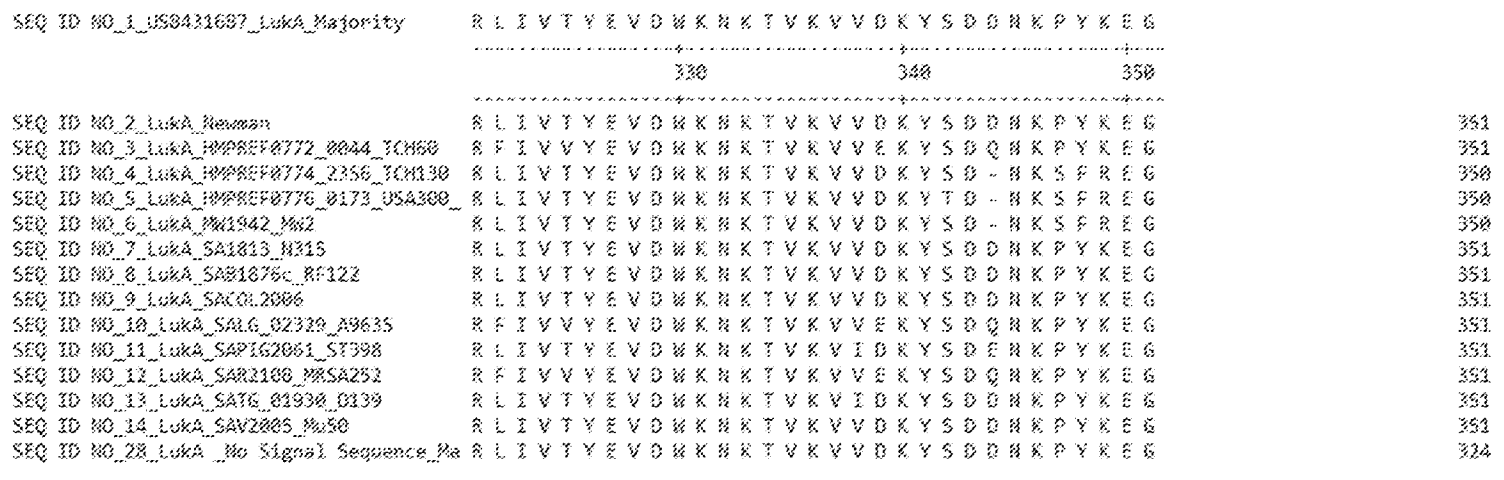
Figure 3:
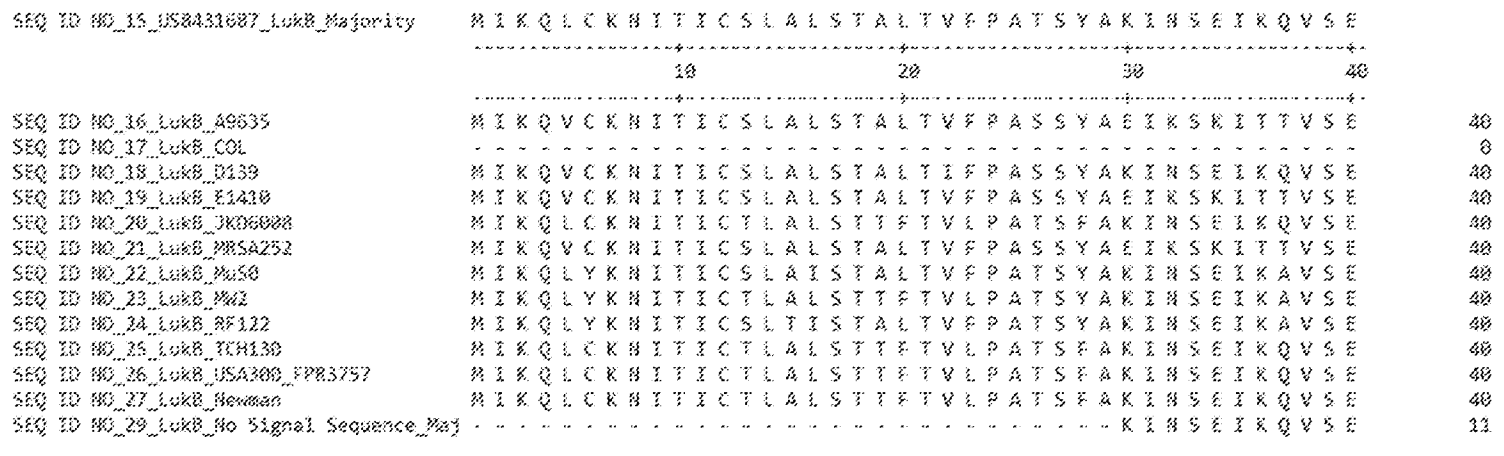
Figure 3:
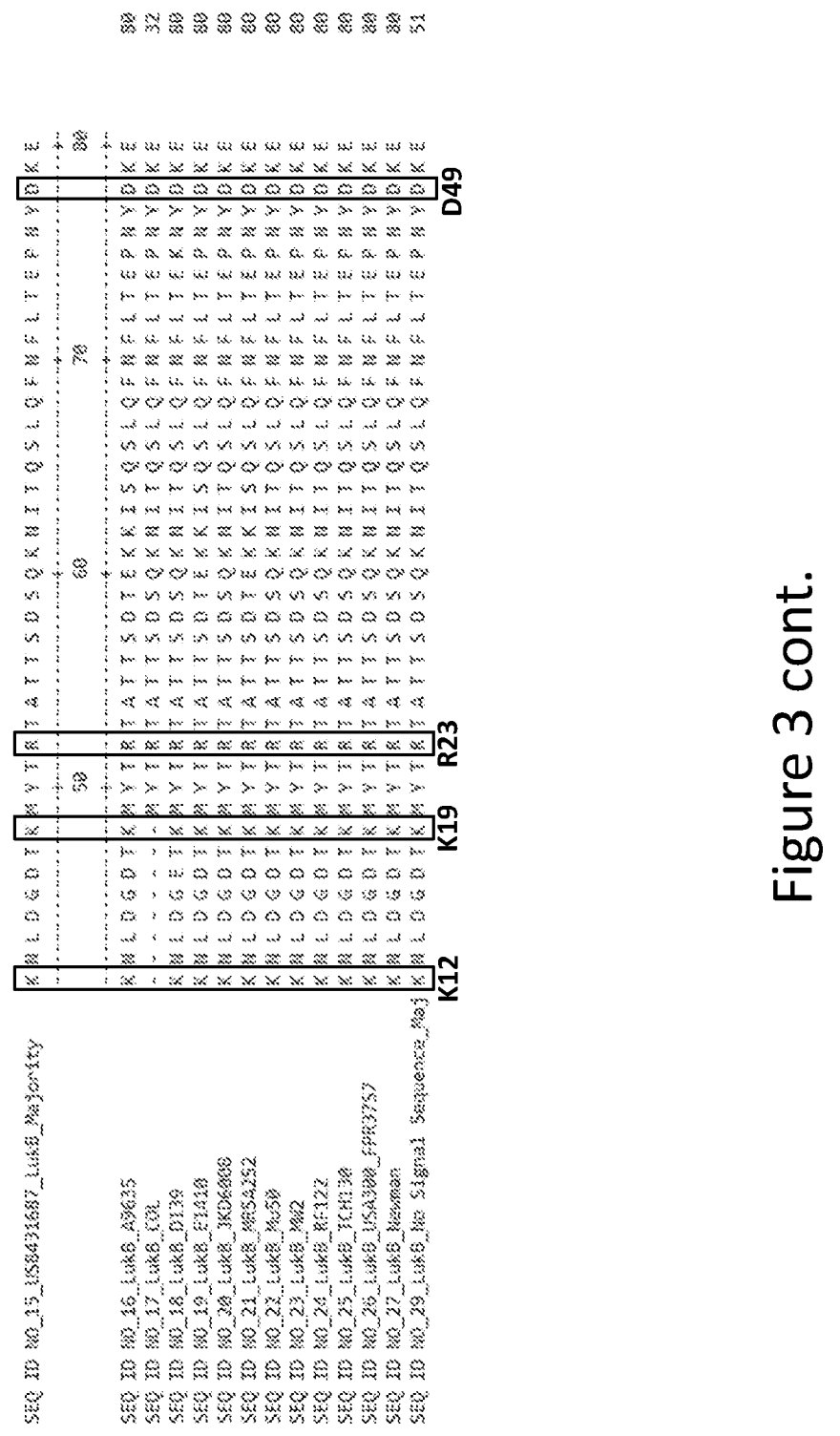
Figure 3:
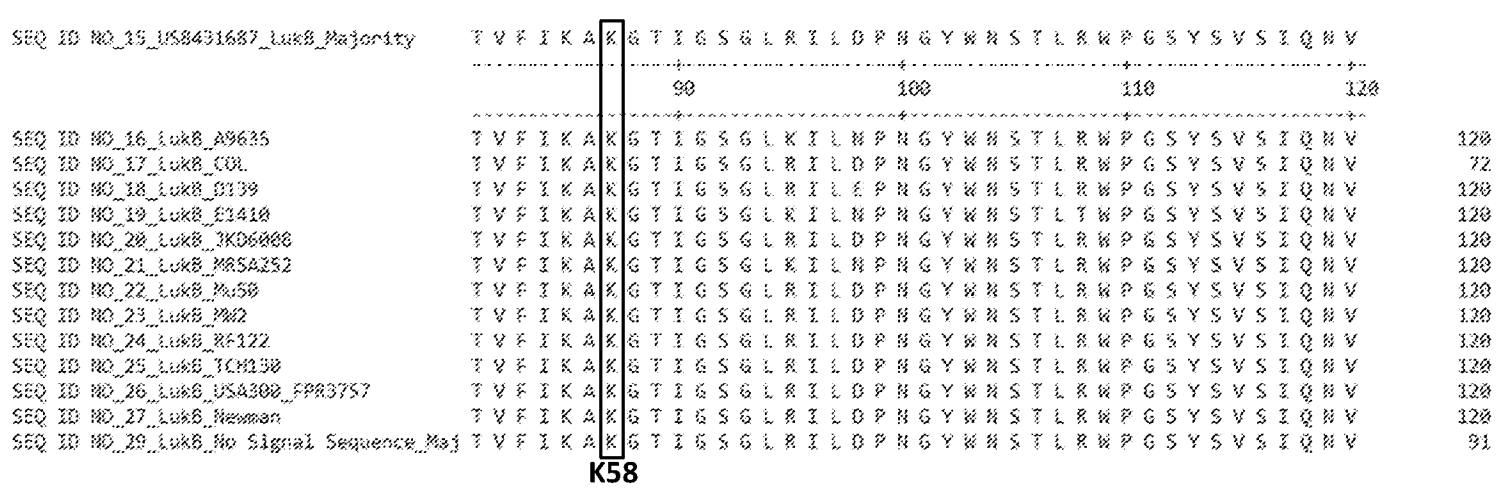
Figure 3:
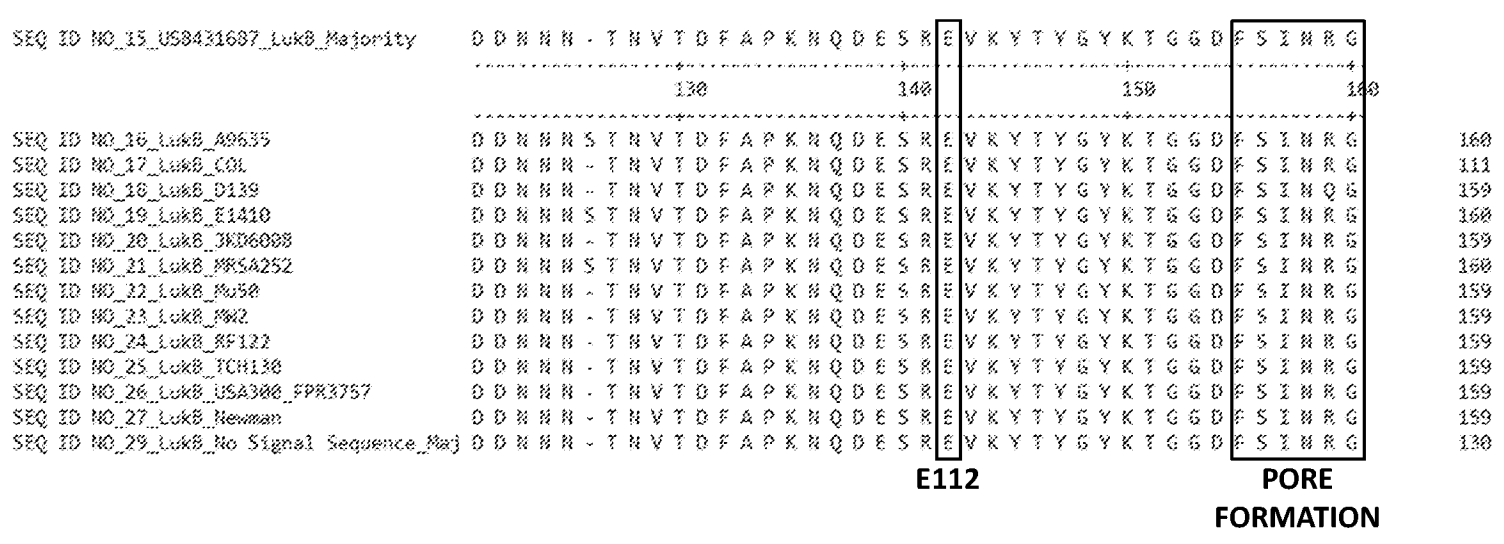
Figure 3:
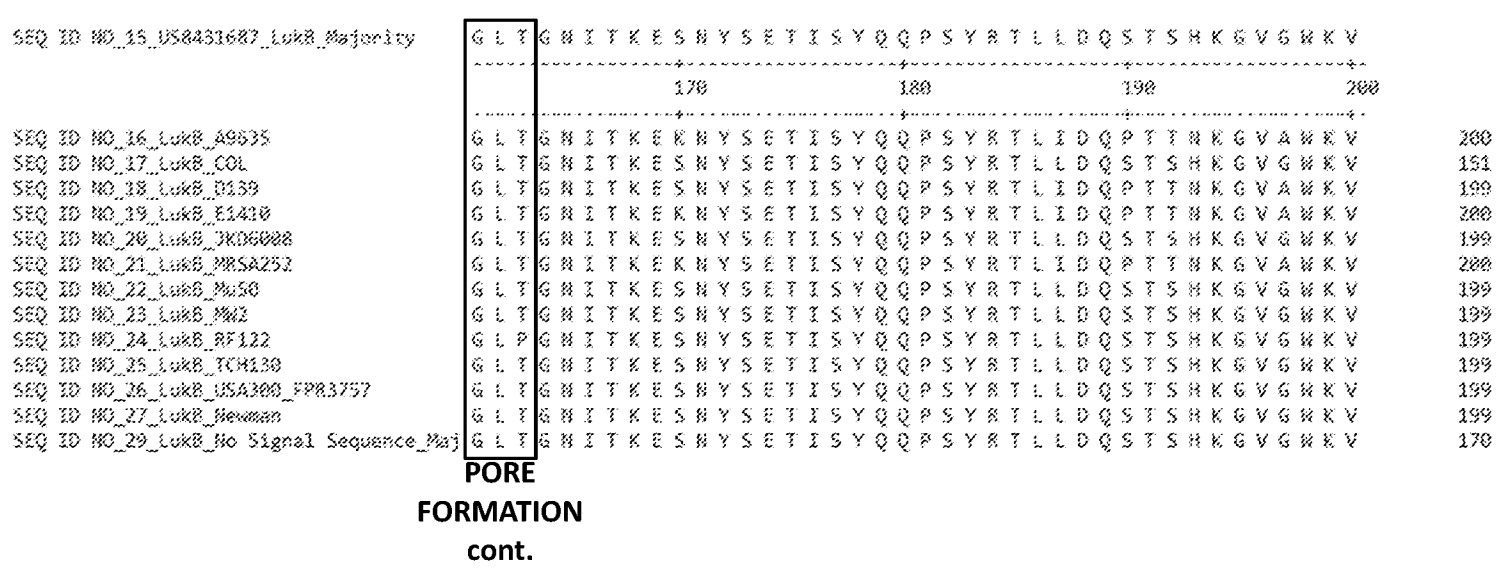
Figure 3:
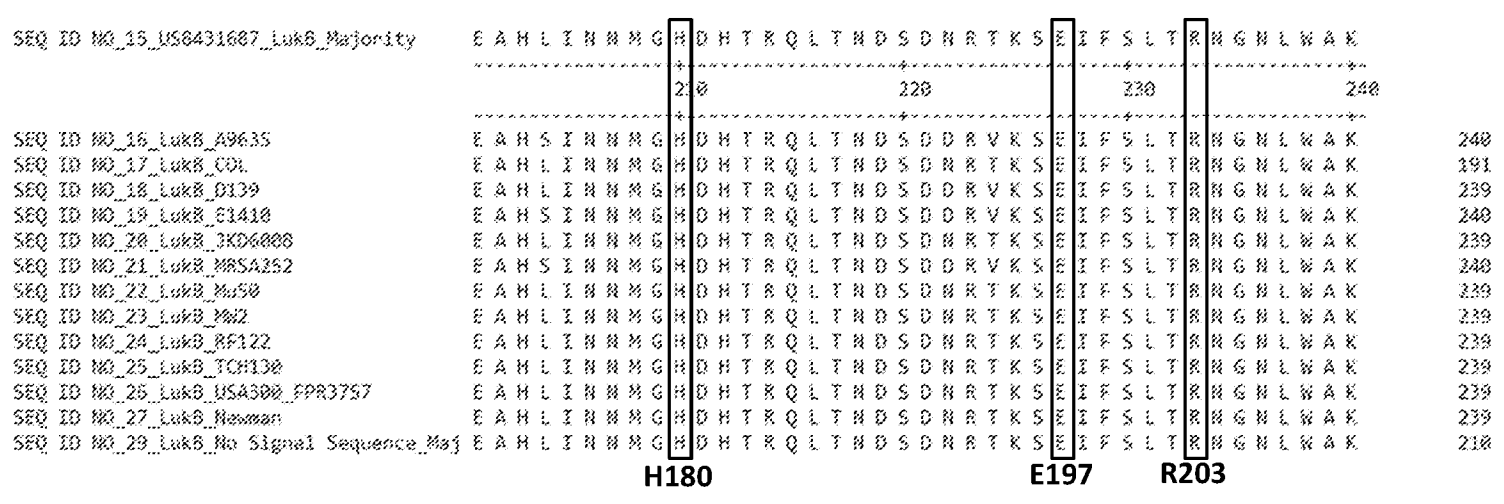
Figure 3:
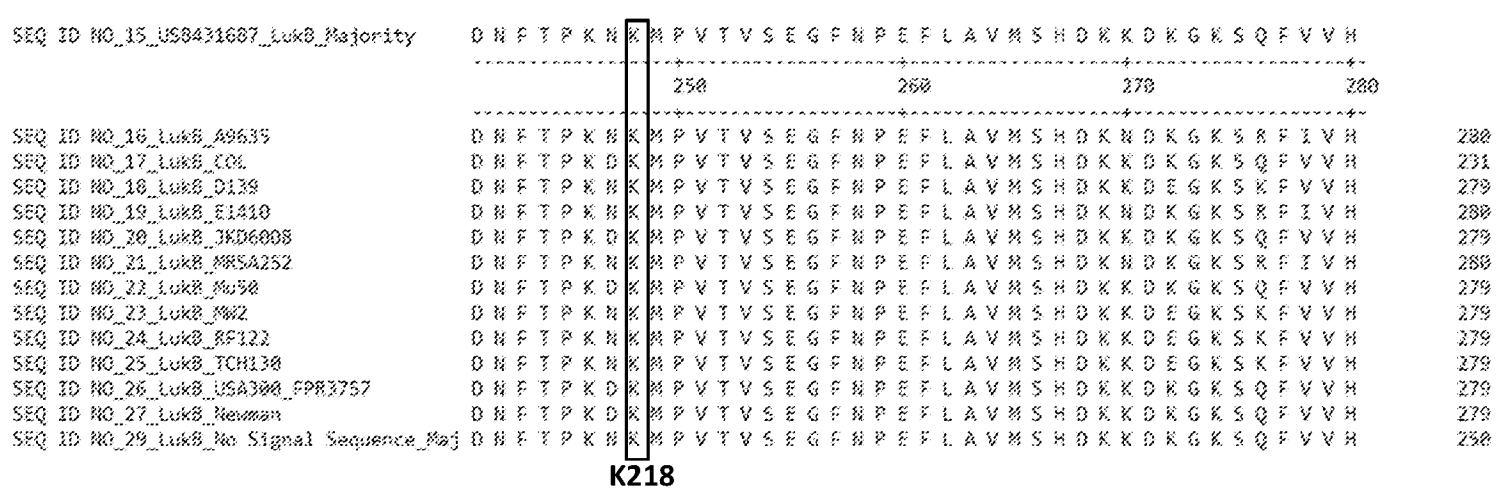
Figure 3:
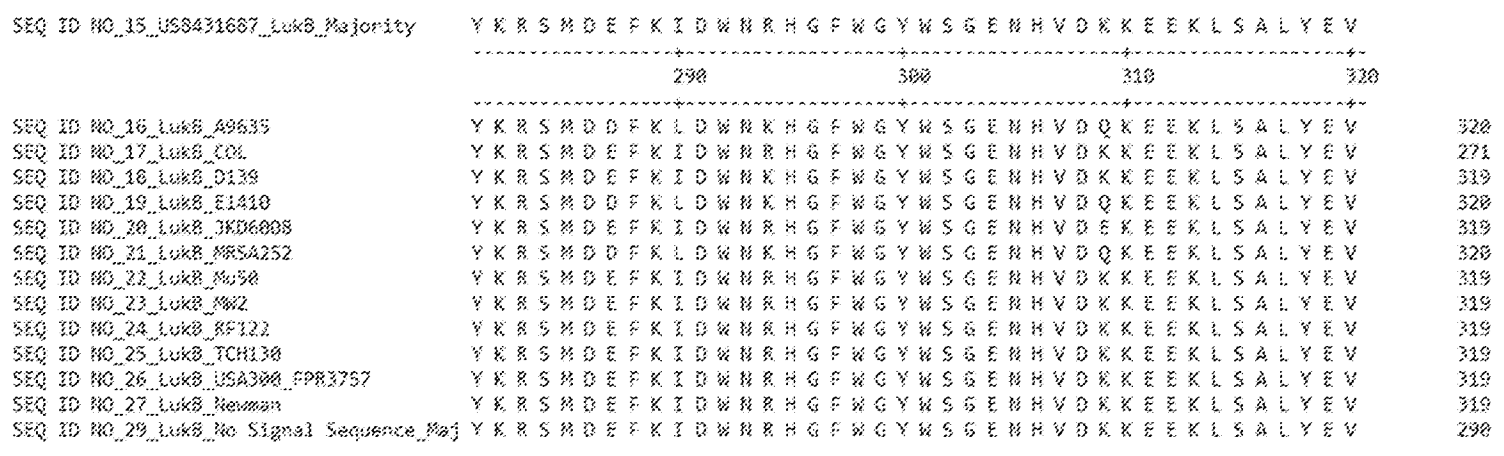
Figure 3:
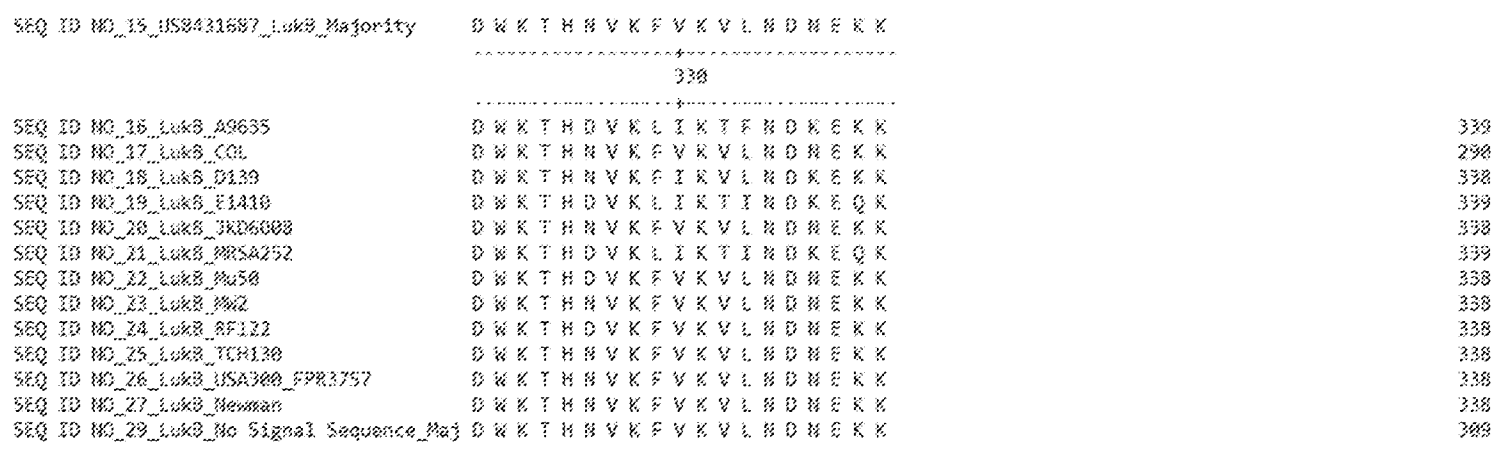

As referred to herein, "conserved amino acids" or "conserved residues" are those residues in the wild-type LukA subunit and LukB subunit polypeptide sequences shown in the alignments in FIG. 2 and FIG. 3, respectively, that are the same at corresponding positions across all or most LukA or LukB sequences, e.g., the sequences in the alignment. LukA and LukB are conserved across various S. aureus strains. FIGS. 2 and 3 show alignments of representative LukA (SEQ ID Nos. 2-14) and LukB (SEQ ID Nos. 16-27) amino acid sequences respectively. SEQ ID NOs. 1 and 28 depict full-length and mature versions of a consensus majority LukA amino acid sequence in which the most frequently used amino acid at each position is represented. SEQ ID NOs. 15 and 29 depict full-length and mature versions of a consensus majority LukB amino acid sequence in which the most frequently used amino acid at each position is represented. A substitution at a conserved residue is not to be confused with a "conservative amino acid substitution," which one of ordinary skill in the art would recognize as substituting an amino acid with certain physical and/or chemical properties with another amino acid with similar properties, although a substitution at a conserved residue can include conservative and non-conservative type substitutions.

Unless otherwise specified, the following LukA subunit and LukB substitutions, deletions, and insertions (and those referred to throughout this disclosure and the appended claims) are made in reference to positions corresponding to SEQ ID NO: 28, which is the mature form of the consensus majority LukA sequence of SEQ ID NO: 1, or in reference to positions corresponding to SEQ ID NO: 29, which is the mature form of the consensus majority LukB sequence of SEQ ID NO: 15.

Protomer/Protomer Interface:

In certain aspects, a mutant staphylococcal leukocidin subunit polypeptide comprises a mutation in the LukAB protomer/protomer interface region (FIG. 1; Interface 1). In certain aspects, such mutation results in the formation of incomplete, larger leukocidin octamer rings, reduces or abolishes hemolytic activity of the toxin, or any combination thereof. In certain aspects, the mutation in the protomer/protomer interface region is at a LukA position corresponding to amino acid L61 of SEQ ID NO: 28 (FIG. 1, Inset G and FIG. 2), a LukB position corresponding to amino acid D49 of SEQ ID NO: 29 (FIG. 1, Inset H and FIG. 3; Salt Bridge E), or a combination thereof. The LukA L61 position that corresponds to L61 of SEQ ID NO: 28 is homologous with H35 of alpha-toxin and T28 of LukS-PV. Mutations at H35 of alpha-toxin reduced protomer-protomer interactions resulting in incomplete, larger octamer rings when observed by EM and abolished the hemolytic activity of the toxin. Mutations at position T28 of LukS-PV also reduced toxicity (PCT Publication No. WO 2011/112570, which is incorporated herein by reference). In certain aspects, the LukA position corresponding to amino acid L61 of SEQ ID NO: 28 is substituted with asparagine (N), glutamine (Q), or arginine (R), which can disrupt the hydrophobic pocket found within the LukAB protomer/protomer interface. In certain aspects, the LukA position corresponding to amino acid L61 of SEQ ID NO: 28 is substituted with asparagine (N). In certain aspects, the LukA position corresponding to amino acid L61 of SEQ ID NO: 28 is substituted with glutamine (Q). In certain aspects, the LukA position corresponding to amino acid L61 of SEQ ID NO: 28 is substituted with arginine (R). In certain aspects, the LukB position corresponding to amino acid D49 of SEQ ID NO: 29 is substituted with alanine (A) or lysine (K), which can disrupt the salt bridge between LukB D49, corresponding to amino acid D49 of SEQ ID NO: 29, and LukA R49, corresponding to amino acid R49 of SEQ ID NO: 28 (FIG. 1, Inset H; Salt Bridge E). In certain aspects, the LukB position corresponding to amino acid D49 of SEQ ID NO: 29 is substituted with alanine (A). In certain aspects, the LukB position corresponding to amino acid D49 of SEQ ID NO: 29 is substituted with lysine (K).

Dimer/Dimer Interface:

In certain aspects, a mutant staphylococcal leukocidin subunit polypeptide comprises a mutation in the LukAB dimer/dimer interface region (FIG. 1; Interface 2). In certain aspects, such mutation can disrupt LukAB dimer formation, can disrupt LukAB oligomerization on the surface of a eukaryotic cell, can disrupt LukAB pore formation on the surface of a eukaryotic cell, or a combination thereof. In certain aspects, the mutation in the LukAB dimer/dimer interface region is at a LukA position corresponding to amino acid D39 of SEQ ID NO: 28 (FIG. 1, Inset B and FIG. 2; Salt Bridge B), at a LukA position corresponding to amino acid D75 of SEQ ID NO: 28 (FIG. 1, Inset A and FIG. 2; Salt Bridge A), at a LukA position corresponding to amino acid K138 of SEQ ID NO: 28 (FIG. 1, Inset D and FIG. 2; Salt Bridge D), at a LukA position corresponding to amino acid D197 of SEQ ID NO: 28 (FIG. 1, Inset C and FIG. 2; Salt Bridge C), at a LukB position corresponding to amino acid K12 of SEQ ID NO: 29 (FIG. 3), at a LukB position corresponding to amino acid K19 of SEQ ID NO: 29 (FIG. 3), at a LukB position corresponding to amino acid R23 of SEQ ID NO: 29 (FIG. 1, Inset A and FIG. 3; Salt Bridge A), at a LukB position corresponding to amino acid K58 of SEQ ID NO: 29 (FIG. 1, Inset B and FIG. 3; Salt Bridge B), at a LukB position corresponding to amino acid E112 of SEQ ID NO: 29 (FIG. 1, Inset D and FIG. 3; Salt Bridge D), at a LukB position corresponding to amino acid K218 of SEQ ID NO: 29 (FIG. 1, Inset C and FIG. 3; Salt Bridge C), at a LukB position corresponding to amino acids 1-29 of SEQ ID NO: 29 (FIG. 3) and aligned for substitution with amino acids 1-29 of HlgB, or any combination thereof. In certain aspects, the LukA position corresponding to amino acid D39 of SEQ ID NO: 28 is substituted with alanine (A) or arginine (R), which can disrupt the salt bridge between LukA D39, corresponding to D39 of SEQ ID NO: 28, and LukB K58, corresponding to K58 of SEQ ID NO: 29 (FIG. 1, Inset B; Salt Bridge B). In certain aspects, the LukA position corresponding to amino acid D39 of SEQ ID NO: 28 is substituted with alanine (A). In certain aspects, the LukA position corresponding to amino acid D39 of SEQ ID NO: 28 is substituted with arginine (R). In certain aspects, the LukA position corresponding to amino acid D75 of SEQ ID NO: 28 is substituted with alanine (A), which can disrupt the salt bridge between LukA D75, corresponding to D75 of SEQ ID NO: 28, and LukB R23, corresponding to R23 of SEQ ID NO: 29 (FIG. 1, Inset A; Salt Bridge A). In certain aspects, the LukA position corresponding to amino acid K138 of SEQ ID NO: 28 is substituted with alanine (A), which can disrupt the salt bridge between LukA K138, corresponding to K138 of SEQ ID NO: 28, and LukB E112, corresponding to E112 of SEQ ID NO: 29 (FIG. 1, Inset D; Salt Bridge D). In certain aspects, the LukA position corresponding to amino acid D197 of SEQ ID NO: 28 is substituted with alanine (A) or lysine (K), which can disrupt the salt bridge between LukA D197, corresponding to D197 of SEQ ID NO: 28, and LukB K218, corresponding to K218 of SEQ ID NO: 29 (FIG. 1, Inset C; Salt Bridge C). In certain aspects, the LukA position corresponding to amino acid D197 of SEQ ID NO: 28 is substituted with alanine (A). In certain aspects, the LukA position corresponding to amino acid D197 of SEQ ID NO: 28 is substituted with lysine (K). In certain aspects, the LukB position corresponding to amino acid K12 of SEQ ID NO: 29 is substituted with alanine (A). In certain aspects, the LukB position corresponding to amino acid K19 of SEQ ID NO: 29 is substituted with alanine (A). In certain aspects, the LukB position corresponding to amino acid R23 of SEQ ID NO: 29 is substituted with alanine (A) or glutamate (E), which can disrupt the salt bridge between LukB R23, corresponding to R23 of SEQ ID NO :29, and LukA D75, corresponding to D75 of SEQ ID NO: 28 (FIG. 1, Inset A; Salt Bridge A). In certain aspects, the LukB position corresponding to amino acid R23 of SEQ ID NO: 29 is substituted with alanine (A). In certain aspects, the LukB position corresponding to amino acid R23 of SEQ ID NO: 29 is substituted with glutamate (E). In certain aspects, the LukB position corresponding to amino acid K58 of SEQ ID NO: 29 is substituted with alanine (A) or glutamate (E), which can disrupt the salt bridge between LukB K58, corresponding to K58 of SEQ ID NO: 29, and LukA D39, corresponding to D39 of SEQ ID NO: 28 (FIG. 1, Inset B; Salt Bridge B). In certain aspects, the LukB position corresponding to amino acid K58 of SEQ ID NO: 29 is substituted with alanine (A). In certain aspects, the LukB position corresponding to amino acid K58 of SEQ ID NO: 29 is substituted with glutamate (E). In certain aspects, the LukB position corresponding to amino acid E112 of SEQ ID NO: 29 is substituted with alanine (A), which can disrupt the salt bridge between LukB E112, corresponding to E112 of SEQ ID NO: 29, and LukA K138, corresponding to K138 of SEQ ID NO: 28 (FIG. 1, Inset D; Salt Bridge D). In certain aspects, the LukB position corresponding to amino acid K218 of SEQ ID NO: 29 is substituted with alanine (A), which can disrupt the salt bridge between LukB K218, corresponding to K218 of SEQ ID NO: 29, and LukA D197, corresponding to D197 of SEQ ID NO: 28 (FIG. 1, Inset C; Salt Bridge C). In certain aspects, the LukB positions corresponding to amino acids K12, K19, and R23 of SEQ ID NO: 29 are substituted with alanine (A), alanine (A), and alanine (A) or glutamate (E), respectively, which can at least disrupt the salt bridge between LukB R23, corresponding to R23 of SEQ ID NO: 29, and LukA D75, corresponding to D75 of SEQ ID NO: 28 (FIG. 1, Inset A; Salt Bridge A). In certain aspects, the LukB positions corresponding to amino acids K12, K19, and R23 of SEQ ID NO: 29 are substituted with alanine (A), alanine (A), and alanine (A), respectively. In certain aspects, the LukB positions corresponding to amino acids K12, K19, and R23 of SEQ ID NO: 29 are substituted with alanine (A), alanine (A), and glutamate (E), respectively. In certain aspects the LukB position corresponding to amino acids 1-29 of SEQ ID NO: 29 is substituted with acids 1-29 of HlgB, as more fully described herein and referred to as "LukB-HlgB", which can reduce LukAB toxicity and generate an antibody response to the N terminal residues of HlgB.

Membrane-Binding Cleft Region:

In certain aspects, a mutant staphylococcal leukocidin subunit polypeptide comprises a mutation in the LukB membrane-binding cleft region (FIG. 1). In certain aspects, such mutation can disrupt the interaction of the LukB subunit with the polar head groups of the lipid bilayer of a eukaryotic cell. In certain aspects, the mutation in the LukB membrane-binding cleft region is at a LukB position corresponding to amino acid H180 of SEQ ID NO: 29, at a LukB position corresponding to amino acid E197 of SEQ ID NO: 29, at a LukB position corresponding to amino acid R203 of SEQ ID NO: 29, or any combination thereof (FIG. 1, Inset F). In certain aspects, the LukB position corresponding to H180 of SEQ ID NO: 29 is substituted with alanine (A). In certain aspects, the LukB position corresponding to E197 of SEQ ID NO: 29 is substituted with alanine (A). In certain aspects, the LukB position corresponding to R203 of SEQ ID NO: 29 is substituted with alanine (A). In certain aspects, the LukB positions corresponding to H180, E197, and R203 of SEQ ID NO: 29 are substituted with alanine (A).

Pore Forming Region:

In certain aspects, a mutant staphylococcal leukocidin subunit polypeptide comprises a mutation in the LukB pore forming region (FIG. 1). In certain aspects, such mutation can obstruct the cytoplasmic edge of the LukAB pore formed on the surface of a eukaryotic cell, thereby obstructing pore formation. In certain aspects, the mutation in the LukB pore forming region comprises deletion of the amino acids corresponding to F125 to T133 of SEQ ID NO: 29 (FIG. 1, Inset E). In certain aspects, a flexible amino acid insertion, e.g., one, two, three, four, five, or more glycine (G) residues, can be inserted after the amino acid at a position corresponding to D124 of SEQ ID NO: 29.

In certain aspects, a mutant LukA subunit, a mutant LukB subunit, or a mutant LukAB dimer, disclosed anywhere herein, is less toxic in a neutrophil toxicity assay compared to the corresponding wild-type leukocidin subunit. In certain aspects, a mutant LukA subunit, a mutant LukB subunit, or a mutant LukAB dimer, disclosed anywhere herein, exhibits >50%, >60%, >70%, >80%, >90%, or >95% loss of activity. In some aspects, a loss in toxicity/activity is achieved without negatively impacting immunogenicity.

LukA Polypeptides

Disclosed herein is an isolated mutant staphylococcal LukA subunit polypeptide comprising, consisting of, or consisting essentially of a wild-type staphylococcal LukA subunit except for having one or more mutations, e.g., amino acid substitutions, deletions, or a combination thereof at conserved residues in the LukA subunit. In certain aspects, the one or more mutations comprises 1, 2, 3, 4, 5, 6, 7, 8, 9, 10, 11, 12, 13, 14, 15, 16, or 17 amino acid substitutions, deletions, insertions, or a combination thereof. In certain aspects, the amino acid substitutions, deletions, insertions or a combination thereof are at conserved residues in the LukAB protomer/protomer interface region (also referred to as Interface 1 herein; FIG. 1), the dimer/dimer interface region (also referred to as Interface 2 herein; FIG. 1), or any combination thereof. In certain aspects, the ability of the LukA subunit to form dimers, to oligomerize, to form pores on the surface of eukaryotic cells, or any combination thereof is disrupted. Thus, in certain aspects, the toxicity of the mutant LukA subunit relative to the corresponding wild-type LukA subunit is reduced. In certain aspects, the substitutions, deletions, insertions or a combination thereof do not significantly reduce the immunogenicity of the mutant LukA subunit or the mutant LukAB dimer relative to the corresponding wild-type leukocidin subunit or dimer.

The alignment shown in FIG. 2 contains a polypeptide amino acid sequence of a consensus majority LukA sequence (SEQ ID NO: 1, top) and the wild-type LukA polypeptide amino acid sequences from 13 different representative strains of S. aureus to which the majority sequence corresponds (SEQ ID NOs: 2-14).

The N-terminal 27 amino acid residues in each of SEQ ID NOs: 1-14 represent the native secretion/signal sequence. One of ordinary skill in the art would understand how to determine the sequence of the mature form LukA without a signal sequence from the immature forms in SEQ ID NOs: 1-14 by omitting the first 27 amino acid residues. SEQ ID NO: 28 (shown at bottom of the alignment illustrated in FIG. 2) is a mature LukA sequence derived from the consensus majority LukA sequence of SEQ ID NO: 1. SEQ ID NOs: 32-44 are mature LukA sequences, corresponding to SEQ ID NOs: 2-14, respectively. For example, in certain aspects, the wild-type LukA sequence is SEQ ID NO: 2 or its mature form of SEQ ID NO: 32, which are LukA polypeptides native to the Newman strain of S. aureus:

MKNKKRVLIASSLSCAILLLSAATTQANSAHKDSQDQNK

KEHVDKSQQKDKRNVTNKDKNSTAPDDIGKNGKITKRTET

VYDEKTNILQNLQFDFIDDPTYDKNVLLVKKQGSIHSNLKF

ESHKEEKNSNWLKYPSEYHVDFQVKRNRKTEILDQLPKNKI

STAKVDSTFSYSSGGKFDSTKGIGRTSSNSYSKTISYNQQNY

DTIASGKNNNWHVHWSVIANDLKYGGEVKNRNDELLFYR

NTRIATVENPELSFASKYRYPALVRSGFNPEFLTYLSNEKSN

EKTQFEVTYTRNQDILKNRPGIHYAPPILEKNKDGQRLIVTY

EVDWKNKTVKVVDKYSDDNKPYKEG (SEQ ID NO: 2; 27 amino acid signal sequence is bold underlined; remaining sequence is SEQ ID NO: 32).

In certain aspects, the wild-type LukA subunit from which a mutant polypeptide is derived comprises an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, and SEQ ID NO: 44.

LukB Polypeptides

Also disclosed is an isolated mutant staphylococcal LukB subunit polypeptide comprising, consisting of, or consisting essentially of a wild-type staphylococcal LukB subunit except for having one or more mutations, e.g., amino acid substitutions, deletions, insertions, or a combination thereof at conserved residues in the LukB subunit. In certain aspects, the one or more mutations comprises 1, 2, 3, 4, 5, 6, 7, 8, 9, 10, 11, 12, 13, 14, 15, 16, or 17 amino acid substitutions, deletions, insertions or a combination thereof. In certain aspects, the amino acid substitutions, deletions, insertions, or a combination thereof are at conserved residues in the LukAB protomer/protomer interface region (also referred to as Interface 1 herein; FIG. 1), the dimer/dimer interface region (also referred to as Interface 2 herein; FIG. 1), the LukB membrane-binding cleft region (FIG. 1), the LukB pore forming region (FIG. 1), or any combination thereof. In certain aspects, the ability of the LukB subunit to form dimers, to oligomerize, to form pores on the surface of eukaryotic cells, or any combination thereof is disrupted. Thus, in certain aspects, the toxicity of the mutant LukB subunit relative to the corresponding wild-type LukB subunit is reduced. In certain aspects, the substitutions, deletions, insertions or a combination thereof do not significantly reduce the immunogenicity of the mutant LukB subunit or the mutant LukAB dimer relative to the corresponding wild-type leukocidin subunit or dimer.

The alignment illustrated in FIG. 3 contains a polypeptide amino acid sequence of a consensus majority LukB sequence (SEQ ID NO: 15) and the wild-type LukB polypeptide amino acid sequences from 12 different representative strains of S. aureus to which the majority sequence corresponds (SEQ ID NOs: 16-27).

The N-terminal 29 amino acid residues in each of SEQ ID NOs: 15, 16, and 18-27 represent the native secretion/signal sequence (SEQ ID NO: 17 LukB COL does not contain a signal sequence). One of ordinary skill in the art would understand how to determine the sequence of the mature form LukB without a signal sequence from the immature forms in SEQ ID NOs: 16 and 18-27 by omitting the first 29 amino acid residues. SEQ ID NO: 29 (shown at the bottom of the alignment illustrated in FIG. 3) is a mature LukB sequence derived from the majority LukB sequence of SEQ ID NO: 15. SEQ ID NOs: 45-55 are mature LukB sequences corresponding to SEQ ID NOs: 16 and 18-27, respectively. For example, in certain aspects, the wild-type LukB sequence is SEQ ID NO: 27 or the mature form of SEQ ID NO: 55, which is the LukB polypeptide native to the Newman strain of S. aureus:

MIKQLCKNITICTLALSTTFTVLPATSFAKINSEIKQVSEK

NLDGDTKMYTRTATTSDSQKNITQSLQFNFLTEPNYDKETV

FIKAKGTIGSGLRILDPNGYWNSTLRWPGSYSVSIQNVDDN

NNTNVTDFAPKNQDESREVKYTYGYKTGGDFSINRGGLTG

NITKESNYSETISYQQPSYRTLLDQSTSHKGVGWKVEAHLIN

NMGHDHTRQLTNDSDNRTKSEIFSLTRNGNLWAKDNFTPK

DKMPVTVSEGFNPEFLAVMSHDKKDKGKSQFVVHYKRSM

DEFKIDWNRHGFWGYWSGENHVDKKEEKLSALYEVDWKT

HNVKFVKVLNDNEKK (SEQ ID NO: 27; 29 amino acid signal sequence is bold underlined; remaining sequence is SEQ ID NO: 55).

In certain aspects, a mutant staphylococcal leukocidin subunit polypeptide comprises a substitution of the first 29 residues of LukB with HlgB (LukB-HlgB) (SEQ ID NO: 58).

In certain embodiments, the wild-type LukB subunit comprises an amino acid sequence selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, and SEQ ID NO: 55.

Also disclosed is a polypeptide complex comprising any of the mutant leukocidin subunits as described herein. The one or more substitutions, deletions, or combination thereof can be any amino acid(s) that maintains structure and conformation of the mutant leukocidin subunit complex.

In another aspect, the mutant staphylococcal leukocidin subunit (e.g., LukA or LukB, or both), as described herein, can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenylalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, phage T7 gene 10 leader, an avidin/streptavidin/STREP-TAG® complex, trpE, chloramphenicol acetyltransferase, lacZ (β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of LukA and/or LukB polypeptides as described herein from a host cell or any useful immunogenic sequence, including but not limited to sequences that encode a T-cell epitope of a microbial pathogen, or other immunogenic proteins and/or epitopes.

In some aspects, the mutant staphylococcal leukocidin subunit (e.g., LukA or LukA, or both), attached to a heterologous polypeptide, as described herein, can include a peptide linker sequence joining sequences that comprise two or more peptide regions. Suitable peptide linker sequences can be chosen based on their ability to adopt a flexible, extended conformation, or a secondary structure that could interact with joined epitopes, or based on their ability to increase overall solubility of the fusion polypeptide, or based on their lack of electrostatic or water-interaction effects that influence joined peptide regions.

In some aspects, the mutant staphylococcal leukocidin subunit (e.g., LukA or LukB, or both), as described herein, is isolated. An "isolated" polypeptide is one that has been removed from its natural milieu. The term "isolated" does not connote any particular level of purification. Recombinantly produced mutant staphylococcal leukocidin subunit (e.g., LukA or LukB, or both), as described herein, expressed in non-native host cells is considered isolated for purposes of the disclosure, as is the polypeptide which have been separated, fractionated, or partially or substantially purified by any suitable technique, including by filtration, chromatography, centrifugation, and the like.

Production of the mutant staphylococcal leukocidin subunit (e.g., LukA or LukB, or both), as described herein, can be achieved by culturing a host cell comprising a polynucleotide which operably encodes the polypeptide of the disclosure, and recovering the polypeptide. Determining conditions for culturing such a host cell and expressing the polynucleotide are generally specific to the host cell and the expression system and are within the knowledge of one of skill in the art. Likewise, appropriate methods for recovering the polypeptide of the disclosure are known to those in the art, and include, but are not limited to, chromatography, filtration, precipitation, or centrifugation.

Polynucleotides

The disclosure is further directed to an isolated polynucleotide comprising a nucleic acid encoding an isolated mutant staphylococcal leukocidin subunit polypeptide subunit comprising, consisting of, or consisting essentially of a wild-type staphylococcal LukA subunit, a wild-type staphylococcal LukB subunit, or a wild-type staphylococcal LukAB dimer, except for having one or more mutations as described herein, which reduce toxicity of the mutant leukocidin subunit relative to the corresponding wild-type leukocidin subunit. In certain aspects, the substitutions, deletions, or a combination thereof do not significantly reduce the immunogenicity of the mutant LukA subunit, mutant LukB subunit, or the mutant LukAB dimer relative to the corresponding wild-type leukocidin subunit or dimer.

For example the nucleotide sequence SEQ ID NO: 30 encodes the LukA polypeptide of *S. aureus* (Newman) of SEQ ID NO: 2 and the nucleotide sequence SEQ ID NO: 31 encodes the LukB polypeptide of *S. aureus* (Newman) of SEQ ID NO: 27.

In certain aspects, the isolated polynucleotide as described herein further comprises non-coding regions such as promoters, operators, or transcription terminators as described elsewhere herein. In some aspects, the disclosure is directed to the polynucleotide as described herein, and further comprising a heterologous nucleic acid. The heterologous nucleic acid can, in some aspects, encode a heterologous polypeptide fused to the polypeptide as described herein. For example, the isolated polynucleotide as described herein can comprise additional coding regions encoding, e.g., a heterologous polypeptide fused to the polypeptide as described herein, or coding regions encoding heterologous polypeptides separate from the polypeptide as described herein such as, but not limited to, selectable markers, additional immunogens, immune enhancers, and the like.

Also provided are expression constructs, vectors, and/or host cells comprising the polynucleotides described herein.

An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. In certain aspects of the disclosure a polynucleotide is "recombinant." Isolated polynucleotides or nucleic acids according to the disclosure further include such molecules produced synthetically. The relative degree of purity of a polynucleotide or polypeptide described herein is easily determined by well-known methods.

Codon Optimization

Also included within the scope of the disclosure are genetically engineered polynucleotides encoding the mutant staphylococcal leukocidin subunit (e.g., LukA or LukB, or both), as described herein. Modifications of nucleic acids encoding the mutant staphylococcal leukocidin subunit e.g., (LukA or LukB, or both), as described herein, can readily be accomplished by those skilled in the art, for example, by oligonucleotide-directed site-specific mutagenesis or de novo nucleic acid synthesis.

Some aspects disclose an isolated polynucleotide comprising a nucleic acid fragment, which encodes the mutant staphylococcal leukocidin subunit (e.g., LukA or LukB, or both), as described herein, where the coding region encoding the polypeptide has been codon-optimized. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence of the coding region. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 1

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

It is to be appreciated that any polynucleotide that encodes a polypeptide in accordance with the disclosure falls within the scope of this disclosure, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms.

Different factors have been proposed to contribute to codon usage preference, including translational selection, GC composition, strand-specific mutational bias, amino acid conservation, protein hydropathy, transcriptional selection and even RNA stability. One factor that determines codon usage is mutational bias that shapes genome GC composition. This factor is most significant in genomes with extreme base composition: species with high GC content (e.g., gram positive bacteria). Mutational bias is responsible not only for intergenetic difference in codon usage but also for codon usage bias within the same genome (Ermolaeva M, Curr. Issues Mol. Biol. 3(4):91-97, 2001).

Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The present disclosure relates to a polynucleotide comprising a codon-optimized coding region which encodes the mutant staphylococcal leukocidin subunit polypeptide (e.g., LukA or LukB, or both), as described herein. The codon usage is adapted for optimized expression in a given prokaryotic or eukaryotic host cell.

Codon-optimized polynucleotides are prepared by incorporating codons preferred for use in the genes of a given species into the DNA sequence. For example, SEQ ID NO: 56 is an *E. coli* codon optimized nucleotide sequence encoding the LukA polypeptide subunit from the Newman strain of *S. aureus*. SEQ ID NO: 57 is an *E. coli* codon optimized nucleotide sequence encoding the LukB polypeptide subunit from the Newman strain of *S. aureus*. Also provided are polynucleotide expression constructs, vectors, host cells comprising polynucleotides comprising codon-optimized coding regions which encode the mutant staphylococcal leukocidin subunit polypeptide (e.g., LukA or LukB, or both), as described herein.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited Oct. 12, 2011), and these tables can be adapted in a number of ways. (Nakamura, Y., et al., "Codon usage tabulated from the international DNA sequence databases: status for the year 2000" Nucl. Acids Res. 28:292, 2000).

By utilizing available tables, one of ordinary skill in the art can apply the frequencies to any given polypeptide sequence, and produce a nucleic acid fragment of a codon-optimized coding region which encodes a desired polypeptide, but which uses codons optimal for a given species. For example, in some aspects of the disclosure, the coding region is codon-optimized for expression in *E. coli*.

DNA Synthesis

A number of options are available for synthesizing codon optimized coding regions designed by any of the methods described above, using standard and routine molecular biological manipulations well known to those of ordinary skill in the art. In addition, gene synthesis is readily available commercially.

Vectors and Expression Systems

Further disclosed is a vector comprising the polynucleotide as described herein. The term "vector," as used herein, refers to e.g., any of a number of nucleic acids into which a desired sequence can be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct made up of genetic material (i.e., nucleic acids), in which the genetic material is extrachromosomal and in some instances, replicates autonomously. A polynucleotide described herein can be in a circular or linearized plasmid or in any other sort of vector. Procedures for inserting a nucleotide sequence into a vector, e.g., an expression vector, and transforming or transfecting into an appropriate host cell and cultivating under conditions suitable for expression are generally known in the art.

In accordance with one aspect of the disclosure, provided is a vector comprising a nucleic acid sequence encoding the mutant staphylococcal leukocidin subunit (e.g., LukA or LukB, or both), as described herein. In certain aspects the vector is an expression vector capable of expressing the mutant staphylococcal leukocidin subunit (e.g., LukA or LukB, or both), as described herein in a suitable host cell. The term "expression vector" refers to a vector that is capable of expressing the polypeptide described herein, i.e., the vector sequence contains the regulatory sequences required for transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain aspects, the host cell is a bacterium, e.g., E. coli.

Host cells are genetically engineered (infected, transduced, transformed, or transfected) with vectors of the disclosure. Thus, one aspect of the disclosure is directed to a host cell comprising a vector which contains the polynucleotide as describe herein. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., E. coli), transformed with recombinant bacteriophage DNA, plasmid DNA or cosmid DNA. In some aspects, the plasmids used with E. coli use the T7 promoter-driven system regulated by the LacI protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiX174, pBluescript SK, pbsks, pNH8A, pNH16a, pNH18A, pNH46A (Stratagene), ptrc99a, pKK223-3, pKK243-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences which can be operably joined to an inserted nucleotide sequence encoding the mutant staphylococcal leukocidin subunit (e.g., LukA or LukB, or both), as described herein. As used herein, the term "regulatory sequences" means nucleotide sequences which are necessary for or conducive to the transcription of an inserted sequence coding the mutant staphylococcal leukocidin subunit (e.g., LukA or LukB, or both), as described herein by a host cell and/or which are necessary for or conducive to the translation by a host cell of the resulting transcript into the desired mutant leukocidin subunit (e.g., LukA or LukB, or both). Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of E. coli, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, the polynucleotide as described herein can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are confirmed using restriction mapping, DNA sequence analysis, and/or PCR analysis. Bacterial cells harboring the correct plasmid can be stored as cell banks.

Immunogenic and Pharmaceutical Compositions

Further disclosed are compositions, e.g., immunogenic or pharmaceutical compositions, that contain an effective amount of the mutant staphylococcal leukocidin subunit (e.g., LukA or LukB, or both), as described herein, or a polynucleotide encoding the polypeptide of the disclosure. Compositions as described herein can further comprise additional immunogenic components, e.g., as a multivalent vaccine, as well as carriers, excipients or adjuvants.

Compositions as described herein can be formulated according to known methods. Suitable preparation methods are described, for example, in *Remington's Pharmaceutical Sciences*, 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the disclosure can be administered directly to the subject. The subjects to be treated can be animals; in particular, human subjects can be treated.

Carriers that can be used with compositions of the disclosure are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions as described herein further include one or more adjuvants, a substance added to an immunogenic composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant. The term "immunogenic carrier" as used herein refers to a first moiety, e.g., a polypeptide or fragment, variant, or derivative thereof which enhances the immunogenicity of a second polypeptide or fragment, variant, or derivative thereof.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or Th2 response into a primarily cellular, or Th1 response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions described herein include, but are not limited to: inert carriers, such as alum, bentonite, latex, and acrylic particles; incomplete Freund's adjuvant, complete Freund's adjuvant; aluminum-based salts such as aluminum hydroxide; ALHYDROGEL® ($Al(OH)_3$)); aluminum phosphate ($AlPO_4$); calcium-based salts; silica; any TLR biological ligand(s); IDC-1001 (also known as GLA-SE; glucopyranosyl lipid adjuvant stable emulsion) (Coler et al., PLoS One, 2010. 5(10): p. e13677; Coler et al., PLoS One, 2011. 6(1): p. e16333); CpG (Mullen et al., PLoS One, 2008. 3(8): p. e2940), or any combination thereof. The amount of adjuvant, how it is formulated, and how it is administered all parameters which are well within the purview of a person of ordinary skill in the art.

In some aspects, a composition of the disclosure further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, the polypeptide described herein can be incorporated as part of a liposome or other particle, or can be delivered in conjunction with a liposome. Liposomes for use in accordance with the disclosure can be formed from standard vesicle-forming lipids, which generally include neutral and negatively charged phospholipids and a sterol, such as cholesterol. A composition comprising a liposome or other particulate suspension as well as the polypeptide as described herein can be administered intravenously, locally, topically, etc. in a dose which varies according to, inter alia, the manner of administration, the polypeptide being delivered, and the stage of the disease being treated.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, the polypeptide as described herein, often at a concentration of 25%-75%.

For aerosol or mucosal administration, the polypeptide as described herein can be supplied in finely divided form, optionally along with a surfactant and, propellant and/or a mucoadhesive, e.g., chitosan. The surfactant must, of course, be pharmaceutically acceptable, and in some aspects soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some aspects 0.25-5% by weight. The balance of the composition is ordinarily propellant, although an atomizer can be used in which no propellant is necessary and other percentages are adjusted accordingly. In some aspects, the immunogenic polypeptides can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

The disclosure is also directed to a method of producing the composition according to the disclosure. In some aspects, the method of producing the composition comprises (a) isolating a polypeptide according to the disclosure; and (b) adding an adjuvant, carrier and/or excipient to the isolated polypeptide. Some aspects disclose further combining the polypeptide with other staphylococcal antigens.

Some aspects include a multivalent vaccine. A multivalent vaccine of the present disclosure comprises the mutant staphylococcal leukocidin subunit (e.g., LukA or LukB, or both), as described herein, or a polynucleotide encoding one or both subunits, and one or more additional immunogenic components. Such components can be additional immunogens of the same infectious agent, e.g., *S. aureus,* or from other staphylococci, or can be immunogens derived from other infectious agents which can be effectively, conveniently, or economically administered together. In certain aspects, the mutant staphylococcal leukocidin subunit (e.g., LukA or LukB, or both), as described herein, can be combined with other toxins or other virulent component-based vaccines to make a broad toxin-based multivalent vaccine capable of targeting multiple bacterial virulence determinants. In other aspects, the mutant staphylococcal leukocidin subunit (e.g., LukA or LukB, or both), as described herein, can be fused to other immunogenic, biologically significant, or protective epitope containing polypeptides to generate a multivalent vaccine in a single chain and induce an immune response against multiple antigens. In yet another embodiment, the mutant staphylococcal leukocidin subunit (e.g., LukA or LukB, or both), as described herein, can be fused to one or more T cell epitopes to induce T cell immunity along with anti leukocidin antibodies.

Methods of Treatment/Prevention and Regimens

Also provided is a method of treating or preventing *Staphylococcus* infection, e.g., *S. aureus* infection or treating or preventing a disease caused by *Staphylococcus,* e.g., *S. aureus* in a subject, comprising administering to a subject in need thereof a composition as described herein comprising the mutant staphylococcal leukocidin subunit (e.g., LukA or LukB, or both), as described herein, or polynucleotides, vectors, or host cells encoding same. In certain aspects, the subject is an animal, e.g., a vertebrate, e.g., a mammal, e.g., a human. Some aspects include a method of inducing an immune response against a *S. aureus* strain, comprising administering to a subject in need of said immune response an effective amount of a composition as described herein comprising the mutant staphylococcal leukocidin subunit (e.g., LukA or LukB, or both), as described herein, or polynucleotides, vectors, or host cells encoding same.

In some aspects, a subject is administered a composition as described herein comprising the mutant staphylococcal leukocidin subunit (e.g., LukA or LukB, or both), as described herein, or polynucleotides, vectors, or host cells encoding same prophylactically, e.g., as a prophylactic vaccine, to establish or enhance immunity to *Staphylococcus,* e.g., *S. aureus,* in a healthy animal prior to potential or actual exposure to *Staphylococcus,* e.g., *S. aureus* or contraction of a *Staphylococcus*-related symptom, thus preventing disease, alleviating symptoms, reducing symptoms, or reducing the severity of disease symptoms. In one embodiment the disease is a respiratory disease, e.g., pneumonia. Other diseases or conditions to be treated or prevented include, but are not limited to, bacteremia, sepsis, skin infections, wound infections, endocarditis, bone and joint infections, osteomyelitis, and/or meningitis. One or more compositions, polypeptides, polynucleotides, vectors, or host cells as described herein can also be used to treat a subject already exposed to *Staphylococcus,* e.g., *S. aureus,* or already suffering from a *Staphylococcus* related symptom to further stimulate the immune system of the animal, thus reducing or eliminating the symptoms associated with that exposure. As defined herein, "treatment of an animal" refers to the use of one or more compositions, polypeptides, polynucleotides, vectors, or host cells of the disclosure to prevent, cure, retard, or reduce the severity of *S. aureus* symptoms in an animal, and/or result in no worsening of *S. aureus* symptoms over a specified period of time. It is not required that any composition, polypeptide, polynucleotide, a vector, or a host cell as described herein provides total protection against a staphylococcal infection or totally cure or eliminate all *Staphylococcus* related symptoms.

As used herein, "a subject in need of therapeutic and/or preventative immunity" refers to a subject in which it is desirable to treat, i.e., to prevent, cure, retard, or reduce the severity of *Staphylococcus* related symptoms, or result in no worsening of *Staphylococcus* related symptoms over a specified period of time. As used herein, "a subject in need of the immune response" refers to a subject for which an immune response(s) against any of LukAB-expressing Staphylococcal strains is desired.

Treatment with pharmaceutical compositions comprising an immunogenic composition, polypeptide or polynucleotide as described herein can occur separately or in conjunction with other treatments, as appropriate.

In therapeutic applications, a composition, polypeptide or polynucleotide of the disclosure is administered to a patient in an amount sufficient to elicit an effective innate, humoral or cellular response, or both, to the *S. aureus* LukAB-derived polypeptide to cure or at least partially arrest symptoms or complications.

An amount adequate to accomplish this is defined as "therapeutically effective dose" or "unit dose." Amounts effective for this use will depend on, e.g., the polypeptide or polynucleotide composition, the manner of administration, the stage and severity of the disease being treated, the weight and general state of health of the patient, and the judgment of the prescribing physician, but generally range for the initial immunization for polypeptide vaccines is (that is for therapeutic or prophylactic administration) from about e.g., 0.1 µg to about 5000 µg of polypeptide, depending upon the patient's response and condition by measuring, for example, antibody levels in the patient's blood. In some aspects, a priming dose is followed by a boosting dose over a period of time.

In non-limiting aspects of the disclosure, an effective amount of a composition as disclosed herein produces an elevation of antibody titer to at least 2, 5, 10, 50, 100, 500, 1000, 5000, $10^4$, $5 \times 10^4$, or $10^5$ times the antibody titer prior to administration.

In alternative aspects, generally for humans an initial immunization (that is for therapeutic or prophylactic administration) is administered followed by boosting dosages in the same dose range pursuant to a boosting regimen over weeks to months depending upon the patient's response and condition by measuring the antibody or T lymphocyte response in the patient's blood.

It must be kept in mind that the polypeptides and compositions as described herein can generally be employed in serious disease states, that is, life-threatening or potentially life threatening situations. In such cases, in view of the minimization of extraneous substances and the relative nontoxic nature of the polypeptides, it is possible and can be felt desirable by the treating physician to administer substantial excesses of these polypeptide compositions.

For therapeutic use, administration should begin at the first sign of *S. aureus* infection or risk factors. In certain aspects, the initial dose is followed by boosting doses until, e.g., symptoms are substantially abated and for a period thereafter. In frequent infection, loading doses followed by boosting doses can be required.

In certain aspects, the composition as described herein is delivered to a subject by methods described herein, thereby achieving an effective immune response, and/or an effective therapeutic or preventative immune response. Any mode of administration can be used so long as the mode results in the delivery and/or expression of the desired polypeptide in the desired tissue, in an amount sufficient to generate an immune response to *Staphylococcus*, e.g., *S. aureus*, and/or to generate a prophylactically or therapeutically effective immune response to *Staphylococcus*, e.g., to *S. aureus*, in an animal in need of such response. According to the disclosed methods, a composition described herein can be administered by mucosal delivery, transdermal delivery, subcutaneous injection, intravenous injection, oral administration, pulmonary administration, intramuscular (i.m.) administration, or via intraperitoneal injection. Other suitable routes of administration include, but not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired polypeptide in an amount sufficient to generate an immune response to *Staphylococcus*, e.g., *S. aureus*, and/or to generate a prophylactically or therapeutically effective immune response to *Staphylococcus*, e.g., *S. aureus*, in an animal in need of such response. Administration as described herein can be by e.g., needle injection, or other delivery or devices known in the art.

In some aspects, a composition comprising the mutant staphylococcal leukocidin subunit (e.g., LukA or LukB, or both), as described herein, or polynucleotides, vectors, or host cells encoding same, stimulate an antibody response or a cell-mediated immune response sufficient for protection of an animal against *Staphylococcus*, e.g., *S. aureus* infection. In other aspects, a composition comprising the mutant staphylococcal leukocidin subunit (e.g., LukA or LukB, or both), as described herein, or polynucleotides, vectors, or host cells encoding same, stimulate both a humoral and a cell-mediated response, the combination of which is sufficient for protection of an animal against *Staphylococcus*, e.g., *S. aureus* infection. In some aspects, a composition comprising the mutant staphylococcal leukocidin subunit (e.g., LukA or LukB, or both), as described herein, or polynucleotides, vectors, or host cells encoding same, further stimulates an innate, an antibody, and/or a cellular immune response.

In some aspects, a composition comprising the mutant staphylococcal leukocidin subunit (e.g., LukA or LukB, or both), as described herein, or polynucleotides, vectors, or host cells encoding same, induce antibody responses to *S. aureus* leukotoxins. In certain aspects, components that induce T cell responses (e.g., T cell epitopes) are combined with components such as the polypeptides as described herein that primarily induce an antibody response.

Further disclosed is a method for generating, enhancing, or modulating a protective and/or therapeutic immune response to *S. aureus* infection in a subject, comprising administering to a subject in need of therapeutic and/or preventative immunity one or more of the compositions as described herein.

The compositions as described herein can be administered to an animal at any time during the lifecycle of the animal to which it is being administered. In humans, administration of the composition as described herein can, and often advantageously occurs while other vaccines are being administered, e.g., as a multivalent vaccine as described elsewhere herein.

Furthermore, the composition as described herein can be used in any desired immunization or administration regimen; e.g., in a single administration or alternatively as part of periodic vaccination regimes such as annual vaccinations, or as in a prime-boost regime in which composition or polypeptide or polynucleotide of the disclosure is administered either before or after the administration of the same or of a different polypeptide or polynucleotide. Recent studies have indicated that a prime-boost protocol is often a suitable method of administering vaccines. In a prime-boost protocol, one or more compositions as described herein can be utilized in a "prime boost" regimen. An example of a "prime boost" regimen can be found in Yang, Z. et al. J. Virol. 77:799-803, 2002, which is incorporated herein by reference in its entirety.

Infections to be treated include, but are not limited to a localized or systemic infection of skin, soft tissue, blood, or an organ or an auto-immune disease. Specific diseases or conditions to be treated or prevented include, but are not limited to, respiratory diseases, e.g., pneumonia, sepsis, skin infections, wound infections, endocarditis, bone and joint infections, osteomyelitis, and/or meningitis.

Immune Correlates

A number of animal models for *S. aureus* infection are known in the art, and can be used with the methods disclosed herein without undue experimentation. For example, a hamster model of methicillin-resistant *Staphylococcus aureus* (MRSA) pneumonia has been described for the testing of antimicrobials. (Verghese A. et al., Chemotherapy. 34:497-503 (1988), Kephart PA. et al. J Antimicrob Chemother. 21:33-9, (1988)). Further, a model of *S. aureus*-induced pneumonia in adult, immunocompetent C57BL/6J mice is described, which closely mimics the clinical and pathological features of pneumonia in human patients. (Bubeck-Wardenburg J. et al., Infect Immun. 75:1040-4 (2007)). Additionally, virulence has been tested in a rat model of *S. aureus* pneumonia as described in McElroy et al. (McElroy MC. et al., Infect Immun. 67:5541-4 (1999)). Finally, a standardized and reproducible model of MRSA-induced septic pneumonia to evaluate new therapies was established in sheep. (Enkhbaatar P. et al., Shock. 29(5):642-9 (2008)).

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No: 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt, I., Brostoff, J. and Male D., Immunology, 6$^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

EXAMPLES

Example 1: Structural Analysis and Determination of Candidate Sites for Mutagenesis Octamerization of secreted LukAB dimers to form pores on the surface of target cells is critical to its function. Therefore, mutations were designed that would disrupt the heterodimer interface and select for attenuated yet highly immunogenic LukAB toxoids. Towards this end, the salt bridges were mutated at the LukAB protomeric (protomer-protomer) and the heterodimeric (dimer-dimer) interfaces called interface 1 & 2, respectively (FIG. 1). At Interface 1, the residues LukB D49 and LukA R49 within the salt bridge were mutated to LukB D49A and LukA R49E, to introduce repulsive electrostatic interactions. Similarly, at interface 2, K138A, D197A, D75A, D39A mutations were made on LukA to disrupt salt bridge interactions with LukB residues E112, K218, R23, and K58A, respectively. Numbering was based on 4tw1 structure as disclosed in Badarau A. et al., J. Biol. Chem. 290(1): 142-56 (2015) and available at the https world wide web internet site "rcsb.org/structure/4TW1". Additionally, LukA D197K and LukB R23E and K58E mutations were designed to introduce repulsive electrostatic interactions. Other than salt bridges, mutations were also designed to affect toxicity (LukA L61N/Q/R) based on homology to H35 of alpha toxin and T28 of LukS PV. Homologous residues within the cleft in the rim domain of both alpha toxin and LukF were also targeted, namely, LukB H180A, E197A and R203A, as they have been shown to bind to the polar head groups of the lipid bilayer. Additionally, mutations replacing LukB residues 125-133 (FSINRG-GLT) were also designed to perturb the contact sites on the cytoplasmic edge of the pore.

Example 2: Generation of LukA and LukB Mutants

LukA and LukB mutants were selected based on structural analysis as described elsewhere herein. Mutations were introduced into cDNA constructs for LukA and LukB that can carry a N-Terminal 6xHis tag for purification purposes. Wild-type LukA and LukB DNA fragments (from Newman *S. aureus*) encoding the respective mature protein sequences were synthesized by PCR, treated with restriction enzymes to create cohesive ends, and cloned into expression vectors, e.g., the pET24a(+) and AmpR P15a origin LukB pET24a (+), as described in Example 3, digested by compatible restriction enzymes. Mutations were introduced into DNA using a commercially-available mutagenesis kit, e.g., by using the QUIKCHANGE® II Site-Directed Mutagenesis Kit (Stratagene).

Example 3: Plasmid Information and Protein Expression

The LukAB protein is unstable when expressed as separate sub-units, unlike other leukotoxins. DuMont et al. (2014) *Identification of a crucial residue required for Staphylococcus aureus LukAB cytotoxicity and receptor recognition.* Infect. Immun. 82, 1268-1276. So, LukA and LukB were expressed from two different plasmids within the same *E. coli* cell. To express both proteins, LukA (wild type or mutant versions) was cloned into pET24a (+) by using Ndel -Xhol restriction sites with existing Kanamycin resistant marker. For expression of LukB wt and mutant versions of proteins, pET24a(+) Kanamycin resistant marker was replaced with Ampicillin and the replication of origin was replaced by pl5a, resulting in plasmid: AmpR P15a origin LukB pET24a(+). LukB versions of proteins (WT and mutants) were cloned using Ndel -Xhol restriction sites. These LukB versions of plasmids were moved into BL21 (DE3) containing pET24a(+) LukA (either WT or mutant versions) plasmid by transformation selecting on LB plates containing both (Kanamycin 50 and Ampicillin 100) antibiotics.

The following is the sequence of the pl5a origin used to construct P15a origin LukB pET24a(+):

(SEQ ID NO: 59)

```
GCGCTAGCGGAGTGTATACTGGCTTACTATGTTGGCACTGATGAGGGT
GTCAGTGAAGTGCTTCATGTGGCAGGAGAAAAAAGGCTGCACCGGTGC
GTCAGCAGAATATGTGATACAGGATATATTCCGCTTCCTCGCTCACTG
ACTCGCTACGCTCGGTCGTTCGACTGCGGCGAGCGGAAATGGCTTACG
AACGGGGCGGAGATTTCCTGGAAGATGCCAGGAAGATACTTAACAGGG
AAGTGAGAGGGCCGCGGCAAAGCCGTTTTTCCATAGGCTCCGCCCCCC
TGACAAGCATCACGAAATCTGACGCTCAAATCAGTGGTGGCGAAACCC
GACAGGACTATAAAGATACCAGGCGTTTCCCCCTGGCGGCTCCCTCGT
GCGCTCTCCTGTTCCTGCCTTTCGGTTTACCGGTGTCATTCCGCTGTT
ATGGCCGCGTTTGTCTCATTCCACGCCTGACACTCAGTTCCGGGTAGG
CAGTTCGCTCCAAGCTGGACTGTATGCACGAACCCCCCGTTCAGTCCG
```

-continued

```
ACCGCTGCGCCTTATCCGGTAACTATCGTCTTGAGTCCAACCCGGAAA
GACATGCAAAAGCACCACTGGCAGCAGCCACTGGTAATTGATTTAGAG
GAGTTAGTCTTGAAGTCATGCGCCGGTTAAGGCTAAACTGAAAGGACA
AGTTTTGGTGACTGCGCTCCTCCAAGCCAGTTACCTCGGTTCAAAGAG
TTGGTAGCTCAGAGAACCTTCGAAAAACCGCCCTGCAAGGCGGTTTTT
TCGTTTTCAGAGCAAGAGATTACGCGCAGACCAAAACGATCTCAAGAA
GATCATCTTATTAATCAGATAAAATATTTCTAGATTTCAGTGCAATTT
ATCTCTTCAAATGTAGCACCTGAAGTCAGCCCCATACGATATAAGTTG
T
```

Example 4: Purification of LukAB Mutants

The LukAB sequences were cloned either into the pET-Duet or into separate pET24a+ expression plasmids. When using dual plasmid expression, the LukA was expressed using the standard pET24a+ plasmid, and the LukB was expressed using a modified plasmid having substituted ori (p15a) and antibiotic resistant cassette (AmpR) sequences. The plasmids were either singly transformed (pETDuet-1) or co-transformed (dual plasmid system) into BL21-DE3 cells. The protein expression was induced by the addition of IPTG to a mid-log phase cell culture, followed by overnight shaking incubation at 25° C. (approximately 16 hrs). The cells were pelleted by centrifugation, resuspended in cell lysis buffer, treated with lysozyme and lysed by sonication. The nucleic acid was removed by precipitation with polyethyleneimine (PEI), and the protein was salted out from the PEI supernatant by the addition of ammonium sulfate powder. The ammonium sulfate pellets were resuspended, buffer exchanged over a desalting column and clarified by centrifugation. The clarified, buffer exchanged material was next purified by a combination of cation exchange and mixed-mode chromatography, and then dialyzed into final formulation buffer.

Example 5: Attenuation of LukA and LukB Mutants

LukA and LukB mutants were tested in a neutrophil toxicity assay in combination with wild-type LukA, or LukB, respectively, by the following method. Using a 96-well round bottom tissue culture plate, the wild-type or mutant LukA or LukB proteins were diluted in duplicates down the plate in assay media (e.g., RPMI, 2% FBS, 5 mM glutamine) followed by addition of $5 \times 10^5$ DMSO induced HL-60 cells. HL-60 cells were differentiated into neutrophils by treatment with DMSO. The suspension was gently tapped and plates incubated for 48 hours at 37° C. with 5% $CO_2$ and 95% humidity. To determine cellular viability, 20 µL of 2 mg/mL diluted XTT (Sigma-Aldrich, St. Louis, Mo.) was added to each well, incubated for 6 hours at 37° C. with 5% $CO_2$ and 95% humidity, centrifuged and the supernatant transferred to an ELISA plate and read to 470 nm. The percent (%) viability was determined as follows: % Viability=(OD value of Experimental Sample Well/OD value of HL-60 cells without PVL Toxin)×100.

Example 6. Immunogenicity Study in Mice Using a Clinically Relevant Adjuvant Immunogenicity and adjuvant studies: Immunogenicity studies were performed in mice using clinically relevant adjuvants.

Groups of female BALB/c mice were vaccinated intramuscularly (IM) three times with 5 µg of mutant LukA, mutant LukB, or a combination of mutant LukA and LukB, with adjuvant at 2 week intervals. As controls, mice were vaccinated on the same schedule with wild-type (wt) LukA or LukB, as well as an irrelevant antigen (e.g., STEBVax; staph enterotoxin B vaccine), combined with an equivalent adjuvant. Mice were bled on days 21 and 35. Neutralizing antibody titers were determined using HL-60 derived neutrophils by pre-incubation of LukA or LukB proteins with serum prior to addition to the HL-60 cells, as described in the neutrophil toxicity assay above. The antibody response to LukA and/or LukB was compared to the response to wild-type LukA or LukB.

Example 7: Mutations Made and Tested for Protomer-Protomer Interface (Interface 1) and Results L61 of LukA (FIG. 1) aligns with H35 of alpha toxin and T28 of LukS PV. Mutations at H35 of alpha toxin reduces protomer-protomer interactions resulting in incomplete, larger octameric rings when observed by EM and abolishes the hemolytic activity of the toxin (Jursch et al, *Infect Immun.* 1994 June; 62(6):2249-56). Similarly, LukF T28 mutations have been shown to interfere with association of LukS-PV and LukF-PV (Guillet et al, 2004, *J Biol Chemistry,* 279(39):41028-37). L61 in LukA was mutated to N, Q, or R in individual constructs and respective $LukA_{mut}B_{wt}$ dimeric complexes were purified and tested for toxicity.

Figure 4:
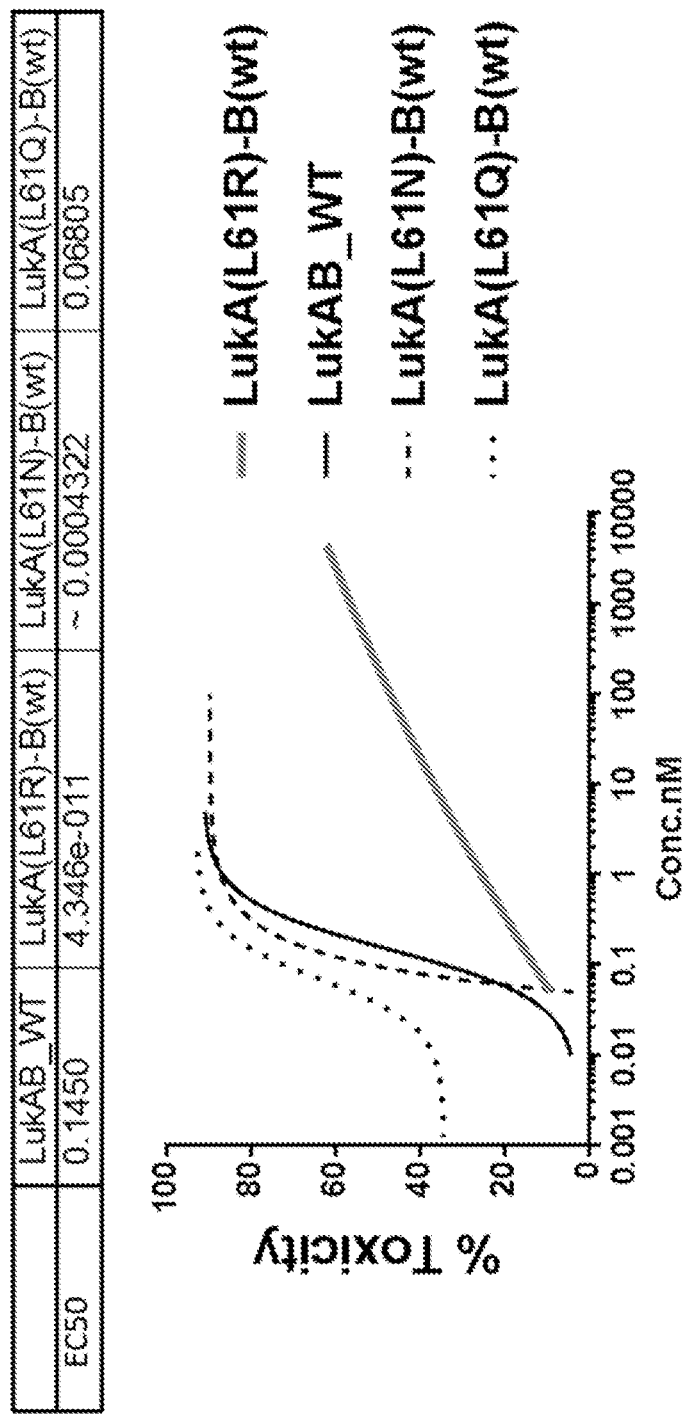

As shown in FIG. 4, mutagenesis of L61 to either N or Q did not attenuate LukAB with the L61Q mutant appearing to significantly increase the toxicity in particular at lower concentrations. Fifty percent toxic concentrations ($EC_{50}$) for $LukA_{L61N}B_{wt}$ and $LukA_{L61Q}B_{wt}$ were lower than wild-type LukAB. In contrast, L61R mutant of LukA was significantly attenuated. While the maximum average toxicity achieved with $LukA_{L61R}B_{wt}$ did not exceed 70%, toxicity was observed at concentrations as low as 1 nM. An $EC_{50}$ could not be calculated for $LukA_{L61R}B_{wt}$.

The protomer-protomer interaction is stabilized by a number of salt bridges (Baradau et al., 2015, *J Biot Chem.* 2900:142-56). Baradau et al had demonstrated that disruption of salt bridges in the rim domains of LukAB is destabilizing leading to insoluble molecules that could not be purified (Baradau et al., 2015, *J Biot Chem.* 290(1):142-56). Another salt bridge in the protomer-protomer interface involves LukA R49 interaction with LukB D49 (FIG. 1, Salt Bridge E). LukB mutants D49A and D49K were generated to disrupt this electrostatic interaction.

Figure 5:
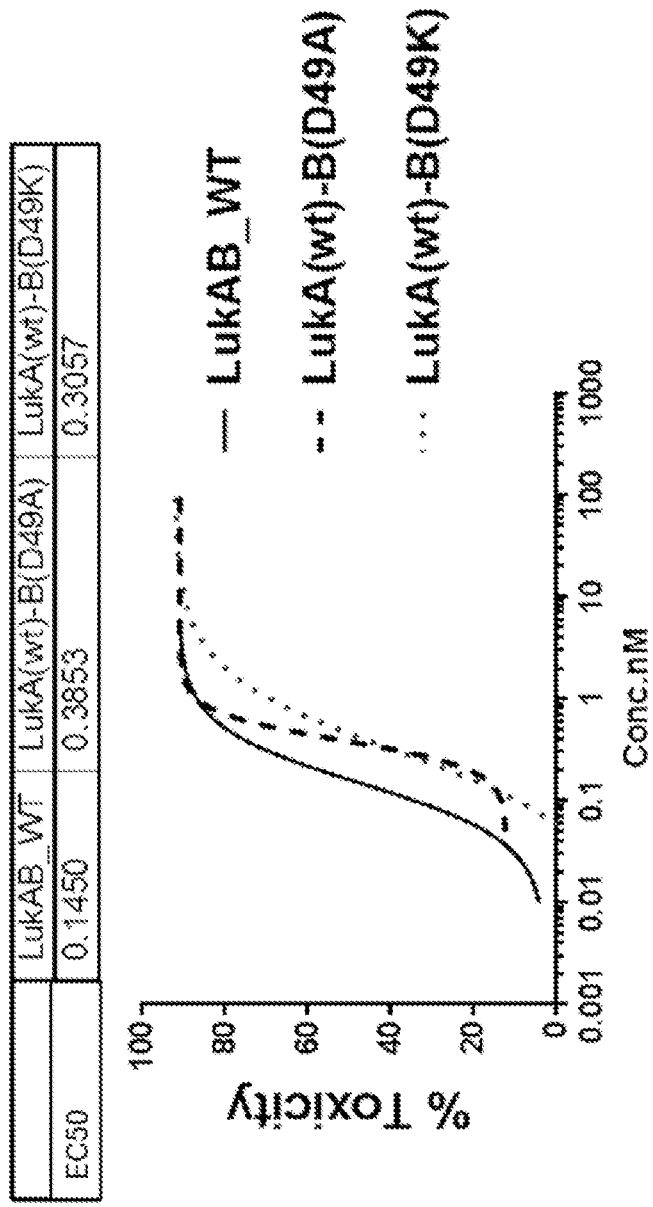

$LukA_{wt}B_{D49A}$ and $LukA_{wt}B_{D49K}$ exhibited only slight attenuation compared to wild-type LukAB with $EC_{50}$ values for D49A and D49K mutations only slightly increased (FIG. 5). These data indicated that mutating this salt bridge alone did not significantly attenuate LukAB.

Example 8: Mutations Made and Tested for Dimer-Dimer Interface (Interface 2) and Results Octamerization of LukAB dimers is required for its cytotoxicity (Baradau et al., 2015, *J Biol Chem.* 2900:142-56). Four salt bridges in the dimer-dimer interface stabilize the octameric structure (FIG. 1; Interface 2; Salt Bridges A-D). Baradau et al. demonstrated that combined alanine substitution of LukA D75 and D197 (Salt Bridges A and C in FIG. 1) when combined with wild-type LukB, or the reciprocal combined alanine substitution of R23 and K218 in LukB when combined with wild-type LukA were non-toxic in HL-60 cells derived human neutrophils at concentrations up to ~50 nM. Higher concentrations were not tested. Here, several mutants were produced disrupting one or more of the salt bridges to identify potential vaccine candidates.

LukB mutants bearing mutations in K12, K19, R23, K58, K218, E112, or a combination thereof were generated each individually in complex with LukA$_{wt}$. LukA mutants bearing mutations in either D39, D75, K138, D197, or a combination thereof were generated each individually in complex with LukB$_{wt}$. All proteins were soluble and could be purified at a reasonable yield.

Figure 6:
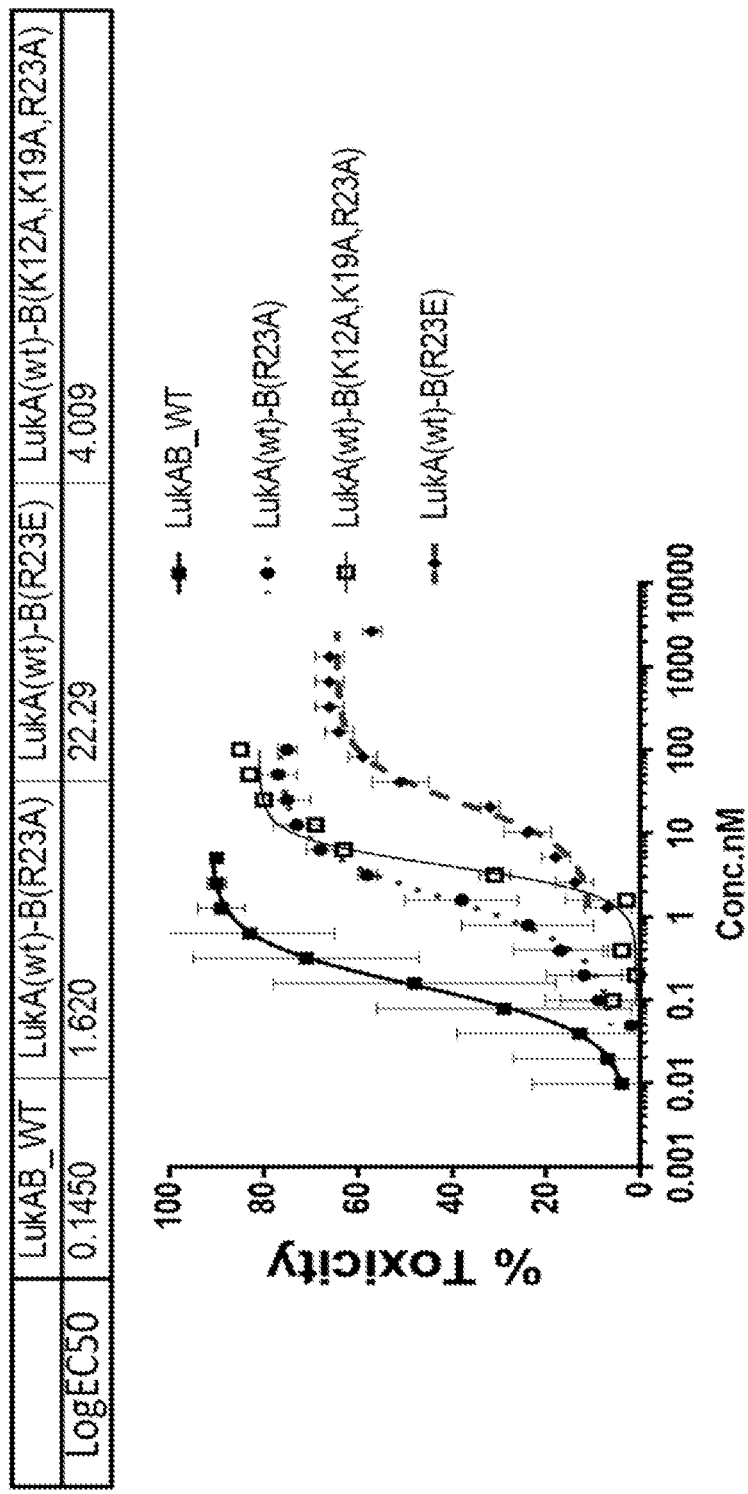

Disruption of Salt Bridge A. Mutation of R23 to alanine and glutamic acid when combined with wild-type LukA significantly attenuated the toxic activity of LukAB (FIG. 6). Both mutants could be produced and purified readily as dimers. LukA$_{wt}$B$_{R23A}$ showed an EC50 of 1.62 nM representing about 12-fold attenuation while LukA$_{wt}$B$_{R23E}$ mutant exhibited an EC50 of 22.29 nM representing about 150-fold attenuation. Visual inspection of the crystal structure highlighted two additional positively charged LukB residues in the vicinity of R23 (K12 and K19) that may also contribute to a positively charged pocket and interacting with LukA D75. A third mutant was therefore generated with three substitutions in LukB: LukA$_{wt}$B$_{K12A/K19A/R23A}$. This triple mutant was more attenuated than LukA$_{wt}$B$_{BR23A}$ but far less than LukA$_{wt}$B$_{R23E}$. Despite attenuation, at higher concentrations both mutants showed residual toxicity of 65-75% (FIG. 6). These data indicate that targeting the Salt Bridge A is highly effective in attenuating the toxins, however, residual toxicity remains at high concentrations of the mutants.

Sequence alignment of HlgB and LukB suggested that HlgB lacks the crucial positively-charged residues at the N terminus that are important to attenuate LukAB toxicity. Therefore, as an alternative approach, the first 29 residues of LukB were swapped with HlgB to reduce LukAB toxicity and generate an antibody response to the N terminal residues of HlgB. This LukB$_{HlgB}$ mutant when paired with LukA$_{wt}$ and LukA$_{L61R}$ showed no toxicity at concentrations as high as 20 μM.

The sequence of HlgB-LukB fusion is below. The bold underlined portion is the N terminus of HlgB that was swapped with N terminus of LukB:

(SEQ ID NO: 58)
AEGKITPVSVKKVDDKVTLYKTTATADSDQKNITQSLQFNFLTEPNYD
KETVFIKAKGTIGSGLRILDPNGYWNSTLRWPGSYSVSIQNVDDNNNT
NVTDFAPKNQDESREVKYTYGYKTGGDFSINRGGLTGNITKESNYSET
ISYQQPSYRTLLDQSTSHKGVGWKVEAHLINNMGHDHTRQLTNDSDNR
TKSEIFSLTRNGNLWAKDNFTPKDKMPVTVSEGFNPEFLAVMSHDKKD
KGKSQFVVHYKRSMDEFKIDWNRHGFWGYWSGENHVDKKEEKLSALYE
VDWKTHNVKFVKVLNDNEKK

Disruption of Salt Bridge B. Salt Bridge B involves electrostatic interactions between LukA D39 and LukB K58. Four mutants were produced to disrupt this salt bridge: LukA$_{wt}$B$_{K58A}$, LukA$_{wt}$B$_{K58E}$, LukA$_{D39A}$B$_{wt}$, and LukA$_{D39R}$B$_{wt}$. All proteins could be produced and purified as dimers. The LukB mutants complexed with wild-type LukA showed about 30-fold attenuation with residual toxicity of >80% (FIG. 7A). Reciprocal mutations of LukA D39 to alanine or arginine were also generated and purified complexed with wild-type LukB. As shown in FIG. 7B, these mutants had toxicity profiles similar to wild-type LukAB with slight attenuation observed with LukA$_{D39A}$.

Figure 8:
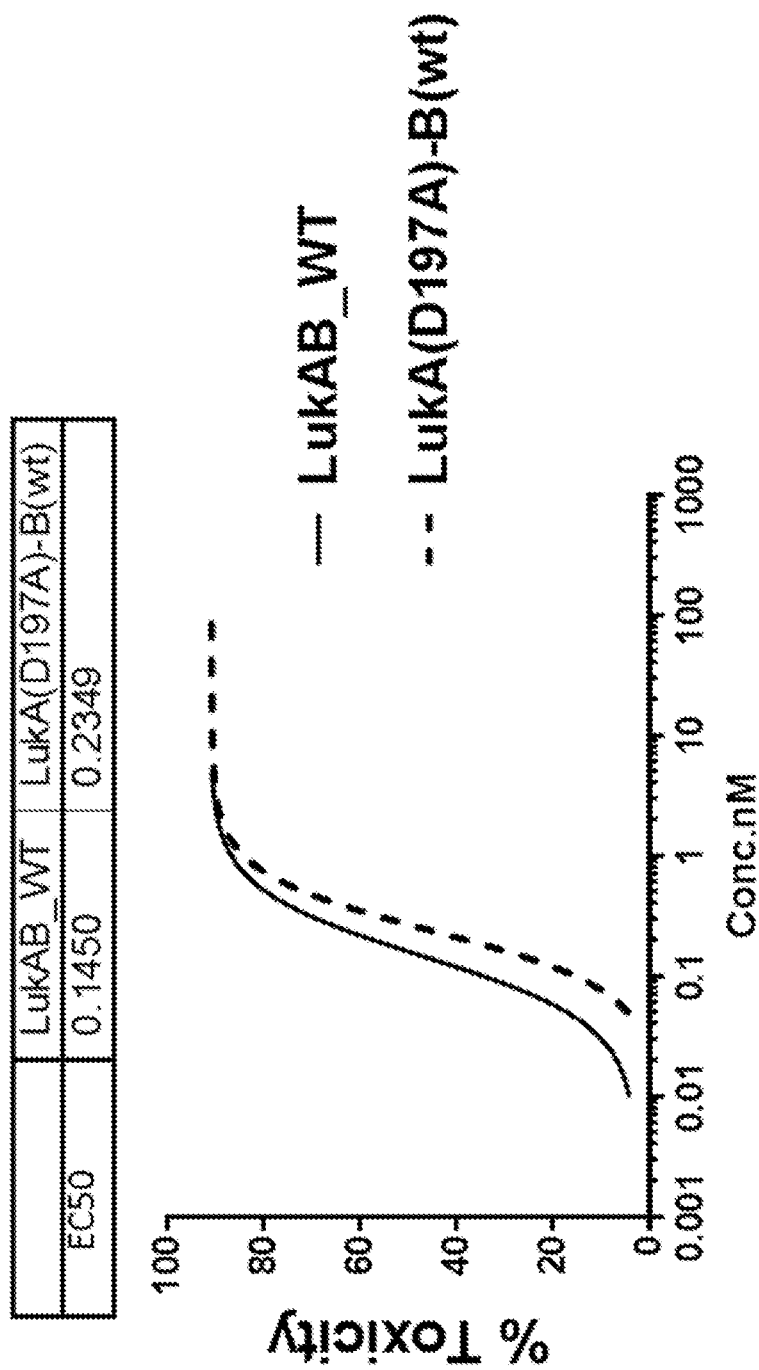

Disruption of Salt Bridge C. Salt Bridge C involves electrostatic interactions between LukA D197 and LukB K218. A LukA$_{D197A}$LukB$_{wt}$ mutant was created and tested for toxicity. The protein was expressed well and purified as dimer. However, the mutant was not significantly attenuated (FIG. 8) indicating that a single mutation in Salt Bridge C did not in this experiment impact toxicity.

Figure 9:
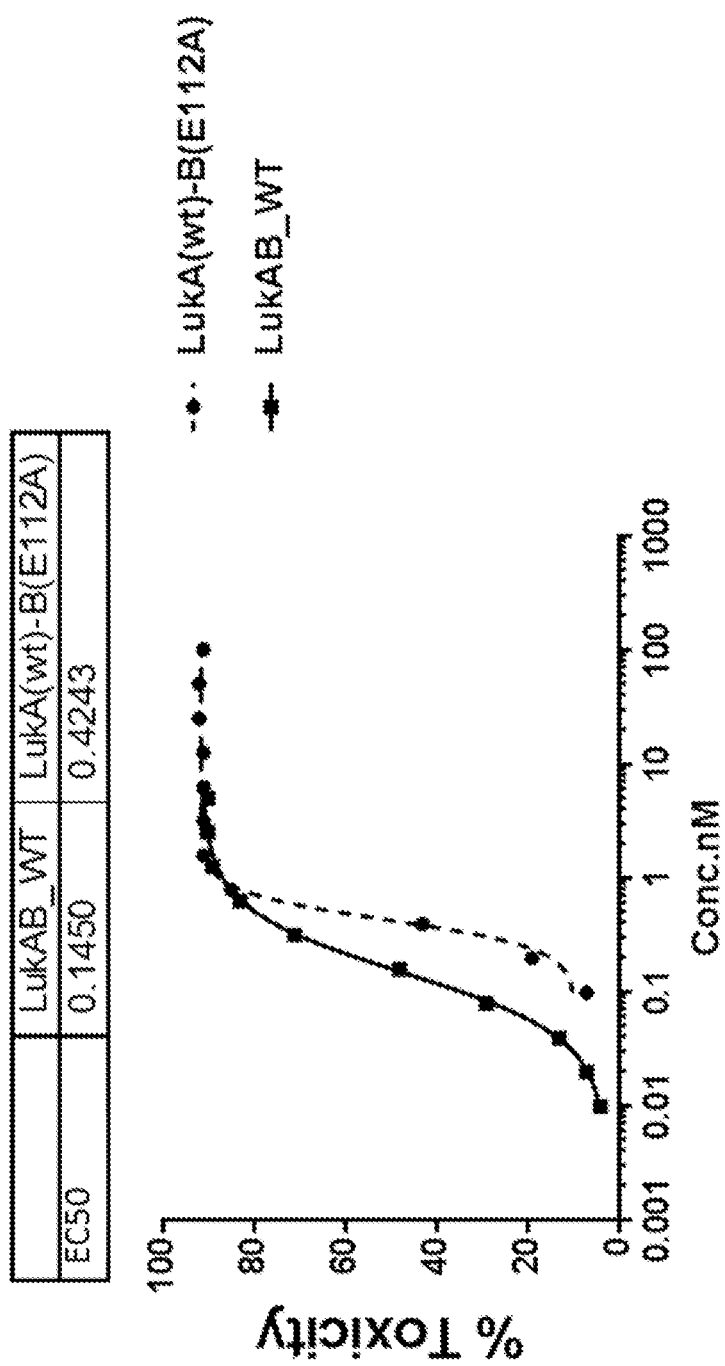

Disruption of Salt Bridge D. Structural interface analysis by PDB PISA suggested a potential salt bridge between LukA K138 and LukB E112 (Salt Bridge D). Purified mutant LukA$_{wt}$LukB$_{E112A}$ was in this experiment only modestly attenuated (FIG. 9).

Figure 10:
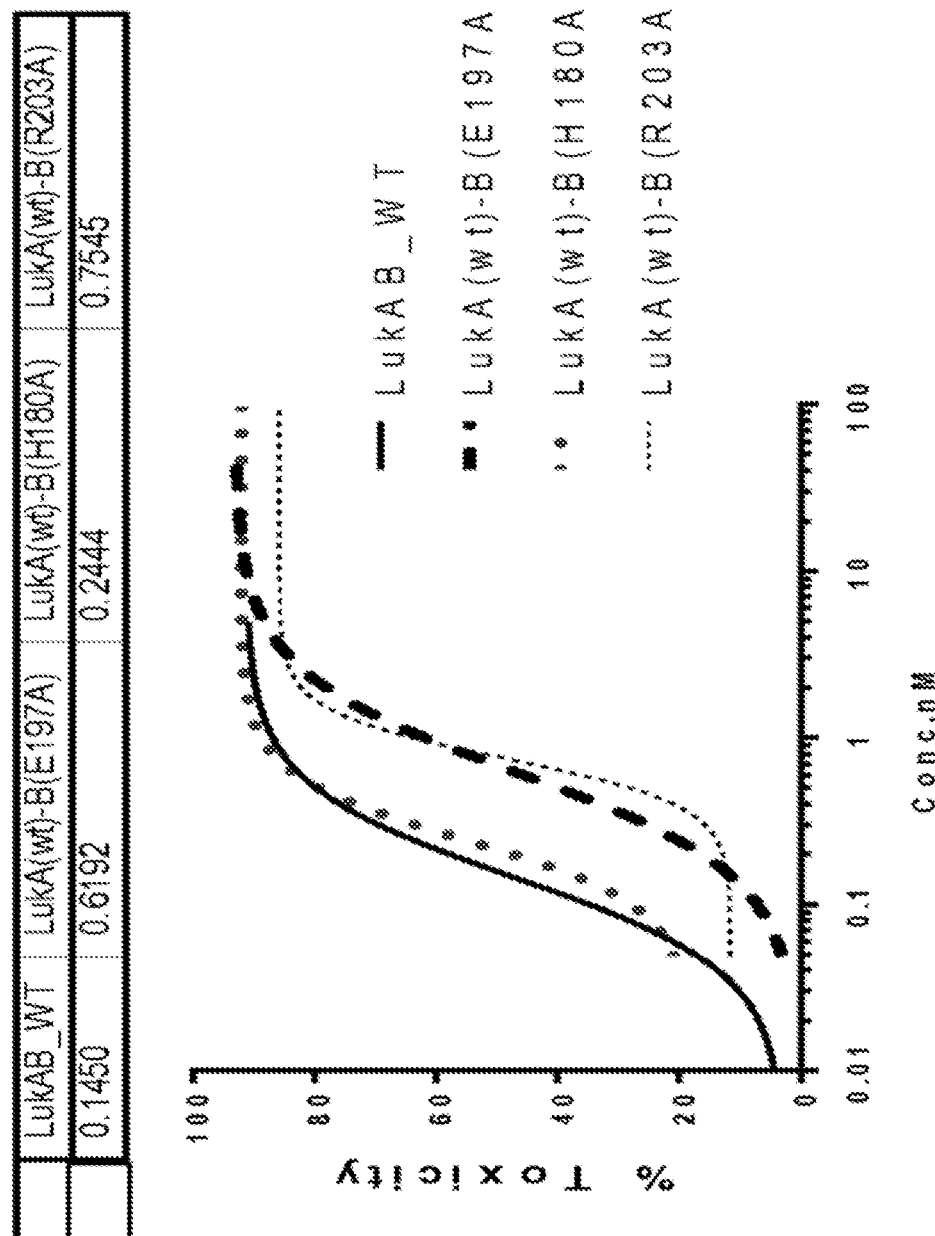

Example 9: Mutations Made and Tested for the Membrane Binding Cleft and Results The membrane binding cleft of LukF-PV that binds to phosphocholine has been identified to include residues W176, E191, and R197 (Guillet et al, 2004, J Biol Chemistry, 279(39):41028-37). Homologous residues in LukB molecule (H180, E197, and R203 respectively) were mutated to investigate the impact on toxicity of LukAB. While alanine substitution of H180 had no impact on LukAB toxicity, the other mutants LukA$_{wt}$LukB$_{E197A}$ and LukA$_{wt}$LukB$_{R203A}$ showed modest attenuation with EC$_{50}$ values increased by 4.3 and 5.2-fold, respectively, compared to wild-type (FIG. 10).

Example 10: Mutations Made and Tested for the Pore and Results

Residues within a flexible surface loop on LukB, residues 125-133 (FSINRGGLT), were deleted to obturate the cytoplasmic edge of the pore. Along with the deletion, these residues were replaced with short glycine linkers (1-5 glycines) after D124 to provide a flexible loop between D124 and G134 and maintain protein structure stability. The residues within this loop were alternatively swapped with those from a homologous region in HlgB (SNGLS). All of these LukB mutants when paired with LukA$_{wt}$ resulted in very poor yields with modest attenuation of toxicity.

Example 11: Combined Mutations, Results and Selection of Vaccine Candidates

Further effort focused on combining individual mutations to achieve greatest attenuation. Furthermore, the mutant proteins were evaluated for immunogenicity in mice.

Combined mutations including $LukA_{L61R}$. $LukA_{L61R}$ was combined with of LukB mutants having single amino acid substitutions in Salt Bridges A (R23), C (K218), D (E112) and E (D49). In addition, the L61R mutation of LukA was also combined with HlgB-LukB fusion and LukB K12/K19/R23 mutants that disrupt the Salt Bridge A. furthermore, L61R was combined with R203A mutation in the membrane binding cleft.

As shown in Table 2, overall, mutants containing L61R were highly attenuated with some essentially showing no toxic activity at the highest concentrations of 10-12 μM. Some of the mutants such as $LukA_{L61R}LukB_{E112A}$, $LukA_{L61R}LukB_{R203A}$, and $LukA_{L61R}LukB_{K218A}$ exhibited residual toxicity at higher concentrations (Table 2). Several of the toxoids were tested for immunogenicity and exhibited a range of antibody response about 20-30% of the wild-type antigen (Table 2).

Combined mutations affecting salt bridges. LukA D39 (Salt Bridge B) mutations that by themselves have a modest attenuating effects were combined with other LukB mutations in Salt Bridge A (R23 and triple mutation of K12/K19/R23), C (K218), and D (E112). As shown in Table 2, the attenuation levels varied largely with $LukA_{D39A}LukB_{E112A}$, $LukA_{D39R}LukB_{E112A}$, and $LukA_{D39A}LukB_{K218A}$ being only two-fold attenuated while $LukA_{D39A}LukB_{R23E}$ and $LukA_{D39R}LukB_{R23E}$ were 696-fold and 419-fold attenuated, respectively. $LukA_{D39A}LukB_{R23E}$ exhibited lower residual toxicity and higher immunogenicity than $LukA_{D39R}LukB_{R23E}$ (Table 2).

$LukA_{D197K}$ (Salt Bridge C) was also combined with LukB Salt Bridge A mutants. As shown in Table 2, $LukA_{D197K}LukB_{R23E}$ showed higher level of attenuation (588-fold) but lower level of immunogenicity compared with $LukA_{D39R}LukB_{R23E}$. Furthermore, $LukA_{K138A}LukB_{K218A}$ mutant was also generated. However, this mutant was not attenuated compared to wild-type LukAB (Table 2).

A select set of toxoids that showed good attenuation were tested again for immunogenicity. Groups of 5 mice were immunized wither with $LukA_{wt}LukB_{R23E}$, $LukA_{D39A}LukB_{R23E}$, $LUkA_{L61R}LUkB_{HlgB}$, and $LukA_{L61R}LukB_{K12A/K19A/R23A}$, or wild-type LukAB all formulated in ALHYDROGEL®. Sera from individual mice were tested for ELISA binding and toxin neutralization. As shown in FIG. 11, all toxoids showed similar ELISA IgG titers. However, the neutralizing titers among the combined mutants (highly attenuated toxoids; at least one mutation in each subunit) was highest with $LukA_{D39A}LUkB_{R23E}$.

TABLE 2

Toxicity, and immunogenicity of combined mutations of copurified LukA and LukB toxoids. Fold attenuation was calculated as ratio of toxoid EC50 over wild-type (HL60 assay). Immunogenicity was performed in groups of five mice and pooled sera from each group tested for ELISA binding to wild-type LukAB or neutralization of wild-type LukAB.

| LukA | LukB | EC50 (nM) | Attenuation (fold) | Residual toxicity | TNA (NT50) (serum dilution) | ELISA (EC50) (serum dilution) |
|---|---|---|---|---|---|---|
| wt | wt | 0.145 | 1 | 100% | 2950 | 6535 |
| L61R | D49K | 199 | 1372 | 100% | NT | 1220 |
| L61R | R23A | >10,000 | >68,000 | 0% | 165 | 853 |
| L61R | R23E | 11000 | 75862 | 0% | 219 | 1560 |
| L61R | E112A | >50 | >345 | 96% | 598 | NT |
| L61R | R203A | 40 | 275 | 55% | NT | NT |
| L61R | K218A | 236 | 1628 | 54% | NT | 2640 |
| L61R | K12A/K19A/R23A | 12430 | 85724 | 0% | 613 | 2310 |
| L61R | LukB-HlgB | >8,000 | >55,000 | 0% | 728 | 67222 |
| D39A | E112A | 0.26 | 2 | 100% | NT | 4770 |
| D39A | K12A/K19A/R23A | 2.56 | 18 | 96% | 1030 | 965 |
| D39R | K12A/K19A/R23A | 0.58 | 4 | 94% | NT | 942 |
| D39A | R23E | 101 | 696 | 60% | 784 | 1560 |
| D39A | K218A | 0.35 | 2 | 100% | NT | 3615 |
| D39R | E112A | 0.263 | 2 | 100% | NT | 1560 |
| D39R | R23E | 60.8 | 419 | 77% | 334 | 682 |
| D39R | K218A | <7 | <48 | 100% | 2170 | NT |
| D197K | R23A | <12 | <82 | 100% | NT | 1610 |
| D197K | R23E | 85 | 588 | 76% | NT | 855 |
| K138A | K218A | 0.15 | 1 | 100% | NT | 2320 |

The present disclosure is not to be limited in scope by the specific aspects or embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

SEQUENCES

LukA sequences
SEQ ID NO: 1
MKNKKRVLIASSLSCAILLLSAATTQANSAHKDSQDQNKKEHVDKSQQKEKRNVTNKD
KNSTXPDDIGKNGKITKRTETVYDEKTNILQNLQFDFIDDPTYDKNVLLVKKQGSIHSNL
KFESHKEEKNSNWLKYPSEYHVDFQVKRNRKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKDGQRLIVTYEVDWKNKTVKVVDKYSDDNKPYKEG SEQ ID NO: 2
MKNKKRVLIASSLSCAILLLSAATTQANSAHKDSQDQNKKEHVDKSQQKDKRNVTNKD
KNSTAPDDIGKNGKITKRTETVYDEKTNILQNLQFDFIDDPTYDKNVLLVKKQGSIHSNL
KFESHKEEKNSNWLKYPSEYHVDFQVKRNRKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKDGQRLIVTYEVDWKNKTVKVVDKYSDDNKPYKEG SEQ ID NO: 3
MKNKKRVFIASSLSCALLLLSAANTEANSANKDSQDQTKKEHVDKAQQKEKRNVNDK
DKNTPGPDDIGKNGKVTKRTVSEYDKETNILQNLQFDFIDDPTYDKNVLLVKKQGSIHS
NLKFESHRNETNASWLKYPSEYHVDFQVQRNPKTEILDQLPKNKISTAKVDSTFSYSLGG
KFDSTKGIGRTSSNSYSKSISYNQQNYDTIASGKNNNRHVHWSVVANDLKYGNEIKNRN
DEFLFYRNTRLSTVENPELSFASKYRYPALVRSGFNPEFLTYISNEKSNEKTRFEVTYTRN
QDILKNKPGIHYGQPILEQNKDGQRFIVVYEVDWKNKTVKVVEKYSDQNKPYKEG SEQ ID NO: 4
MKNKKRVLIASSLSCAILLLSAATTQANSAHKDSQDQNKKEHVDKSQQKEKRNVTNKD
KNSTVPDDIGKNGKITKRTETVYDEKTNILQNLQFDFIDDPTYDKNVLLVKKQGSIHSNL
KFESHKEEKNSNWLKYPSEYHVDFQVKRNRKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKEGQRLIVTYEVDWKNKTVKVVDKYSDNKSFREG SEQ ID NO: 5
MKNKKRVLIASSLSCAILLLSAATTQANSAHKDSQDQNKKEHVDKSQQKDKRNVTNKD
KNSTAPDDIGKNGKITKRTETVYDEKTNILQNLQFDFIDDPTYDKNVLLVKKQGSIHSNL
KFESHKEEKNSNWLKYPSEYHVDFQVKRNPKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKEGQRLIVTYEVDWKNKTVKVVDKYTDNKSFREG SEQ ID NO: 6
MKNKKRVLIASSLSCAILLLSAATTQANSAHKDSQDQNKKEHVDKSQQKEKRNVTNKD
KNSTVPDDIGKNGKITKRTETVYDEKTNILQNLQFDFIDDPTYDKNVLLVKKQGSIHSNL
KFESHKEEKNSNWLKYPSEYHVDFQVKRNPKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKEGQRLIVTYEVDWKNKTVKVVDKYSDNKSFREG SEQ ID NO: 7
MKNKKRVLIASSLSCAILLLSAATTQANSAHKDSQDQNKKEHVDKSQQKDKRNVTNKD
KNSTVPDDIGKNGKITKRTETVYDEKTNILQNLQFDFIDDPTYDKNVLLVKKQGSIHSNL
KFESHKEEKNSNWLKYPSEYHVDFQVKRNRKTEILDQLPKNKISTAKVDSTFSYSSGGKF
DSTKGIGRTSSNSYSKTISYNQQNYDTIASGKNNNWHVHWSVIANDLKYGGEVKNRND
ELLFYRNTRIATVENPELSFASKYRYPALVRSGFNPEFLTYLSNEKSNEKTQFEVTYTRNQ
DILKNRPGIHYAPPILEKNKDGQRLIVTYEVDWKNKTVKVVDKYSDDNKPYKEG SEQ ID NO: 8
MKNKKRVLIASSLSCAILLLSAATTQANSAHKDSQDQNKKEHVDKSQQKDKRNVTNKD
KNSTVPDDIGKNGKITKRTETVYDEKTNILQNLQFDFIDDPTYDKNVLLVKKQGSIHSNL
KFESHKEEKNSNWLKYPSEYHVDFQVKRNRKTEILDQLPKNKISTAKVDSTFSYSSGGKF
DSTKGIGRTSSNSYSKTISYNQQKYDTIAIGKNNNWHVHWSVIANDLKYGGEVKNRDE
LLFYRNTRIATVENPELSFASKYRYPALVRSGFNPEFLTYLSNEKSNEKTQFEVTYTRNQ
DILKNRPGIHYAPPILEKNKDGQRLIVTYEVDWKNKTVKVVDKYSDDNKPYKEG SEQ ID NO: 9
MKNKKRVLIASSLSCAILLLSAATTQANSAHKDSQDQNKKEHVDKSQQKDKRNVTNKD
KNSTAPDDIGKNGKITKRTETVYDEKTNILQNLQFDFIDDPTYDKNVLLVKKQGSIHSNL

| SEQUENCES |
|---|
| KFESHKEEKNSNWLKYPSEYHVDFQVKRNRKTEILDQLPKNKISTAKVDSTFSYSSGGKF<br>DSTKGIGRTSSNSYSKTISYNQQNYDTIASGKNNNWHVHWSVIANDLKYGGEVKNRND<br>ELLFYRNTRIATVENPELSFASKYRYPALVRSGFNPEFLTYLSNEKSNEKTQFEVTYTRNQ<br>DILKNRPGIHYAPPILEKNKDGQRLIVTYEVDWKNKTVKVVDKYSDDNKPYKEG<br><br>SEQ ID NO: 10<br>MKNKKRVFIASSLSCALLLLSAANTEANSANKDSQDQTKKEHVDKAQQKEKRNVNDK<br>DKNTPGPDDIGKNGKVTKRTVSEYDKETNILQNLQFDFIDDPTYDKNVLLVKKQGSIHS<br>NLKFESHRNETNASWLKYPSEYHVDFQVQRNPKTEILDQLPKNKISTAKVDSTFSYSLGG<br>KFDSTKGIGRTSSNSYSKSISYNQQNYDTIASGKNNNRHVHWSVVANDLKYGNEIKNRN<br>DEFLFYRNTRLSTVENPELSFASKYRYPALVRSGFNPEFLTYISNEKTNDKTRFEVTYTRN<br>QDILKNKPGIHYGQPILEQNKDGQRFIVVYEVDWKNKTVKVVEKYSDQNKPYKEG<br><br>SEQ ID NO: 11<br>MKNKKRVFIASSLSCALLLLSAANTEANSANKDSQDQTKKEHVDKAQQKEKRNVNDK<br>DKNTPGPDDIGKNGKVTKRTETVYDEKTNILQNLQFDFIDDPTYDKNVLLVKKQGSIHS<br>NLKFESHKEENNSSWLKYPSEYHVDFQVKSNRKTEILDQLPKNKISTAKVDSTFSYNSGG<br>KFDSVKGVGRTSSNSYSKTISYNQQNYDTIASGKNNNWHVHWSVVANDLKYGGEVKN<br>RNDDFLFYRNTRLSTVENPELSFASKYRYPALVRSGFNPEFLTYLSNEKSNEKTQFEVTY<br>TRNQDVLKNKPGIHYAPPILEKNKDGQRLIVTYEVDWKNKTVKVIDKYSDENKPYKEG<br><br>SEQ ID NO: 12<br>MKNKKRVFIASSLSCVLLLLSAANTEANSANKDSQDQTKKEHVDKAQQKEKRNVNDK<br>DKNTPGPDDIGKNGKVTKRTVSEYDKETNILQNLQFDFIDDPTYDKNVLLVKKQGSIHS<br>NLKFESHRNETNASWLKYPSEYHVDFQVQRNPKTEILDQLPKNKISTAKVDSTFSYSLGG<br>KFDSTKGIGRTSSNSYSKSISYNQQNYDTIASGKNNNRHVHWSVVANDLKYGNEIKNRN<br>DEFLFYRNTRLSTVENPELSFASKYRYPALVRSGFNPEFLTYISNEKSNEKTRFEVTYTRN<br>QDILKNKPGIHYGQPILEQNKDGQRFIVVYEVDWKNKTVKVVEKYSDQNKPYKEG<br><br>SEQ ID NO: 13<br>MKNKKRVFIASSLSCALLLLSAANTEANSANKDSQDQTKKEHVDKAQQKEKRNVNDK<br>DKNTPGPDDIGKNGKVTKRTETVYDEKTNILQNLQFDFIDDPTYDKNILLVKKQGSIHSN<br>LKFESHKEENNSSWLKYPSEYHVDFQVKRNRKTEILDQLPKNKISTAKVDSTFSYNSGG<br>KFDSVKGVGRTSSNSYSKTISYNQQNYDTIASGKNNNWHVHWSVVANDLKYGGEVKN<br>RNDEFLFYRTTRLSTVENPELSFASKYRYPALVRSGFNPEFLTYLSNEKSNEKTQFEVTYT<br>RNQDILKNKPGIHYAPPILEKNKDGQRLIVTYEVDWKNKTVKVIDKYSDDNKPYKEG<br><br>SEQ ID NO: 14<br>MKNKKRVLIASSLSCAILLLSAATTQANSAHKDSQDQNKKEHVDKSQQKDKRNVTNKD<br>KNSTVPDDIGKNGKITKRTETVYDEKTNILQNLQFDFIDDPTYDKNVLLVKKQGSIHSNL<br>KFESHKEEKNSNWLKYPSEYHVDFQVKRNRKTEILDQLPKNKISTAKVDSTFSYSSGGKF<br>DSTKGIGRTSSNSYSKTISYNQQNYDTIASGKNNNWHVHWSVIANDLKYGGEVKNRND<br>ELLFYRNTRIATVENPELSFASKYRYPALVRSGFNPEFLTYLSNEKSNEKTQFEVTYTRNQ<br>DILKNRPGIHYAPSILEKNKDGQRLIVTYEVDWKNKTVKVVDKYSDDNKPYKEG<br><br>SEQ ID NO: 28<br>NSAHKDSQDQNKKEHVDKSQQKEKRNVTNKDKNSTXPDDIGKNGKITKRTETVYDEKT<br>NILQNLQFDFIDDPTYDKNVLLVKKQGSIHSNLKFESHKEEKNSNWLKYPSEYHVDFQV<br>KRNRKTEILDQLPKNKISTAKVDSTFSYSSGGKFDSTKGIGRTSSNSYSKTISYNQQNYDT<br>IASGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKDGQRLIV<br>TYEVDWKNKTVKVVDKYSDDNKPYKEG<br><br>SEQ ID NO: 30 (encoding SEQ ID NO: 2)<br>ATGAAAAATA AAAACGTGT TTTAATAGCG TCATCATTAT CATGTGCAAT<br>TTTATTGTTA TCAGCAGCAA CGACTCAAGC AAATTCAGCT CATAAAGACT<br>CTCAAGACCA AAATAAGAAA GAACATGTTG ATAAGTCTCA ACAAAAAGAC<br>AAACGTAATG TTACTAATAA AGATAAAAAT TCAACAGCAC CGGATGATAT<br>TGGGAAAAAC GGTAAAATCA CAAAACGAAC TGAAACAGTA TATGATGAGA<br>AAACAAATAT ACTCCAAAAT TTACAATTCG ACTTTATCGA TGATCCAACT<br>TATGACAAGA ATGTATTACT TGTTAAAAAA CAAGGCTCAA TTCATTCAAA<br>TTTAAAGTTT GAATCTCATA AGAAGAAAA AAATTCAAAT TGGTTAAAGT<br>ATCCAAGTGA GTACCATGTA GATTTTCAAG TAAAAAGAAA TCGTAAAACT<br>GAAATATTAG ACCAATTGCC GAAAAATAAA ATTTCAACTG CAAAAGTAGA<br>CAGTACATTT TCATATAGCT CAGGTGGTAA ATTCGATTCA ACAAAAGGTA<br>TTGGACGAAC TTCATCAAAT AGCTACTCCA AAACGATTAG TTATAATCAG<br>CAAAATTATG ACACAATTGC CAGCGGTAAA AATAATAACT GGCATGTACA<br>CTGGTCAGTT ATTGCGAATG ACTTGAAGTA TGGTGGAGAA GTGAAAAATA<br>GAAATGATGA ATTATTATTC TATAGAAATA CGAGAATTGC TACTGTAGAA<br>AACCCTGAAC TAAGCTTTGC TTCAAATAT AGATACCCAG CATTAGTAAG<br>AAGTGGCTTT AATCCAGAAT TTTTAACTTA TTTATCTAAT GAAAAGTCAA<br>ATGAGAAAAC GCAATTTGAA GTAACATACA CACGAAATCA AGATATTTTG<br>AAAAACAGAC CTGGAATACA TTATGCACCT CCAATTTTAG AAAAAAATAA<br>AGATGGTCAA AGATTAATTG TCACTTATGA AGTTGATTGG AAAAATAAA<br>CAGTTAAAGT CGTTGATAAA TATTCTGATG ACAATAAACC TTATAAGAA<br>GGATAA |

| SEQUENCES |
| --- |
| SEQ ID NO: 32<br>NSAHKDSQDQNKKEHVDKSQQKDKRNVTNKDKNSTAPDDIGKNGKITKRTETVYDEK<br>TNILQNLQFDFIDDPTYDKNVLLVKKQGSIHSNLKFESHKEENSNWLKYPSEYHVDFQ<br>VKRNRKTEILDQLPKNKISTAKVDSTFSYSSGGKFDSTKGIGRTSSNSYSKTISYNQQNYD<br>TIASGKNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKDGQRLIV<br>TYEVDWKNKTVKVVDKYSDDNKPYKEG<br><br>SEQ ID NO: 33<br>NSANKDSQDQTKKEHVDKAQQKEKRNVNDKDKNTPGPDDIGKNGKVTKRTVSEYDKE<br>TNILQNLQFDFIDDPTYDKNVLLVKKQGSIHSNLKFESHRNETNASWLKYPSEYHVDFQ<br>VQRNPKTEILDQLPKNKISTAKVDSTFSYSLGGKFDSTKGIGRTSSNSYSKSISYNQQNYD<br>TIASGKNNNRHVHWSVVANDLKYGNEIKNRNDEFLFYRNTRLSTVENPELSFASKYRYP<br>ALVRSGFNPEFLTYISNEKSNEKTRFEVTYTRNQDILKNKPGIHYGQPILEQNKDGQRFIV<br>VYEVDWKNKTVKVVEKYSDQNKPYKEG<br><br>SEQ ID NO: 34<br>NSAHKDSQDQNKKEHVDKSQQKEKRNVTNKDKNSTVPDDIGKNGKITKRTETVYDEKT<br>NILQNLQFDFIDDPTYDKNVLLVKKQGSIHSNLKFESHKEEKNSNWLKYPSEYHVDFQV<br>KRNRKTEILDQLPKNKISTAKVDSTFSYSSGGKFDSTKGIGRTSSNSYSKTISYNQQNYDT<br>IASGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKEGQRLIV<br>TYEVDWKNKTVKVVDKYSDNKSFREG<br><br>SEQ ID NO: 35<br>NSAHKDSQDQNKKEHVDKSQQKDKRNVTNKDKNSTAPDDIGKNGKITKRTETVYDEK<br>TNILQNLQFDFIDDPTYDKNVLLVKKQGSIHSNLKFESHKEEKNSNWLKYPSEYHVDFQ<br>VKRNPKTEILDQLPKNKISTAKVDSTFSYSSGGKFDSTKGIGRTSSNSYSKTISYNQQNYD<br>TIASGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKEGQRLIV<br>TYEVDWKNKTVKVVDKYTDNKSFREG<br><br>SEQ ID NO: 36<br>NSAHKDSQDQNKKEHVDKSQQKEKRNVTNKDKNSTVPDDIGKNGKITKRTETVYDEKT<br>NILQNLQFDFIDDPTYDKNVLLVKKQGSIHSNLKFESHKEEKNSNWLKYPSEYHVDFQV<br>KRNPKTEILDQLPKNKISTAKVDSTFSYSSGGKFDSTKGIGRTSSNSYSKTISYNQQNYDTI<br>ASGKNNNWHVHWSVIANDLKYGGEVKNRNDELLFYRNTRIATVENPELSFASKYRYPA<br>LVRSGFNPEFLTYLSNEKSNEKTQFEVTYTRNQDILKNRPGIHYAPPILEKNKEGQRLIVT<br>YEVDWKNKTVKVVDKYSDNKSFREG<br><br>SEQ ID NO: 37<br>NSAHKDSQDQNKKEHVDKSQQKDKRNVTNKDKNSTVPDDIGKNGKITKRTETVYDEK<br>TNILQNLQFDFIDDPTYDKNVLLVKKQGSIHSNLKFESHKEEKNSNWLKYPSEYHVDFQ<br>VKRNRKTEILDQLPKNKISTAKVDSTFSYSSGGKFDSTKGIGRTSSNSYSKTISYNQQNYD<br>TIASGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKDGQRLIV<br>TYEVDWKNKTVKVVDKYSDDNKPYKEG<br><br>SEQ ID NO: 38<br>NSAHKDSQDQNKKEHVDKSQQKDKRNVTNKDKNSTVPDDIGKNGKITKRTETVYDEK<br>TNILQNLQFDFIDDPTYDKNVLLVKKQGSIHSNLKFESHKEEKNSNWLKYPSEYHVDFQ<br>VKRNRKTEILDQLPKNKISTAKVDSTFSYSSGGKFDSTKGIGRTSSNSYSKTISYNQQKYD<br>TIAIGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKDGQRLIV<br>TYEVDWKNKTVKVVDKYSDDNKPYKEG<br><br>SEQ ID NO: 39<br>NSAHKDSQDQNKKEHVDKSQQKDKRNVTNKDKNSTAPDDIGKNGKITKRTETVYDEK<br>TNILQNLQFDFIDDPTYDKNVLLVKKQGSIHSNLKFESHKEENSNWLKYPSEYHVDFQ<br>VKRNRKTEILDQLPKNKISTAKVDSTFSYSSGGKFDSTKGIGRTSSNSYSKTISYNQQNYD<br>TIASGKNNNWHVHWSVIANDLKYGGEVKNRNDELLFYRNTRIATVENPELSFASKYRYP<br>ALVRSGFNPEFLTYLSNEKSNEKTQFEVTYTRNQDILKNRPGIHYAPPILEKNKDGQRLIV<br>TYEVDWKNKTVKVVDKYSDDNKPYKEG<br><br>SEQ ID NO: 40<br>NSANKDSQDQTKKEHVDKAQQKEKRNVNDKDKNTPGPDDIGKNGKVTKRTVSEYDKE<br>TNILQNLQFDFIDDPTYDKNVLLVKKQGSIHSNLKFESHRNETNASWLKYPSEYHVDFQ<br>VQRNPKTEILDQLPKNKISTAKVDSTFSYSLGGKFDSTKGIGRTSSNSYSKSISYNQQNYD<br>TIASGKNNNRHVHWSVVANDLKYGNEIKNRNDEFLFYRNTRLSTVENPELSFASKYRYP<br>ALVRSGFNPEFLTYISNEKTNDKTRFEVTYTRNQDILKNKPGIHYGQPILEQNKDGQRFIV<br>VYEVDWKNKTVKVVEKYSDQNKPYKEG<br><br>SEQ ID NO: 41<br>NSANKDSQDQTKKEHVDKAQQKEKRNVNDKDKNTPGPDDIGKNGKVTKRTETVYDEK<br>TNILQNLQFDFIDDPTYDKNVLLVKKQGSIHSNLKFESHKEENNSSWLKYPSEYHVDFQV<br>KSNRKTEILDQLPKNKISTAKVDSTFSYNSGGKFDSVKGVGRTSSNSYSKTISYNQQNYD<br>TIASGKNNNWHVHWSVVANDLKYGGEVKNRNDDFLFYRNTRLSTVENPELSFASKYRY |

```
                            SEQUENCES

PALVRSGFNPEFLTYLSNEKSNEKTQFEVTYTRNQDVLKNKPGIHYAPPILEKNKDGQRL
IVTYEVDWKNKTVKVIDKYSDENKPYKEG

SEQ ID NO: 42
NSANKDSQDQTKKEHVDKAQQKEKRNVNDKDKNTPGPDDIGKNGKVTKRTVSEYDKE
TNILQNLQFDFIDDPTYDKNVLLVKKQGSIHSNLKFESHRNETNASWLKYPSEYHVDFQ
VQRNPKTEILDQLPKNKISTAKVDSTFSYSLGGKFDSTKGIGRTSSNSYSKSISYNQQNYD
TIASGKNNNRHVHWSVVANDLKYGNEIKNRNDEFLFYRNTRLSTVENPELSFASKYRYP
ALVRSGFNPEFLTYISNEKSNEKTRFEVTYTRNQDILKNKPGIHYGQPILEQNKDGQRFIV
VYEYEVDWKNKTVKVVEKYSDQNKPYKEG

SEQ ID NO: 43
NSANKDSQDQTKKEHVDKAQQKEKRNVNDKDKNTPGPDDIGKNGKVTKRTETVYDEK
TNILQNLQFDFIDDPTYDKNILLVKKQGSIFISNLKFESHKEENNSSWLKYPSEYHVDFQV
KRNRKTEILDQLPKNKISTAKVDSTFSYNSGGKFDSVKGVGRTSSNSYSKTISYNQQNYD
TIASGKNNNWHVHWSVVANDLKYGGEVKNRNDEFLFYRTTRLSTVENPELSFASKYRYP
PALVRSGFNPEFLTYLSNEKSNEKTQFEVTYTRNQDILKNKPGIHYAPPILEKNKDGQRLI
VTYEVDWKNKTVKVIDKYSDDNKPYKEG

SEQ ID NO: 44
NSAHKDSQDQNKKEHVDKSQQKDKRNVTNKDKNSTVPDDIGKNGKITKRTETVYDEK
TNILQNLQFDFIDDPTYDKNVLLVKKQGSIHSNLKFESHKEEKNSNWLKYPSEYHVDFQ
VKRNRKTEILDQLPKNKISTAKVDSTFSYSSGGKFDSTKGIGRTSSNSYSKTISYNQQNYD
TIASGKNNNWHVHWSVIANDLKYGGEVKNRNDELLFYRNTRIATVENPELSFASKYRYP
ALVRSGFNPEFLTYLSNEKSNEKTQFEVTYTRNQDILKNRPGIHYAPSILEKNKDGQRLIV
TYEVDWKNKTVKVVDKYSDDNKPYKEG

SEQ ID NO: 56
CATATGGACTCACAAGACCAGAACAAAAAGAACACGTCGATAAATCCCAACAAAA
AGATAAACGCAATGTCACCAATAAAGATAAAAATAGCACCGCACCGGATGACATTG
GCAAAAACGGTAAAATCACCAAACGTACCGAAACGGTGTATGATGAAAAAACGAAT
ATTCTGCAGAACCTGCAATTTGATTTCATCGATGACCCGACCTACGACAAAAATGTC
CTGCTGGTGAAAAAACAGGGCAGCATTCATTCTAACCTGAAATTCGAAAGTCACAA
AGAAGAGAAAAACTCCAACTGGCTGAAATATCCGTCAGAATACCATGTTGATTTCCA
GGTCAAACGTAATCGCAAAACCGAAATTCTGGACCAACTGCCGAAAAACAAAATCA
GTACCGCCAAAGTCGATAGTACGTTTTCCTATAGCTCTGGCGGTAAATTCGACTCTA
CCAAAGGCATCGGTCGTACGAGTTCCAACTCATACTCGAAAACCATCTCGTACAACC
AGCAAAACTACGATACGATCGCAAGCGGCAAAACAATAACTGGCATGTGCACTGG
TCTGTTATTGCTAACGATCTGAAATATGGCGGTGAAGTTAAAAATCGCAACGACGAA
CTGCTGTTTTACCGTAATACCCGCATCGCGACGGTTGAAAACCCGGAACTGTCATTC
GCGTCGAAATATCGTTACCCGGCCCTGGTCCGCAGCGGTTTTAATCCGGAATTCCTG
ACCTACCTGAGCAACGAAAAATCTAACGAAAAAACGCAGTTCGAAGTGACCTATAC
GCGTAATCAAGATATTCTGAAAAACCGCCCGGGCATTCACTACGCACCGCCGATCCT
GGAGAAAAACAAAGATGGTCAGCGCCTGATCGTCACCTATGAAGTGGATTGGAAAA
ACAAAACGGTTAAAGTGGTTGACAAATATTCCGATGACAACAAACCGTACAAAGAA
GGTTAATGACTCGAG

LukB sequences
SEQ ID NO: 15
MIKQLCKNITICSLALSTALTVFPATSYAKINSEIKQVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKNKMPVTVSEGFNPEFLAVMSHDKKDKGKSQFVVHYKRSMDEFKIDWNRHGFW
GYWSGENHVDKKEEKLSALYEVDWKTHNVKFVKVLNDNEKK SEQ ID NO: 16
MIKQVCKNITICSLALSTALTVFPASSYAEIKSKITTVSEKNLDGDTKMYTRTATTSDTEK
KISQSLQFNFLTEPNYDKETVFIKAKGTIGSGLKILNPNGYWNSTLRWPGSYSVSIQNVDD
NNNSTNVTDFAPKNQDESREVKYTYGYKTGGDFSINRGGLTGNITKEKNYSETISYQQPS
YRTLIDQPTTNKGVAWKVEAHSINNMGHDHTRQLTNDSDDRVKSEIFSLTRNGNLWAK
DNFTPKNKMPVTVSEGFNPEFLAVMSHDKNDGKSRFIVHYKRSMDDFKLDWNKHGF
WGYWSGENHVDQKEEKLSALYEVDWKTHDVKLIKTFNDKEKK SEQ ID NO: 17
MYTRTATTSDSQKNITQSLQFNFLTEPNYDKETVFIKAKGTIGSGLRILDPNGYWNSTLR
WPGSYSVSIQNVDDNNNTNVTDFAPKNQDESREVKYTYGYKTGGDFSINRGGLTGNITK
ESNYSETTSYQQPSYRTLLDQSTSHKGVGWKVEAHLINNMGHDHTRQLTNDSDNRTKSE
IFSLTRNGNLWAKDNFTPKDKMPVTVSEGFNPEFLAVMSHDKKDKGKSQFVVHYKRSM
DEFKIDWNRHGFWGYWSGENHVDKKEEKLSALYEVDWKTHNVKFVKVLNDNEKK SEQ ID NO: 18
MIKQVCKNITICSLALSTALTIFPASSYAKINSEIKQVSEKNLDGETKMYTRTATTSDSQK
NITQSLQFNFLTEKNYDKETVFIKAKGTIGSGLRILEPNGYWNSTLRWPGSYSVSIQNVD
DNNNTNVTDFAPKNQDESREVKYTYGYKTGGDFSINQGGLTGNITKESNYSETTSYQQPS
YRTLIDQPTTNKGVAWKVEAHLINNMGHDHTRQLTNDSDDRVKSEIFSLTRNGNLWAK
```

DNFTPKNKMPVTVSEGFNPEFLAVMSHDKKDEGKSKFVVHYKRSMDEFKIDWNKHGF
WGYWSGENHVDKKEEKLSALYEVDWKTHNVKFIKVLNDKEKK

SEQ ID NO: 19
MIKQVCKNITICSLALSTALTVFPASSYAEIKSKITTVSEKNLDGDTKMYTRTATTSDTEK
KISQSLQFNFLTEPNYDKETVFIKAKGTIGSGLKILNPNGYWNSTLTWPGSYSVSIQNVDD
NNNSTNVTDFAPKNQDESREVKYTYGYKTGGDFSINRGGLTGNITKEKNYSETTSYQQPS
YRTLIDQPTTNKGVAWKVEAHSINNMGHDHTRQLTNDSDDRVKSEIFSLTRNGNLWAK
DNFTPKNKMPVTVSEGFNPEFLAVMSHDKNDGKSRFIVHYKRSMDDFKLDWNKHGF
WGYWSGENHVDQKEEKLSALYEVDWKTHDVKLIKTINDKEQK

SEQ ID NO: 20
MIKQLCKNITICTLALSTTFTVLPATSFAKINSEIKQVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKDKMPVTVSEGFNPEFLAVMSHDKKDKGKSQFVVHYKRSMDEFKIDWNRHGFW
GYWSGENHVDEKEEKLSALYEVDWKTHNVKFVKVLNDNEKK

SEQ ID NO: 21
MIKQVCKNITICSLALSTALTVFPASSYAEIKSKITTVSEKNLDGDTKMYTRTATTSDTEK
KISQSLQFNFLTEPNYDKETVFIKAKGTIGSGLKILNPNGYWNSTLRWPGSYSVSIQNVDD
NNNSTNVTDFAPKNQDESREVKYTYGYKTGGDFSINRGGLTGNITKEKNYSETTSYQQPS
YRTLIDQPTTNKGVAWKVEAHSINNMGHDHTRQLTNDSDDRVKSEIFSLTRNGNLWAK
DNFTPKNKMPVTVSEGFNPEFLAVMSHDKNDGKSRFIVHYKRSMDDFKLDWNKHGF
WGYWSGENHVDQKEEKLSALYEVDWKTHDVKLIKTINDKEQK

SEQ ID NO: 22
MIKQLYKNITICSLAISTALTVFPATSYAKINSEIKAVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKDKMPVTVSEGFNPEFLAVMSHDKKDKGKSQFVVHYKRSMDEFKIDWNRHGFW
GYWSGENHVDKKEEKLSALYEVDWKTHDVKFVKVLNDNEKK

SEQ ID NO: 23
MIKQLYKNITICTLALSTTFTVLPATSYAKINSEIKAVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKNKMPVTVSEGFNPEFLAVMSHDKKDEGKSKFVVHYKRSMDEFKIDWNRHGFW
GYWSGENHVDKKEEKLSALYEVDWKTHNVKFVKVLNDNEKK

SEQ ID NO: 24
MIKQLYKNITICSLTISTALTVFPATSYAKINSEIKAVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLPGNITKESNYSETISYQQPSY
RTLLDQSTSHKGVGWKVEAHLINNMGHDHTRQLTNDSDNRTKSEIFSLTRNGNLWAKD
NFTPKNKMPVTVSEGFNPEFLAVMSHDKKDEGKSKFVVHYKRSMDEFKIDWNRHGFW
GYWSGENHVDKKEEKLSALYEVDWKTHDVKFVKVLNDNEKK

SEQ ID NO: 25
MIKQLCKNITICTLALSTTFTVLPATSFAKINSEIKQVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKNKMPVTVSEGFNPEFLAVMSHDKKDEGKSKFVVHYKRSMDEFKIDWNRHGFW
GYWSGENHVDKKEEKLSALYEVDWKTHNVKFVKVLNDNEKK

SEQ ID NO: 26
MIKQLCKNITICTLALSTTFTVLPATSFAKINSEIKQVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKDKMPVTVSEGFNPEFLAVMSHDKKDKGKSQFVVHYKRSMDEFKIDWNRHGFW
GYWSGENHVDKKEEKLSALYEVDWKTHNVKFVKVLNDNEKK

SEQ ID NO: 27
MIKQLCKNITICTLALSTTFTVLPATSFAKINSEIKQVSEKNLDGDTKMYTRTATTSDSQK
NITQSLQFNFLTEPNYDKETVFIKAKGTIGSGLRILDPNGYWNSTLRWPGSYSVSIQNVDD
NNNTNVTDFAPKNQDESREVKYTYGYKTGGDFSINRGGLTGNITKESNYSETISYQQPSY
RTLLDQSTSHKGVGWKVEAHLINNMGHDHTRQLTNDSDNRTKSEIFSLTRNGNLWAKD
NFTPKDKMPVTVSEGFNPEFLAVMSHDKKDKGKSQFVVHYKRSMDEFKIDWNRHGFW
GYWSGENHVDKKEEKLSALYEVDWKTHNVKFVKVLNDNEKK

SEQUENCES

SEQ ID NO: 29
KINSEIKQVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKNKMPVTVSEGFNPEFLAVMSH
DKKDKGKSQFVVHYKRSMDEFKIDWNRHGFWGYWSGENHVDKKEEKLSALYEVDWK
THNVKFVKVLNDNEKK

SEQ ID NO: 31 (encoding SEQ ID NO: 27)
ATGATTAAAC AACTATGTAA AAATATCACA ATTTGTACGT TAGCACTATC
GACTACTTTC ACTGTATTAC CAGCTACTTC ATTTGCAAAG ATTAATTCTG
AAATCAAACA AGTTTCTGAG AAGAATCTTG ATGGTGATAC TAAAATGTAT
ACACGTACAG CTACAACAAG TGATAGTCAA AAAAATATTA CTCAAAGCTT
ACAATTTAAT TTCTTAACTG AACCTAATTA TGATAAAGAA ACAGTATTTA
TTAAAGCAAA AGGTACAATT GGTAGTGGTT TGAGAATTTT AGACCCAAAT
GGTTATTGGA ATAGTACATT AAGATGGCCT GGATCTTATT CAGTTTCAAT
TCAAAATGTT GATGACAACA ACAATACAAA TGTGACTGAC TTTGCACCAA
AAAATCAGGA TGAATCAAGA GAAGTTAAAT ATACGTATGG TTATAAAACA
GGTGGAGATT TTTCGATTAA TCGTGGAGGC TTAACTGGAA ATATTACAAA
AGAGAGTAAT TATTCAGAGA CGATTAGTTA TCAACAACCA TCATATCGTA
CATTACTTGA TCAATCTACG TCACATAAAG GTGTAGGTTG GAAAGTAGAA
GCACATTTGA TAAATAATAT GGGACATGAC CATACGAGAC AATTAACTAA
TGATAGTGAT AATAGAACTA AAAGTGAAAT TTTTTCTTTA ACACGAAATG
GAAATTTATG GGCGAAAGAT AATTTCACAC CTAAAGACAA AATGCCTGTA
ACTGTGTCTG AAGGGTTTAA TCCAGAATTT TTAGCTGTTA TGTCACATGA
TAAAAAAGAC AAAGGTAAAT CACAATTTGT TGTTCATTAT AAAAGATCAA
TGGATGAGTT TAAAATAGAT TGGAATCGCC ATGGTTTCTG GGGCTATTGG
TCTGGTGAAA ACCATGTAGA TAAAAAAGAA GAAAAATTAT CAGCATTATA
TGAAGTTGAT TGGAAGACAC ATAATGTGAA GTTTGTAAAA GTACTTAATG
ATAATGAAAA GAAATAA SEQ ID NO: 45
EIKSKITTVSEKNLDGDTKMYTRTATTSDTEKKISQSLQFNFLTEPNYDKETVFIKAKGTI
GSGLKILNPNGYWNSTLRWPGSYSVSIQNVDDNNNSTNVTDFAPKNQDESREVKYTYG
YKTGGDFSINRGGLTGNITKEKNYSETISYQQPSYRTLIDQPTTNKGVAWKVEAHSINNM
GHDHTRQLTNDSDDRVKSEIFSLTRNGNLWAKDNFTPKNKMPVTVSEGFNPEFLAVMS
HDKNDKGKSRFIVHYKRSMDDFKLDWNKHGFWGYWSGENHVDQKEEKLSALYEVDW
KTHDVKLIKTFNDKEKK SEQ ID NO: 46
KINSEIKQVSEKNLDGETKMYTRTATTSDSQKNITQSLQFNFLTEKNYDKETVFIKAKGTI
GSGLRILEPNGYWNSTLRWPGSYSVSIQNVDDNNNTNVTDFAPKNQDESREVKYTYGY
KTGGDFSINQGGLTGNITKESNYSETISYQQPSYRTLIDQPTTNKGVAWKVEAHLINNMG
HDHTRQLTNDSDDRVKSEIFSLTRNGNLWAKDNFTPKNKMPVTVSEGFNPEFLAVMSH
DKKDEGKSKFVVHYKRSMDEFKIDWNKHGFWGYWSGENHVDKKEEKLSALYEVDWK
THNVKFIKVLNDKEKK SEQ ID NO: 47
EIKSKITTVSEKNLDGDTKMYTRTATTSDTEKKISQSLQFNFLTEPNYDKETVFIKAKGTI
GSGLKILNPNGYWNSTLTWPGSYSVSIQNVDDNNNSTNVTDFAPKNQDESREVKYTYG
YKTGGDFSINRGGLTGNITKEKNYSETISYQQPSYRTLIDQPTTNKGVAWKVEAHSINNM
GHDHTRQLTNDSDDRVKSEIFSLTRNGNLWAKDNFTPKNKMPVTVSEGFNPEFLAVMS
HDKNDKGKSRFIVHYKRSMDDFKLDWNKHGFWGYWSGENHVDQKEEKLSALYEVDW
KTHDVKLIKTINDKEQK SEQ ID NO: 48
KINSEIKQVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMMG
HDHTRQLTNDSDNRTKSEIFSLTRNGNLWAKDNFTPKDKMPVTVSEGFNPEFLAVMSH
DKKDKGKSQFVVHYKRSMDEFKIDWNRHGFWGYWSGENHVDEKEEKLSALYEVDWK
THNVKFVKVLNDNEKK SEQ ID NO: 49
EIKSKITTVSEKNLDGDTKMYTRTATTSDTEKKISQSLQFNFLTEPNYDKETVFIKAKGTI
GSGLKILNPNGYWNSTLRWPGSYSVSIQNVDDNNNSTNVTDFAPKNQDESREVKYTYG
YKTGGDFSINRGGLTGNITKEKNYSETISYQQPSYRTLIDQPTTNKGVAWKVEAHSINNM
GHDHTRQLTNDSDDRVKSEIFSLTRNGNLWAKDNFTPKNKMPVTVSEGFNPEFLAVMS
HDKNDKGKSRFIVHYKRSMDDFKLDWNKHGFWGYWSGENHVDQKEEKLSALYEVDW
KTHDVKLIKTINDKEQK SEQ ID NO: 50
KINSEIKAVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKDKMPVTVSEGFNPEFLAVMSH

| SEQUENCES |
| --- |

DKKDKGKSQFVVHYKRSMDEFKIDWNRHGFWGYWSGENHVDKKEEKLSALYEVDWK
THDVKFVKVLNDNEKK

SEQ ID NO: 51
KINSEIKAVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKNKMPVTVSEGFNPEFLAVMSH
DKKDEGKSKFVVHYKRSMDEFKIDWNRHGFWGYWSGENHVDKKEEKLSALYEVDWK
THNVKFVKVLNDNEKK

SEQ ID NO: 52
KINSEIKAVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLPGNITKESNYSETISYQQPSYRTLLDQSTSHKGVGWKVEAHLINNMG
HDHTRQLTNDSDNRTKSEIFSLTRNGNLWAKDNFTPKNKMPVTVSEGFNPEFLAVMSH
DKKDEGKSKFVVHYKRSMDEFKIDWNRHGFWGYWSGENHVDKKEEKLSALYEVDWK
THDVKFVKVLNDNEKK

SEQ ID NO: 53
KINSEIKQVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKNKMPVTVSEGFNPEFLAVMSH
DKKDEGKSKFVVHYKRSMDEFKIDWNRHGFWGYWSGENHVDKKEEKLSALYEVDWK
THNVKFVKVLNDNEKK

SEQ ID NO: 54
KINSEIKQVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKDKMPVTVSEGFNPEFLAVMSH
DKKDKGKSQFVVHYKRSMDEFKIDWNRHGFWGYWSGENHVDKKEEKLSALYEVDWK
THNVKFVKVLNDNEKK

SEQ ID NO: 55
KINSEIKQVSEKNLDGDTKMYTRTATTSDSQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKDKMPVTVSEGFNPEFLAVMSH
DKKDKGKSQFVVHYKRSMDEFKIDWNRHGFWGYWSGENHVDKKEEKLSALYEVDWK
THNVKFVKVLNDNEKK

SEQ ID NO: 57
CATATGAAAATCAACTCAGAAATCAAACAAGTCTCCGAAAAAAACCTGGATGGCGA
CACCAAAATGTATACCCGCACGGCGACCACGAGCGACTCGCAGAAAAACATCACGC
AGAGCCTGCAATTTAATTTCCTGACCGAACCGAACTACGATAAAGAAACGGTGTTCA
TCAAAGCAAAAGGCACCATCGGCTCAGGTCTGCGTATTCTGGACCCGAATGGCTACT
GGAACTCGACCCTGCGCTGGCCGGGTAGCTATTCTGTCAGTATTCAGAATGTGGATG
ACAACAATAACACCAACGTGACGGATTTTGCTCCGAAAAATCAAGACGAAAGTCGT
GAAGTTAAATATACCTACGGCTATAAAACGGGCGGTGATTTCTCTATCAATCGCGGC
GGTCTGACCGGTAATATTACGAAAGAATCGAACTATAGCGAAACCATCTCCTACCAG
CAACCGTCATATCGTACCCTGCTGGATCAGTCCACGTCACATAAAGGCGTGGGTTGG
AAAGTTGAAGCGCACCTGATCAATAACATGGGCCATGATCACACCCGTCAACTGAC
GAATGATAGCGACAACCGCACGAAATCTGAAATTTTTAGTCTGACCCGCAATGGTAA
CCTGTGGGCGAAAGATAACTTCACGCCGAAAGACAAAATGCCGGTCACCGTGTCCG
AAGGCTTTAATCCGGAATTCCTGGCCGTCATGTCTCATGATAAAAAAGACAAAGGTA
AAAGTCAGTTTGTGGTTCACTACAAACGTTCCATGGATGAATTCAAAATCGACTGGA
ACCGCCATGGCTTCTGGGGTTACTGGAGCGGTGAAAACCACGTTGATAAAAAAGAA
GAAAAACTGTCTGCACTGTATGAAGTTGACTGGAAAACCCATAACGTCAAATTCGTT
AAAGTCCTGAACGATAACGAGAAAAAATAATGACTCGAG

HlgB-LukB fusion sequence
SEQ ID NO: 58
AEGKITPVSVKKVDDKVTLYKTTATADSDQKNITQSLQFNFLTEPNYDKETVFIKAKGTI
GSGLRILDPNGYWNSTLRWPGSYSVSIQNVDDNNNTNVTDFAPKNQDESREVKYTYGY
KTGGDFSINRGGLTGNITKESNYSETISYQQPSYRTLLDQSTSHKGVGWKVEAHLINNMG
HDHTRQLTNDSDNRTKSEIFSLTRNGNLWAKDNFTPKDKMPVTVSEGFNPEFLAVMSH
DKKDKGKSQFVVHYKRSMDEFKIDWNRHGFWGYWSGENHVDKKEEKLSALYEVDWK
THNVKFVKVLNDNEKK Sequence of the p15a origin used to construct P15a origin
LukB pET24a(+)
SEQ ID NO: 59
GCGCTAGCGGAGTGTATACTGGCTTACTATGTTGGCACTGATGAGGGTGTCAGTGAA
GTGCTTCATGTGGCAGGAGAAAAAGGCTGCACCGGTGCGTCAGCAGAATATGTGA
TACAGGATATATTCCGCTTCCTCGCTCACTGACTCGCTACGCTCGGTCGTTCGACTGC -continued

| SEQUENCES |
|---|
| GGCGAGCGGAAATGGCTTACGAACGGGGCGGAGATTTCCTGGAAGATGCCAGGAAG<br>ATACTTAACAGGGAAGTGAGAGGGCCGCGGCAAAGCCGTTTTTCCATAGGCTCCGCC<br>CCCCTGACAAGCATCACGAAATCTGACGCTCAAATCAGTGGTGGCGAAACCCGACA<br>GGACTATAAAGATACCAGGCGTTTCCCCTGGCGGCTCCCTCGTGCGCTCTCCTGTTC<br>CTGCCTTTCGGTTTACCGGTGTCATTCCGCTGTTATGGCCGCGTTTGTCTCATTCCAC<br>GCCTGACACTCAGTTCCGGGTAGGCAGTTCGCTCCAAGCTGGACTGTATGCACGAAC<br>CCCCCGTTCAGTCCGACCGCTGCGCCTTATCCGGTAACTATCGTCTTGAGTCCAACCC<br>GGAAAGACATGCAAAAGCACCACTGGCAGCAGCCACTGGTAATTGATTTAGAGGAG<br>TTAGTCTTGAAGTCATGCGCCGGTTAAGGCTAAACTGAAAGGACAAGTTTTGGTGAC<br>TGCGCTCCTCCAAGCCAGTTACCTCGGTTCAAAGAGTTGGTAGCTCAGAGAACCTTC<br>GAAAAACCGCCCTGCAAGGCGGTTTTTTCGTTTTCAGAGCAAGAGATTACGCGCAGA<br>CCAAAACGATCTCAAGAAGATCATCTTATTAATCAGATAAAATATTTCTAGATTTCA<br>GTGCAATTTATCTCTTCAAATGTAGCACCTGAAGTCAGCCCCATACGATATAAGTTG<br>T |

---

What is claimed is:

1. An isolated mutant staphylococcal leukocidin subunit polypeptide comprising a wild-type staphylococcal LukA subunit, a wild-type staphylococcal LukB subunit, or a wild-type staphylococcal LukAB dimer, except for having one or more amino acid substitutions at conserved residues in the LukA subunit, the LukB subunit, or in the LukAB dimer,
comprising a mutation in the LukAB dimer/dimer interface region,
wherein the mutation in the LukAB dimer/dimer interface region is at a LukB position corresponding to R23 of SEQ ID NO: 29, and
wherein the LukB position corresponding to R23 of SEQ ID NO: 29 is substituted with glutamate (E).

2. The mutant subunit polypeptide of claim 1, further comprising a mutation at a LukA position corresponding to D39 of SEQ ID NO: 28, a LukA position corresponding to D75 of SEQ ID NO: 28, a LukA position corresponding to K138 of SEQ ID NO: 28, a LukA position corresponding to D197 of SEQ ID NO: 28, a LukB position corresponding to K12 of SEQ ID NO: 29, a LukB position corresponding to K19 of SEQ ID NO: 29, a LukB position corresponding to K58 of SEQ ID NO: 29, a LukB position corresponding to E112 of SEQ ID NO: 29, a LukB position corresponding to K218 of SEQ ID NO: 29, or any combination thereof.

3. The mutant subunit polypeptide of claim 1, further comprising a mutation at a LukA position corresponding to D39 of SEQ ID NO: 28,
wherein the LukA position corresponding to D39 of SEQ ID NO: 28 is substituted with alanine (A) or arginine (R).

4. The mutant subunit polypeptide of claim 1, further comprising a mutation at a LukA position corresponding to D39 of SEQ ID NO: 28,
wherein the LukA position corresponding to D39 of SEQ ID NO: 28 is substituted with alanine (A).

5. The mutant subunit polypeptide of claim 2, wherein the LukA position corresponding to D75 of SEQ ID NO: 28 is substituted with alanine (A).

6. The mutant subunit polypeptide of claim 2, wherein the LukA position corresponding to K138 of SEQ ID NO: 28 is substituted with alanine (A).

7. The mutant subunit polypeptide of claim 2, wherein the LukA position corresponding to D197 of SEQ ID NO: 28 is substituted with alanine (A) or lysine (K).

8. The mutant subunit polypeptide of claim 2, wherein the LukB position corresponding to K12 of SEQ ID NO: 29 is substituted with alanine (A) and/or the LukB position corresponding to K19 of SEQ ID NO: 29 is substituted with alanine (A).

9. The mutant subunit polypeptide of claim 2, comprising a triple-mutant LukB, wherein the LukB position corresponding to K12 of SEQ ID NO: 29 is substituted with alanine (A), the LukB position corresponding to K19 of SEQ ID NO: 29 is substituted with alanine (A), and the LukB position corresponding to R23 of SEQ ID NO: 29 is substituted with glutamate (E).

10. The mutant subunit polypeptide of claim 2, wherein the LukB position corresponding to K58 of SEQ ID NO: 29 is substituted with alanine (A) or glutamate (E).

11. The mutant subunit polypeptide of claim 2, wherein the LukB position corresponding to E112 of SEQ ID NO: 29 is substituted with alanine (A).

12. The mutant subunit polypeptide of claim 2, wherein the LukB position corresponding to K218 of SEQ ID NO: 29 is substituted with alanine (A).

13. The mutant subunit polypeptide of claim 1, which is less toxic in a neutrophil toxicity assay compared to the corresponding wild-type leukocidin subunit.

14. The mutant subunit polypeptide of claim 2, wherein the wild-type LukA subunit comprises an amino acid sequence selected from the group consisting of SEQ ID NO: 32, SEQ ID NO: 33, SEQ ID NO: 35, and SEQ ID NO: 41.

15. The mutant subunit polypeptide of claim 1, wherein the wild-type LukB subunit comprises an amino acid sequence selected from the group consisting of SEQ ID NO: 17, SEQ ID NO: 49, SEQ ID NO: 53, and SEQ ID NO: 54.

16. A polypeptide complex comprising a mutant LukAB dimer of claim 1,
wherein the mutant LukAB dimer comprises both a mutant LukA subunit and a mutant LukB subunit, and
wherein the LukAB dimer comprises LukB R23E.

17. The polypeptide complex of claim 16, wherein the LukAB dimer comprises LukA D39A or LukA D39R.

18. The polypeptide complex of claim 17 comprising LukA D39A and LukB R23E.

19. A composition comprising the mutant subunit polypeptide of claim 3, and a carrier.

20. The mutant subunit polypeptide of claim 2, wherein the wild-type LukB subunit comprises an amino acid sequence selected from the group consisting of SEQ ID NO: 17, SEQ ID NO: 49, SEQ ID NO: 53, and SEQ ID NO: 54.

21. The mutant subunit polypeptide of claim 2, wherein the wild-type LukA subunit comprises an amino acid sequence selected from the group consisting of SEQ ID NO: 32, SEQ ID NO: 33, SEQ ID NO: 35, and SEQ ID NO: 41, and wherein the wild-type LukB subunit comprises an amino acid sequence selected from the group consisting of SEQ ID NO: 17, SEQ ID NO: 49, SEQ ID NO: 53, and SEQ ID NO: 54.

* * * * *

SEQUENCE LISTING

<160> NUMBER OF SEQ ID NOS: 59

<210> SEQ ID NO 1
<211> LENGTH: 351
<212> TYPE: PRT
<213> ORGANISM: Staphylococcus aureus
<220> FEATURE:
<221> NAME/KEY: SIMILAR
<222> LOCATION: (1)..(351)
<223> OTHER INFORMATION: consensus majority LukA pro-peptide sequence

<400> SEQUENCE: 1

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Glu Lys Arg Asn Val Thr Asn Lys Asp Lys Asn Ser Thr Xaa Pro
    50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

```
Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 2
<211> LENGTH: 351
<212> TYPE: PRT
<213> ORGANISM: Staphylococcus aureus

<400> SEQUENCE: 2

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Asp Lys Arg Asn Val Thr Asn Lys Asp Lys Asn Ser Thr Ala Pro
    50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240
```

```
Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
                340                 345                 350

<210> SEQ ID NO 3
<211> LENGTH: 351
<212> TYPE: PRT
<213> ORGANISM: Staphylococcus aureus

<400> SEQUENCE: 3

Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45

Lys Glu Lys Arg Asn Val Asn Asp Lys Asp Lys Asn Thr Pro Gly Pro
    50                  55                  60

Asp Asp Ile Gly Lys Asn Gly Lys Val Thr Lys Arg Thr Val Ser Glu
65                  70                  75                  80

Tyr Asp Lys Glu Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
        115                 120                 125

Ala Ser Trp Leu Lys Tyr Pro Ser Glu Tyr His Val Asp Phe Gln Val
    130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
        195                 200                 205

Gly Lys Asn Asn Asn Arg His Val His Trp Ser Val Val Ala Asn Asp
    210                 215                 220

Leu Lys Tyr Gly Asn Glu Ile Lys Asn Arg Asn Asp Glu Phe Leu Phe
225                 230                 235                 240

Tyr Arg Asn Thr Arg Leu Ser Thr Val Glu Asn Pro Glu Leu Ser Phe
                245                 250                 255
```

```
Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Ser Asn Glu Lys Thr Arg
            275                 280                 285

Phe Glu Val Thr Tyr Thr Arg Asn Gln Asp Ile Leu Lys Asn Lys Pro
            290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
            340                 345                 350

<210> SEQ ID NO 4
<211> LENGTH: 350
<212> TYPE: PRT
<213> ORGANISM: Staphylococcus aureus

<400> SEQUENCE: 4

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Glu Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
            115                 120                 125

Ser Asn Trp Leu Lys Tyr Pro Ser Glu Tyr His Val Asp Phe Gln Val
130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
            195                 200                 205

Gly Lys Asn Asn Asn Trp His Val His Trp Ser Val Ile Ala Asn Asp
210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270
```

```
Glu Phe Leu Thr Tyr Leu Ser Asn Glu Lys Ser Asn Glu Lys Thr Gln
            275                 280                 285

Phe Glu Val Thr Tyr Thr Arg Asn Gln Asp Ile Leu Lys Asn Arg Pro
290                 295                 300

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asn Lys Ser Phe Arg Glu Gly
                340                 345                 350

<210> SEQ ID NO 5
<211> LENGTH: 350
<212> TYPE: PRT
<213> ORGANISM: Staphylococcus aureus

<400> SEQUENCE: 5

Met Lys Asn Lys Lys Arg Val Leu Ile Ala Ser Ser Leu Ser Cys Ala
1               5                   10                  15

Ile Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Ala Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
                100                 105                 110

Ser Ile His Ser Asn Leu Lys Phe Glu Ser His Lys Glu Glu Lys Asn
            115                 120                 125

Ser Asn Trp Leu Lys Tyr Pro Ser Glu Tyr His Val Asp Phe Gln Val
        130                 135                 140

Lys Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285
```

```
Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
                325                 330                 335

Val Val Asp Lys Tyr Thr Asp Asn Lys Ser Phe Arg Glu Gly
            340                 345                 350

<210> SEQ ID NO 6
<211> LENGTH: 350
<212> TYPE: PRT
<213> ORGANISM: Staphylococcus aureus

<400> SEQUENCE: 6

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Glu Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Val Lys Lys Gln Gly
            100                 105                 110

Ser Ile His Ser Asn Leu Lys Phe Glu Ser His Lys Glu Glu Lys Asn
                115                 120                 125

Ser Asn Trp Leu Lys Tyr Pro Ser Glu Tyr His Val Asp Phe Gln Val
            130                 135                 140

Lys Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300
```

Gly Ile His Tyr Ala Pro Pro Ile Leu Glu Lys Asn Lys Glu Gly Gln
305                 310                 315                 320

Arg Leu Ile Val Thr Tyr Glu Val Asp Trp Lys Asn Lys Thr Val Lys
            325                 330                 335

Val Val Asp Lys Tyr Ser Asp Asn Lys Ser Phe Arg Glu Gly
            340                 345                 350

<210> SEQ ID NO 7
<211> LENGTH: 351
<212> TYPE: PRT
<213> ORGANISM: Staphylococcus aureus

<400> SEQUENCE: 7

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Asp Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
290                 295                 300

Gly Ile His Tyr Ala Pro Pro Ile Leu Glu Lys Asn Lys Asp Gly Gln
305                 310                 315                 320

```
Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 8
<211> LENGTH: 351
<212> TYPE: PRT
<213> ORGANISM: Staphylococcus aureus

<400> SEQUENCE: 8

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
                20                  25                  30

Asp Ser Gln Asp Gln Asn Lys Lys Glu His Val Asp Lys Ser Gln Gln
            35                  40                  45

Lys Asp Lys Arg Asn Val Thr Asn Lys Asp Lys Asn Ser Thr Val Pro
50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Lys Tyr Asp Thr Ile Ala Ile
        195                 200                 205

Gly Lys Asn Asn Asn Trp His Val His Trp Ser Val Ile Ala Asn Asp
210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335
```

Val Val Asp Lys Tyr Ser Asp Asp Asn Lys Pro Tyr Lys Glu Gly
            340                 345                 350

<210> SEQ ID NO 9
<211> LENGTH: 351
<212> TYPE: PRT
<213> ORGANISM: Staphylococcus aureus

<400> SEQUENCE: 9

Met Lys Asn Lys Lys Arg Val Leu Ile Ala Ser Ser Leu Ser Cys Ala
1               5                   10                  15

Ile Leu Leu Leu Ser Ala Ala Thr Thr Gln Ala Asn Ser Ala His Lys
            20                  25                  30

Asp Ser Gln Asp Gln Asn Lys Lys Glu His Val Asp Lys Ser Gln Gln
        35                  40                  45

Lys Asp Lys Arg Asn Val Thr Asn Asp Lys Asn Ser Thr Ala Pro
    50                  55                  60

Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

```
<210> SEQ ID NO 10
<211> LENGTH: 351
<212> TYPE: PRT
<213> ORGANISM: Staphylococcus aureus

<400> SEQUENCE: 10
```

| | | | | | | | | | | | | | | |
|---|---|---|---|---|---|---|---|---|---|---|---|---|---|---|
| Met | Lys | Asn | Lys | Lys | Arg | Val | Phe | Ile | Ala | Ser | Ser | Leu | Ser | Cys | Ala |
| 1 | | | | 5 | | | | | 10 | | | | | 15 | |

Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45

Lys Glu Lys Arg Asn Val Asn Asp Lys Asp Lys Asn Thr Pro Gly Pro
    50                  55                  60

Asp Asp Ile Gly Lys Asn Gly Lys Val Thr Lys Arg Thr Val Ser Glu
65                  70                  75                  80

Tyr Asp Lys Glu Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
        115                 120                 125

Ala Ser Trp Leu Lys Tyr Pro Ser Glu Tyr His Val Asp Phe Gln Val
130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
        195                 200                 205

Gly Lys Asn Asn Asn Arg His Val His Trp Ser Val Val Ala Asn Asp
210                 215                 220

Leu Lys Tyr Gly Asn Glu Ile Lys Asn Arg Asn Asp Glu Phe Leu Phe
225                 230                 235                 240

Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Thr Asn Asp Lys Thr Arg
        275                 280                 285

Phe Glu Val Thr Tyr Thr Arg Asn Gln Asp Ile Leu Lys Asn Lys Pro
290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
            340                 345                 350

```
<210> SEQ ID NO 11
<211> LENGTH: 351
<212> TYPE: PRT
<213> ORGANISM: Staphylococcus aureus
```

<400> SEQUENCE: 11

Met Lys Asn Lys Lys Arg Val Phe Ile Ala Ser Ser Leu Ser Cys Ala
1               5                   10                  15

Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45

Lys Glu Lys Arg Asn Val Asn Asp Lys Asp Lys Asn Thr Pro Gly Pro
    50                  55                  60

Asp Asp Ile Gly Lys Asn Gly Lys Val Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Asn Asn
        115                 120                 125

Ser Ser Trp Leu Lys Tyr Pro Ser Glu Tyr His Val Asp Phe Gln Val
130                 135                 140

Lys Ser Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Asn Ser Gly Gly
                165                 170                 175

Lys Phe Asp Ser Val Lys Gly Val Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Val Ala Asn Asp
210                 215                 220

Leu Lys Tyr Gly Gly Glu Val Lys Asn Arg Asn Asp Asp Phe Leu Phe
225                 230                 235                 240

Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Val Leu Lys Asn Lys Pro
290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Ile Asp Lys Tyr Ser Asp Glu Asn Lys Pro Tyr Lys Glu Gly
            340                 345                 350

<210> SEQ ID NO 12
<211> LENGTH: 351
<212> TYPE: PRT
<213> ORGANISM: Staphylococcus aureus

<400> SEQUENCE: 12

Met Lys Asn Lys Lys Arg Val Phe Ile Ala Ser Ser Leu Ser Cys Val
1               5                   10                  15

```
Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45

Lys Glu Lys Arg Asn Val Asn Asp Lys Asp Lys Asn Thr Pro Gly Pro
 50                  55                  60

Asp Asp Ile Gly Lys Asn Gly Lys Val Thr Lys Arg Thr Val Ser Glu
 65                  70                  75                  80

Tyr Asp Lys Glu Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Arg Asn Glu Thr Asn
            115                 120                 125

Ala Ser Trp Leu Lys Tyr Pro Ser Glu Tyr His Val Asp Phe Gln Val
130                 135                 140

Gln Arg Asn Pro Lys Thr Glu Ile Leu Asp Gln Leu Pro Lys Asn Lys
145                 150                 155                 160

Ile Ser Thr Ala Lys Val Asp Ser Thr Phe Ser Tyr Ser Leu Gly Gly
                165                 170                 175

Lys Phe Asp Ser Thr Lys Gly Ile Gly Arg Thr Ser Ser Asn Ser Tyr
            180                 185                 190

Ser Lys Ser Ile Ser Tyr Asn Gln Gln Asn Tyr Asp Thr Ile Ala Ser
            195                 200                 205

Gly Lys Asn Asn Asn Arg His Val His Trp Ser Val Val Ala Asn Asp
210                 215                 220

Leu Lys Tyr Gly Asn Glu Ile Lys Asn Arg Asn Asp Glu Phe Leu Phe
225                 230                 235                 240

Tyr Arg Asn Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Ile Ser Asn Glu Lys Ser Asn Glu Lys Thr Arg
            275                 280                 285

Phe Glu Val Thr Tyr Thr Arg Asn Gln Asp Ile Leu Lys Asn Lys Pro
290                 295                 300

Gly Ile His Tyr Gly Gln Pro Ile Leu Glu Gln Asn Lys Asp Gly Gln
305                 310                 315                 320

Arg Phe Ile Val Val Tyr Glu Val Asp Trp Lys Asn Lys Thr Val Lys
                325                 330                 335

Val Val Glu Lys Tyr Ser Asp Gln Asn Lys Pro Tyr Lys Glu Gly
            340                 345                 350
```

<210> SEQ ID NO 13
<211> LENGTH: 351
<212> TYPE: PRT
<213> ORGANISM: Staphylococcus aureus

<400> SEQUENCE: 13

```
Met Lys Asn Lys Lys Arg Val Phe Ile Ala Ser Ser Leu Ser Cys Ala
 1               5                  10                  15

Leu Leu Leu Leu Ser Ala Ala Asn Thr Glu Ala Asn Ser Ala Asn Lys
            20                  25                  30

Asp Ser Gln Asp Gln Thr Lys Lys Glu His Val Asp Lys Ala Gln Gln
        35                  40                  45
```

```
Lys Glu Lys Arg Asn Val Asn Asp Lys Asp Lys Asn Thr Pro Gly Pro
         50                  55                  60

Asp Asp Ile Gly Lys Asn Gly Lys Val Thr Lys Arg Thr Glu Thr Val
 65                  70                  75                  80

Tyr Asp Glu Lys Thr Asn Ile Leu Gln Asn Leu Gln Phe Asp Phe Ile
                 85                  90                  95

Asp Asp Pro Thr Tyr Asp Lys Asn Ile Leu Leu Val Lys Lys Gln Gly
            100                 105                 110

Ser Ile His Ser Asn Leu Lys Phe Glu Ser His Lys Glu Glu Asn Asn
        115                 120                 125

Ser Ser Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Asn Ser Gly Gly
                165                 170                 175

Lys Phe Asp Ser Val Lys Gly Val Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Val Ala Asn Asp
    210                 215                 220

Leu Lys Tyr Gly Gly Glu Val Lys Asn Arg Asn Asp Glu Phe Leu Phe
225                 230                 235                 240

Tyr Arg Thr Thr Arg Leu Ser Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Glu Lys Thr Gln
        275                 280                 285

Phe Glu Val Thr Tyr Thr Arg Asn Gln Asp Ile Leu Lys Asn Lys Pro
    290                 295                 300

Gly Ile His Tyr Ala Pro Pro Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Ile Asp Lys Tyr Ser Asp Asp Asn Lys Pro Tyr Lys Glu Gly
            340                 345                 350

<210> SEQ ID NO 14
<211> LENGTH: 351
<212> TYPE: PRT
<213> ORGANISM: Staphylococcus aureus

<400> SEQUENCE: 14

Met Lys Asn Lys Lys Arg Val Leu Ile Ala Ser Ser Leu Ser Cys Ala
 1               5                  10                  15

Ile Leu Leu Leu Ser Ala Ala Thr Thr Gln Ala Asn Ser Ala His Lys
                 20                  25                  30

Asp Ser Gln Asp Gln Asn Lys Lys Glu His Val Asp Lys Ser Gln Gln
             35                  40                  45

Lys Asp Lys Arg Asn Val Thr Asn Lys Asp Lys Asn Ser Thr Val Pro
 50                  55                  60
```

```
Asp Asp Ile Gly Lys Asn Gly Lys Ile Thr Lys Arg Thr Glu Thr Val
65                  70                  75                  80

Tyr Asp Glu Lys Thr Asn Ile Leu Gln Asn Leu Gln Phe Asp Phe Ile
                85                  90                  95

Asp Asp Pro Thr Tyr Asp Lys Asn Val Leu Leu Val Lys Lys Gln Gly
            100                 105                 110

Ser Ile His Ser Asn Leu Lys Phe Glu Ser His Lys Glu Glu Lys Asn
        115                 120                 125

Ser Asn Trp Leu Lys Tyr Pro Ser Glu Tyr His Val Asp Phe Gln Val
    130                 135                 140

Lys Arg Asn Arg Lys Thr Glu Ile Leu Asp Gln Leu Pro Lys Asn Lys
145                 150                 155                 160

Ile Ser Thr Ala Lys Val Asp Ser Thr Phe Ser Tyr Ser Ser Gly Gly
                165                 170                 175

Lys Phe Asp Ser Thr Lys Gly Ile Gly Arg Thr Ser Ser Asn Ser Tyr
            180                 185                 190

Ser Lys Thr Ile Ser Tyr Asn Gln Gln Asn Tyr Asp Thr Ile Ala Ser
        195                 200                 205

Gly Lys Asn Asn Asn Trp His Val His Trp Ser Val Ile Ala Asn Asp
    210                 215                 220

Leu Lys Tyr Gly Gly Glu Val Lys Asn Arg Asn Asp Glu Leu Leu Phe
225                 230                 235                 240

Tyr Arg Asn Thr Arg Ile Ala Thr Val Glu Asn Pro Glu Leu Ser Phe
                245                 250                 255

Ala Ser Lys Tyr Arg Tyr Pro Ala Leu Val Arg Ser Gly Phe Asn Pro
            260                 265                 270

Glu Phe Leu Thr Tyr Leu Ser Asn Glu Lys Ser Asn Gly Lys Thr Gln
        275                 280                 285

Phe Glu Val Thr Tyr Thr Arg Asn Gln Asp Ile Leu Lys Asn Arg Pro
    290                 295                 300

Gly Ile His Tyr Ala Pro Ser Ile Leu Glu Lys Asn Lys Asp Gly Gln
305                 310                 315                 320

Arg Leu Ile Val Thr Tyr Glu Val Asp Trp Lys Asn Lys Thr Val Lys
                325                 330                 335

Val Val Asp Lys Tyr Ser Asp Asp Asn Lys Pro Tyr Lys Glu Gly
            340                 345                 350

<210> SEQ ID NO 15
<211> LENGTH: 338
<212> TYPE: PRT
<213> ORGANISM: Staphylococcus aureus
<220> FEATURE:
<221> NAME/KEY: SIMILAR
<222> LOCATION: (1)..(338)
<223> OTHER INFORMATION: consensus majority LukB pro-peptide sequence

<400> SEQUENCE: 15

Met Ile Lys Gln Leu Cys Lys Asn Ile Thr Ile Cys Ser Leu Ala Leu
1               5                   10                  15

Ser Thr Ala Leu Thr Val Phe Pro Ala Thr Ser Tyr Ala Lys Ile Asn
                20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
        50                  55                  60
```

```
Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Arg Ile
                 85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Lys Gly
            260                 265                 270

Lys Ser Gln Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 16
<211> LENGTH: 339
<212> TYPE: PRT
<213> ORGANISM: Staphylococcus aureus

<400> SEQUENCE: 16

Met Ile Lys Gln Val Cys Lys Asn Ile Thr Ile Cys Ser Leu Ala Leu
 1               5                  10                  15

Ser Thr Ala Leu Thr Val Phe Pro Ala Ser Ser Tyr Ala Glu Ile Lys
                20                  25                  30

Ser Lys Ile Thr Thr Val Ser Glu Lys Asn Leu Asp Gly Asp Thr Lys
            35                  40                  45

Met Tyr Thr Arg Thr Ala Thr Thr Ser Asp Thr Glu Lys Lys Ile Ser
    50                  55                  60

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Lys Ile
                 85                  90                  95
```

Leu Asn Pro Asn Gly Tyr Trp Asn Ser Thr Leu Arg Trp Pro Gly Ser
             100                 105                 110

Tyr Ser Val Ser Ile Gln Asn Val Asp Asp Asn Asn Ser Thr Asn
         115                 120                 125

Val Thr Asp Phe Ala Pro Lys Asn Gln Asp Glu Ser Arg Glu Val Lys
130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                 165                 170                 175

Ser Tyr Gln Gln Pro Ser Tyr Arg Thr Leu Ile Asp Gln Pro Thr Thr
             180                 185                 190

Asn Lys Gly Val Ala Trp Lys Val Glu Ala His Ser Ile Asn Asn Met
         195                 200                 205

Gly His Asp His Thr Arg Gln Leu Thr Asn Asp Ser Asp Asp Arg Val
         210                 215                 220

Lys Ser Glu Ile Phe Ser Leu Thr Arg Asn Gly Asn Leu Trp Ala Lys
225                 230                 235                 240

Asp Asn Phe Thr Pro Lys Asn Lys Met Pro Val Thr Val Ser Glu Gly
                 245                 250                 255

Phe Asn Pro Glu Phe Leu Ala Val Met Ser His Asp Lys Asn Asp Lys
             260                 265                 270

Gly Lys Ser Arg Phe Ile Val His Tyr Lys Arg Ser Met Asp Asp Phe
         275                 280                 285

Lys Leu Asp Trp Asn Lys His Gly Phe Trp Gly Tyr Trp Ser Gly Glu
         290                 295                 300

Asn His Val Asp Gln Lys Glu Lys Leu Ser Ala Leu Tyr Glu Val
305                 310                 315                 320

Asp Trp Lys Thr His Asp Val Lys Leu Ile Lys Thr Phe Asn Asp Lys
                 325                 330                 335

Glu Lys Lys

<210> SEQ ID NO 17
<211> LENGTH: 290
<212> TYPE: PRT
<213> ORGANISM: Staphylococcus aureus

<400> SEQUENCE: 17

Met Tyr Thr Arg Thr Ala Thr Thr Ser Asp Ser Gln Lys Asn Ile Thr
1               5                   10                  15

Gln Ser Leu Gln Phe Asn Phe Leu Thr Glu Pro Asn Tyr Asp Lys Glu
             20                  25                  30

Thr Val Phe Ile Lys Ala Lys Gly Thr Ile Gly Ser Gly Leu Arg Ile
         35                  40                  45

Leu Asp Pro Asn Gly Tyr Trp Asn Ser Thr Leu Arg Trp Pro Gly Ser
50                  55                  60

Tyr Ser Val Ser Ile Gln Asn Val Asp Asp Asn Asn Thr Asn Val
65                  70                  75                  80

Thr Asp Phe Ala Pro Lys Asn Gln Asp Glu Ser Arg Glu Val Lys Tyr
                 85                  90                  95

Thr Tyr Gly Tyr Lys Thr Gly Gly Asp Phe Ser Ile Asn Arg Gly Gly
             100                 105                 110

Leu Thr Gly Asn Ile Thr Lys Glu Ser Asn Tyr Ser Glu Thr Ile Ser
         115                 120                 125

Tyr Gln Gln Pro Ser Tyr Arg Thr Leu Leu Asp Gln Ser Thr Ser His
            130                 135                 140

Lys Gly Val Gly Trp Lys Val Glu Ala His Leu Ile Asn Asn Met Gly
145                 150                 155                 160

His Asp His Thr Arg Gln Leu Thr Asn Asp Ser Asp Asn Arg Thr Lys
                165                 170                 175

Ser Glu Ile Phe Ser Leu Thr Arg Asn Gly Asn Leu Trp Ala Lys Asp
            180                 185                 190

Asn Phe Thr Pro Lys Asp Lys Met Pro Val Thr Val Ser Glu Gly Phe
        195                 200                 205

Asn Pro Glu Phe Leu Ala Val Met Ser His Asp Lys Lys Asp Lys Gly
210                 215                 220

Lys Ser Gln Phe Val Val His Tyr Lys Arg Ser Met Asp Glu Phe Lys
225                 230                 235                 240

Ile Asp Trp Asn Arg His Gly Phe Trp Gly Tyr Trp Ser Gly Glu Asn
                245                 250                 255

His Val Asp Lys Lys Glu Glu Lys Leu Ser Ala Leu Tyr Glu Val Asp
            260                 265                 270

Trp Lys Thr His Asn Val Lys Phe Val Lys Val Leu Asn Asp Asn Glu
        275                 280                 285

Lys Lys
    290

<210> SEQ ID NO 18
<211> LENGTH: 338
<212> TYPE: PRT
<213> ORGANISM: Staphylococcus aureus

<400> SEQUENCE: 18

Met Ile Lys Gln Val Cys Lys Asn Ile Thr Ile Cys Ser Leu Ala Leu
1               5                   10                  15

Ser Thr Ala Leu Thr Ile Phe Pro Ala Ser Ser Tyr Ala Lys Ile Asn
            20                  25                  30

Ser Glu Ile Lys Gln Val Ser Glu Lys Asn Leu Asp Gly Glu Thr Lys
        35                  40                  45

Met Tyr Thr Arg Thr Ala Thr Thr Ser Asp Ser Gln Lys Asn Ile Thr
50                  55                  60

Gln Ser Leu Gln Phe Asn Phe Leu Thr Glu Lys Asn Tyr Asp Lys Glu
65                  70                  75                  80

Thr Val Phe Ile Lys Ala Lys Gly Thr Ile Gly Ser Gly Leu Arg Ile
                85                  90                  95

Leu Glu Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Gln Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Ile Asp Gln Pro Thr Thr Asn
            180                 185                 190

Lys Gly Val Ala Trp Lys Val Glu Ala His Leu Ile Asn Asn Met Gly
        195                 200                 205

His Asp His Thr Arg Gln Leu Thr Asn Asp Ser Asp Arg Val Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
            275                 280                 285

Ile Asp Trp Asn Lys His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asn Val Lys Phe Ile Lys Val Leu Asn Asp Lys Glu
                325                 330                 335

Lys Lys

<210> SEQ ID NO 19
<211> LENGTH: 339
<212> TYPE: PRT
<213> ORGANISM: Staphylococcus aureus

<400> SEQUENCE: 19

Met Ile Lys Gln Val Cys Lys Asn Ile Thr Ile Cys Ser Leu Ala Leu
1               5                   10                  15

Ser Thr Ala Leu Thr Val Phe Pro Ala Ser Ser Tyr Ala Glu Ile Lys
            20                  25                  30

Ser Lys Ile Thr Thr Val Ser Glu Lys Asn Leu Asp Gly Asp Thr Lys
        35                  40                  45

Met Tyr Thr Arg Thr Ala Thr Thr Ser Asp Thr Glu Lys Lys Ile Ser
    50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Lys Ile
                85                  90                  95

Leu Asn Pro Asn Gly Tyr Trp Asn Ser Thr Leu Thr Trp Pro Gly Ser
            100                 105                 110

Tyr Ser Val Ser Ile Gln Asn Val Asp Asp Asn Asn Ser Thr Asn
        115                 120                 125

Val Thr Asp Phe Ala Pro Lys Asn Gln Asp Glu Ser Arg Glu Val Lys
    130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                165                 170                 175

Ser Tyr Gln Gln Pro Ser Tyr Arg Thr Leu Ile Asp Gln Pro Thr Thr
            180                 185                 190

Asn Lys Gly Val Ala Trp Lys Val Glu Ala His Ser Ile Asn Asn Met
        195                 200                 205

Gly His Asp His Thr Arg Gln Leu Thr Asn Asp Ser Asp Arg Val
    210                 215                 220

Lys Ser Glu Ile Phe Ser Leu Thr Arg Asn Gly Asn Leu Trp Ala Lys
225                 230                 235                 240

-continued

```
Asp Asn Phe Thr Pro Lys Asn Lys Met Pro Val Thr Val Ser Glu Gly
                245                 250                 255

Phe Asn Pro Glu Phe Leu Ala Val Met Ser His Asp Lys Asn Asp Lys
            260                 265                 270

Gly Lys Ser Arg Phe Ile Val His Tyr Lys Arg Ser Met Asp Asp Phe
        275                 280                 285

Lys Leu Asp Trp Asn Lys His Gly Phe Trp Gly Tyr Trp Ser Gly Glu
290                 295                 300

Asn His Val Asp Gln Lys Glu Glu Lys Leu Ser Ala Leu Tyr Glu Val
305                 310                 315                 320

Asp Trp Lys Thr His Asp Val Lys Leu Ile Lys Thr Ile Asn Asp Lys
                325                 330                 335

Glu Gln Lys

<210> SEQ ID NO 20
<211> LENGTH: 338
<212> TYPE: PRT
<213> ORGANISM: Staphylococcus aureus

<400> SEQUENCE: 20

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
                20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
        50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Lys Asp Lys Gly
            260                 265                 270
```

```
Lys Ser Gln Phe Val Val His Tyr Lys Arg Ser Met Asp Glu Phe Lys
            275                 280                 285

Ile Asp Trp Asn Arg His Gly Phe Trp Gly Tyr Trp Ser Gly Glu Asn
290                 295                 300

His Val Asp Glu Lys Glu Lys Leu Ser Ala Leu Tyr Glu Val Asp
305                 310                 315                 320

Trp Lys Thr His Asn Val Lys Phe Val Lys Val Leu Asn Asp Asn Glu
            325                 330                 335

Lys Lys

<210> SEQ ID NO 21
<211> LENGTH: 339
<212> TYPE: PRT
<213> ORGANISM: Staphylococcus aureus

<400> SEQUENCE: 21

Met Ile Lys Gln Val Cys Lys Asn Ile Thr Ile Cys Ser Leu Ala Leu
1               5                   10                  15

Ser Thr Ala Leu Thr Val Phe Pro Ala Ser Ser Tyr Ala Glu Ile Lys
            20                  25                  30

Ser Lys Ile Thr Thr Val Ser Glu Lys Asn Leu Asp Gly Asp Thr Lys
        35                  40                  45

Met Tyr Thr Arg Thr Ala Thr Thr Ser Asp Thr Glu Lys Lys Ile Ser
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Lys Ile
                85                  90                  95

Leu Asn Pro Asn Gly Tyr Trp Asn Ser Thr Leu Arg Trp Pro Gly Ser
            100                 105                 110

Tyr Ser Val Ser Ile Gln Asn Val Asp Asp Asn Asn Ser Thr Asn
        115                 120                 125

Val Thr Asp Phe Ala Pro Lys Asn Gln Asp Glu Ser Arg Glu Val Lys
130                 135                 140

Tyr Thr Tyr Gly Tyr Lys Thr Gly Gly Asp Phe Ser Ile Asn Arg Gly
145                 150                 155                 160

Gly Leu Thr Gly Asn Ile Thr Lys Glu Lys Asn Tyr Ser Glu Thr Ile
                165                 170                 175

Ser Tyr Gln Gln Pro Ser Tyr Arg Thr Leu Ile Asp Gln Pro Thr Thr
            180                 185                 190

Asn Lys Gly Val Ala Trp Lys Val Glu Ala His Ser Ile Asn Asn Met
        195                 200                 205

Gly His Asp His Thr Arg Gln Leu Thr Asn Asp Ser Asp Asp Arg Val
210                 215                 220

Lys Ser Glu Ile Phe Ser Leu Thr Arg Asn Gly Asn Leu Trp Ala Lys
225                 230                 235                 240

Asp Asn Phe Thr Pro Lys Asn Lys Met Pro Val Thr Val Ser Glu Gly
                245                 250                 255

Phe Asn Pro Glu Phe Leu Ala Val Met Ser His Asp Lys Asn Asp Lys
            260                 265                 270

Gly Lys Ser Arg Phe Ile Val His Tyr Lys Arg Ser Met Asp Asp Phe
        275                 280                 285

Lys Leu Asp Trp Asn Lys His Gly Phe Trp Gly Tyr Trp Ser Gly Glu
290                 295                 300
```

Asn His Val Asp Gln Lys Glu Glu Lys Leu Ser Ala Leu Tyr Glu Val
305                 310                 315                 320

Asp Trp Lys Thr His Asp Val Lys Leu Ile Lys Thr Ile Asn Asp Lys
            325                 330                 335

Glu Gln Lys

<210> SEQ ID NO 22
<211> LENGTH: 338
<212> TYPE: PRT
<213> ORGANISM: Staphylococcus aureus

<400> SEQUENCE: 22

Met Ile Lys Gln Leu Tyr Lys Asn Ile Thr Ile Cys Ser Leu Ala Ile
1               5                   10                  15

Ser Thr Ala Leu Thr Val Phe Pro Ala Thr Ser Tyr Ala Lys Ile Asn
            20                  25                  30

Ser Glu Ile Lys Ala Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Lys Asp Lys Gly
            260                 265                 270

Lys Ser Gln Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

```
Trp Lys Thr His Asp Val Lys Phe Val Lys Val Leu Asn Asp Asn Glu
            325                 330                 335
Lys Lys

<210> SEQ ID NO 23
<211> LENGTH: 338
<212> TYPE: PRT
<213> ORGANISM: Staphylococcus aureus

<400> SEQUENCE: 23

Met Ile Lys Gln Leu Tyr Lys Asn Ile Thr Ile Cys Thr Leu Ala Leu
1               5                   10                  15

Ser Thr Thr Phe Thr Val Leu Pro Ala Thr Ser Tyr Ala Lys Ile Asn
            20                  25                  30

Ser Glu Ile Lys Ala Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
    50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
    130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
    210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
    290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys
```

<210> SEQ ID NO 24
<211> LENGTH: 338
<212> TYPE: PRT
<213> ORGANISM: Staphylococcus aureus

<400> SEQUENCE: 24

| Met | Ile | Lys | Gln | Leu | Tyr | Lys | Asn | Ile | Thr | Ile | Cys | Ser | Leu | Thr | Ile |
|---|---|---|---|---|---|---|---|---|---|---|---|---|---|---|---|
| 1 | | | | 5 | | | | | 10 | | | | | 15 | |

Ser Thr Ala Leu Thr Val Phe Pro Ala Thr Ser Tyr Ala Lys Ile Asn
            20                  25                  30

Ser Glu Ile Lys Ala Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
 50                  55                  60

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
            115                 120                 125

Thr Asp Phe Ala Pro Lys Asn Gln Asp Glu Ser Arg Glu Val Lys Tyr
130                 135                 140

Thr Tyr Gly Tyr Lys Thr Gly Gly Asp Phe Ser Ile Asn Arg Gly Gly
145                 150                 155                 160

Leu Pro Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr His
            180                 185                 190

Lys Gly Val Gly Trp Lys Val Glu Ala His Leu Ile Asn Asn Met Gly
            195                 200                 205

His Asp His Thr Arg Gln Leu Thr Asn Asp Ser Asp Asn Arg Thr Lys
210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Asp Glu Gly
            260                 265                 270

Lys Ser Lys Phe Val Val His Tyr Lys Arg Ser Met Asp Glu Phe Lys
            275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

Trp Lys Thr His Asp Val Lys Phe Val Lys Val Leu Asn Asp Asn Glu
                325                 330                 335

Lys Lys

<210> SEQ ID NO 25
<211> LENGTH: 338
<212> TYPE: PRT
<213> ORGANISM: Staphylococcus aureus

<400> SEQUENCE: 25

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
            20                  25                  30

Ser Glu Ile Lys Gln Val Ser Glu Lys Asn Leu Asp Gly Asp Thr Lys
        35                  40                  45

Met Tyr Thr Arg Thr Ala Thr Thr Ser Asp Ser Gln Lys Asn Ile Thr
50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
        115                 120                 125

Thr Asp Phe Ala Pro Lys Asn Gln Asp Glu Ser Arg Glu Val Lys Tyr
130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
        195                 200                 205

His Asp His Thr Arg Gln Leu Thr Asn Asp Ser Asp Asn Arg Thr Lys
210                 215                 220

Ser Glu Ile Phe Ser Leu Thr Arg Asn Gly Asn Leu Trp Ala Lys Asp
225                 230                 235                 240

Asn Phe Thr Pro Lys Asn Lys Met Pro Val Thr Val Ser Glu Gly Phe
                245                 250                 255

Asn Pro Glu Phe Leu Ala Val Met Ser His Asp Lys Lys Asp Glu Gly
            260                 265                 270

Lys Ser Lys Phe Val Val His Tyr Lys Arg Ser Met Asp Glu Phe Lys
        275                 280                 285

Ile Asp Trp Asn Arg His Gly Phe Trp Gly Tyr Trp Ser Gly Glu Asn
290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 26
<211> LENGTH: 338
<212> TYPE: PRT
<213> ORGANISM: Staphylococcus aureus

<400> SEQUENCE: 26

Met Ile Lys Gln Leu Cys Lys Asn Ile Thr Ile Cys Thr Leu Ala Leu
1               5                   10                  15

Ser Thr Thr Phe Thr Val Leu Pro Ala Thr Ser Phe Ala Lys Ile Asn
            20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
 50                  55                  60

Gln Ser Leu Gln Phe Asn Phe Leu Thr Glu Pro Asn Tyr Asp Lys Glu
 65                  70                  75                  80

Thr Val Phe Ile Lys Ala Lys Gly Thr Ile Gly Ser Gly Leu Arg Ile
            85                  90                  95

Leu Asp Pro Asn Gly Tyr Trp Asn Ser Thr Leu Arg Trp Pro Gly Ser
            100                 105                 110

Tyr Ser Val Ser Ile Gln Asn Val Asp Asp Asn Asn Thr Asn Val
            115                 120                 125

Thr Asp Phe Ala Pro Lys Asn Gln Asp Glu Ser Arg Glu Val Lys Tyr
            130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
            165                 170                 175

Tyr Gln Gln Pro Ser Tyr Arg Thr Leu Leu Asp Gln Ser Thr Ser His
            180                 185                 190

Lys Gly Val Gly Trp Lys Val Glu Ala His Leu Ile Asn Asn Met Gly
            195                 200                 205

His Asp His Thr Arg Gln Leu Thr Asn Asp Ser Asp Asn Arg Thr Lys
            210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
            245                 250                 255

Asn Pro Glu Phe Leu Ala Val Met Ser His Asp Lys Lys Asp Lys Gly
            260                 265                 270

Lys Ser Gln Phe Val Val His Tyr Lys Arg Ser Met Asp Glu Phe Lys
            275                 280                 285

Ile Asp Trp Asn Arg His Gly Phe Trp Gly Tyr Trp Ser Gly Glu Asn
            290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
            325                 330                 335

Lys Lys

<210> SEQ ID NO 27
<211> LENGTH: 338
<212> TYPE: PRT
<213> ORGANISM: Staphylococcus aureus

<400> SEQUENCE: 27

Met Ile Lys Gln Leu Cys Lys Asn Ile Thr Ile Cys Thr Leu Ala Leu
 1                   5                  10                  15

Ser Thr Thr Phe Thr Val Leu Pro Ala Thr Ser Phe Ala Lys Ile Asn
            20                  25                  30

Ser Glu Ile Lys Gln Val Ser Glu Lys Asn Leu Asp Gly Asp Thr Lys
            35                  40                  45

Met Tyr Thr Arg Thr Ala Thr Thr Ser Asp Ser Gln Lys Asn Ile Thr
    50                  55                  60

Gln Ser Leu Gln Phe Asn Phe Leu Thr Glu Pro Asn Tyr Asp Lys Glu
65                  70                  75                  80

Thr Val Phe Ile Lys Ala Lys Gly Thr Ile Gly Ser Gly Leu Arg Ile
                85                  90                  95

Leu Asp Pro Asn Gly Tyr Trp Asn Ser Thr Leu Arg Trp Pro Gly Ser
                100                 105                 110

Tyr Ser Val Ser Ile Gln Asn Val Asp Asn Asn Thr Asn Val
                115                 120                 125

Thr Asp Phe Ala Pro Lys Asn Gln Asp Glu Ser Arg Glu Val Lys Tyr
                130                 135                 140

Thr Tyr Gly Tyr Lys Thr Gly Gly Asp Phe Ser Ile Asn Arg Gly Gly
145                 150                 155                 160

Leu Thr Gly Asn Ile Thr Lys Glu Ser Asn Tyr Ser Glu Thr Ile Ser
                165                 170                 175

Tyr Gln Gln Pro Ser Tyr Arg Thr Leu Leu Asp Gln Ser Thr Ser His
                180                 185                 190

Lys Gly Val Gly Trp Lys Val Glu Ala His Leu Ile Asn Asn Met Gly
                195                 200                 205

His Asp His Thr Arg Gln Leu Thr Asn Asp Ser Asp Asn Arg Thr Lys
210                 215                 220

Ser Glu Ile Phe Ser Leu Thr Arg Asn Gly Asn Leu Trp Ala Lys Asp
225                 230                 235                 240

Asn Phe Thr Pro Lys Asp Lys Met Pro Val Thr Val Ser Glu Gly Phe
                245                 250                 255

Asn Pro Glu Phe Leu Ala Val Met Ser His Asp Lys Lys Asp Lys Gly
                260                 265                 270

Lys Ser Gln Phe Val Val His Tyr Lys Arg Ser Met Asp Glu Phe Lys
                275                 280                 285

Ile Asp Trp Asn Arg His Gly Phe Trp Gly Tyr Trp Ser Gly Glu Asn
                290                 295                 300

His Val Asp Lys Lys Glu Glu Lys Leu Ser Ala Leu Tyr Glu Val Asp
305                 310                 315                 320

Trp Lys Thr His Asn Val Lys Phe Val Lys Val Leu Asn Asp Asn Glu
                325                 330                 335

Lys Lys

<210> SEQ ID NO 28
<211> LENGTH: 324
<212> TYPE: PRT
<213> ORGANISM: Staphylococcus aureus
<220> FEATURE:
<221> NAME/KEY: SIMILAR
<222> LOCATION: (1)..(324)
<223> OTHER INFORMATION: mature LukA sequence of the consensus majority
      LukA pro-peptide sequence of SEQ ID NO: 1

<400> SEQUENCE: 28

Asn Ser Ala His Lys Asp Ser Gln Asp Gln Asn Lys Lys Glu His Val
1               5                   10                  15

Asp Lys Ser Gln Gln Lys Glu Lys Arg Asn Val Thr Asn Lys Asp Lys
                20                  25                  30

Asn Ser Thr Xaa Pro Asp Asp Ile Gly Lys Asn Gly Lys Ile Thr Lys
                35                  40                  45

Arg Thr Glu Thr Val Tyr Asp Glu Lys Thr Asn Ile Leu Gln Asn Leu
 50                  55                  60

Gln Phe Asp Phe Ile Asp Asp Pro Thr Tyr Asp Lys Asn Val Leu Leu
 65                  70                  75                  80

Val Lys Lys Gln Gly Ser Ile His Ser Asn Leu Lys Phe Glu Ser His
                 85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
                115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
            195                 200                 205

Asp Glu Leu Leu Phe Tyr Arg Asn Thr Arg Ile Ala Thr Val Glu Asn
210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
            275                 280                 285

Asn Lys Asp Gly Gln Arg Leu Ile Val Thr Tyr Glu Val Asp Trp Lys
290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 29
<211> LENGTH: 309
<212> TYPE: PRT
<213> ORGANISM: Staphylococcus aureus
<220> FEATURE:
<221> NAME/KEY: SIMILAR
<222> LOCATION: (1)..(309)
<223> OTHER INFORMATION: mature LukB sequence of the consensus majority
      LukB pro-peptide sequence of SEQ ID NO: 15

<400> SEQUENCE: 29

Lys Ile Asn Ser Glu Ile Lys Gln Val Ser Glu Lys Asn Leu Asp Gly
 1                   5                  10                  15

Asp Thr Lys Met Tyr Thr Arg Thr Ala Thr Thr Ser Asp Ser Gln Lys
                 20                  25                  30

Asn Ile Thr Gln Ser Leu Gln Phe Asn Phe Leu Thr Glu Pro Asn Tyr
             35                  40                  45

Asp Lys Glu Thr Val Phe Ile Lys Ala Lys Gly Thr Ile Gly Ser Gly
 50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 30
<211> LENGTH: 1056
<212> TYPE: DNA
<213> ORGANISM: Staphylococcus aureus
<220> FEATURE:
<221> NAME/KEY: misc_feature
<222> LOCATION: (1)..(1056)
<223> OTHER INFORMATION: encodes the LukA polypeptide of S. aureus
      (Newman) of SEQ ID NO: 2

<400> SEQUENCE: 30
atgaaaaata aaaacgtgt tttaatagcg tcatcattat catgtgcaat tttattgtta      60
tcagcagcaa cgactcaagc aaattcagct cataaagact ctcaagacca aaataagaaa    120
gaacatgttg ataagtctca acaaaaagac aaacgtaatg ttactaataa agataaaaat    180
tcaacagcac cggatgatat tgggaaaaac ggtaaaatca caaacgaac tgaaacagta    240 tatgatgaga aaacaaatat actccaaaat ttacaattcg actttatcga tgatccaact    300
tatgacaaga atgtattact tgttaaaaaa caaggctcaa ttcattcaaa tttaaagttt    360
gaatctcata agaagaaaa aaattcaaat tggttaaagt atccaagtga gtaccatgta    420
gattttcaag taaaagaaa tcgtaaaact gaaattattag accaattgcc gaaaaataaa    480
atttcaactg caaaagtaga cagtacattt tcatatagct caggtggtaa attcgattca    540

```
acaaaaggta ttggacgaac ttcatcaaat agctactcca aaacgattag ttataatcag    600
caaaattatg acacaattgc cagcggtaaa aataataact ggcatgtaca ctggtcagtt    660
attgcgaatg acttgaagta tggtggagaa gtgaaaaata gaaatgatga attattattc    720
tatagaaata cgagaattgc tactgtagaa aaccctgaac taagctttgc ttcaaaatat    780
agatacccag cattagtaag aagtggcttt aatccagaat ttttaactta tttatctaat    840
gaaaagtcaa atgagaaaac gcaatttgaa gtaacataca cacgaaatca agatattttg    900
aaaaacagac ctggaataca ttatgcacct ccaattttag aaaaaaataa agatggtcaa    960
agattaattg tcacttatga agttgattgg aaaaataaaa cagttaaagt cgttgataaa   1020
tattctgatg acaataaacc ttataaagaa ggataa                             1056

<210> SEQ ID NO 31
<211> LENGTH: 1017
<212> TYPE: DNA
<213> ORGANISM: Staphylococcus aureus
<220> FEATURE:
<221> NAME/KEY: misc_feature
<222> LOCATION: (1)..(1017)
<223> OTHER INFORMATION: encodes the LukB polypeptide of S. aureus
      (Newman) of SEQ ID NO: 27

<400> SEQUENCE: 31
atgattaaac aactatgtaa aaatatcaca atttgtacgt tagcactatc gactactttc     60
actgtattac cagctacttc atttgcaaag attaattctg aaatcaaaca agtttctgag    120
aagaatcttg atggtgatac taaaatgtat acacgtacag ctacaacaag tgatagtcaa    180
aaaaatatta ctcaaagctt acaatttaat ttcttaactg aacctaatta tgataaagaa    240 acagtatttta ttaaagcaaa aggtacaatt ggtagtggtt tgagaatttt agacccaaat    300
ggttattgga atagtacatt aagatggcct ggatcttatt cagtttcaat tcaaaatgtt    360
gatgacaaca acaatacaaa tgtgactgac tttgcaccaa aaaatcagga tgaatcaaga    420
gaagttaaat atacgtatgg ttataaaaca ggtggagatt tttcgattaa tcgtggaggc    480
ttaactggaa atattacaaa agagagtaat tattcagaga cgattagtta tcaacaacca    540
tcatatcgta cattacttga tcaatctacg tcacataaag gtgtaggttg aaagtagaa    600 gcacatttga taaataatat gggacatgac catacgagac aattaactaa tgatagtgat    660
aatagaacta aaagtgaaat ttttttcttta acacgaaatg gaaatttatg ggcgaaagat    720
aatttcacac ctaaagacaa aatgcctgta actgtgtctg aagggtttaa tccagaattt    780
ttagctgtta tgtcacatga taaaaaagac aaaggtaaat cacaatttgt tgttcattat    840
aaaagatcaa tggatgagtt taaaatagat tggaatcgcc atggtttctg gggctattgg    900
tctggtgaaa accatgtaga taaaaaagaa gaaaaattat cagcattata tgaagttgat    960
tggaagacac ataatgtgaa gtttgtaaaa gtacttaatg ataatgaaaa gaaataa      1017

<210> SEQ ID NO 32
<211> LENGTH: 324
<212> TYPE: PRT
<213> ORGANISM: Staphylococcus aureus

<400> SEQUENCE: 32

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30
```

-continued

Asn Ser Thr Ala Pro Asp Asp Ile Gly Lys Asn Gly Lys Ile Thr Lys
                35                  40                  45

Arg Thr Glu Thr Val Tyr Asp Glu Lys Thr Asn Ile Leu Gln Asn Leu
 50                  55                  60

Gln Phe Asp Phe Ile Asp Asp Pro Thr Tyr Asp Lys Asn Val Leu Leu
 65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
                100                 105                 110

Val Asp Phe Gln Val Lys Arg Asn Arg Lys Thr Glu Ile Leu Asp Gln
                115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
                180                 185                 190

Val Ile Ala Asn Asp Leu Lys Tyr Gly Gly Glu Val Lys Asn Arg Asn
                195                 200                 205

Asp Glu Leu Leu Phe Tyr Arg Asn Thr Arg Ile Ala Thr Val Glu Asn
                210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
                260                 265                 270

Leu Lys Asn Arg Pro Gly Ile His Tyr Ala Pro Pro Ile Leu Glu Lys
                275                 280                 285

Asn Lys Asp Gly Gln Arg Leu Ile Val Thr Tyr Glu Val Asp Trp Lys
                290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 33
<211> LENGTH: 324
<212> TYPE: PRT
<213> ORGANISM: Staphylococcus aureus

<400> SEQUENCE: 33

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
                20                  25                  30

Asn Thr Pro Gly Pro Asp Asp Ile Gly Lys Asn Gly Lys Val Thr Lys
                35                  40                  45

Arg Thr Val Ser Glu Tyr Asp Lys Glu Thr Asn Ile Leu Gln Asn Leu
 50                  55                  60

Gln Phe Asp Phe Ile Asp Asp Pro Thr Tyr Asp Lys Asn Val Leu Leu
 65                  70                  75                  80

Val Lys Lys Gln Gly Ser Ile His Ser Asn Leu Lys Phe Glu Ser His
            85                  90                  95

Arg Asn Glu Thr Asn Ala Ser Trp Leu Lys Tyr Pro Ser Glu Tyr His
                100                 105                 110

Val Asp Phe Gln Val Gln Arg Asn Pro Lys Thr Glu Ile Leu Asp Gln
            115                 120                 125

Leu Pro Lys Asn Lys Ile Ser Thr Ala Lys Val Asp Ser Thr Phe Ser
130                 135                 140

Tyr Ser Leu Gly Gly Lys Phe Asp Ser Thr Lys Gly Ile Gly Arg Thr
145                 150                 155                 160

Ser Ser Asn Ser Tyr Ser Lys Ser Ile Ser Tyr Asn Gln Gln Asn Tyr
                165                 170                 175

Asp Thr Ile Ala Ser Gly Lys Asn Asn Arg His Val His Trp Ser
            180                 185                 190

Val Val Ala Asn Asp Leu Lys Tyr Gly Asn Glu Ile Lys Asn Arg Asn
            195                 200                 205

Asp Glu Phe Leu Phe Tyr Arg Asn Thr Arg Leu Ser Thr Val Glu Asn
210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Ile Ser Asn Glu Lys Ser
                245                 250                 255

Asn Glu Lys Thr Arg Phe Glu Val Thr Tyr Thr Arg Asn Gln Asp Ile
            260                 265                 270

Leu Lys Asn Lys Pro Gly Ile His Tyr Gly Gln Pro Ile Leu Glu Gln
            275                 280                 285

Asn Lys Asp Gly Gln Arg Phe Ile Val Val Tyr Glu Val Asp Trp Lys
290                 295                 300

Asn Lys Thr Val Lys Val Val Glu Lys Tyr Ser Asp Gln Asn Lys Pro
305                 310                 315                 320

Tyr Lys Glu Gly

<210> SEQ ID NO 34
<211> LENGTH: 323
<212> TYPE: PRT
<213> ORGANISM: Staphylococcus aureus

<400> SEQUENCE: 34

Asn Ser Ala His Lys Asp Ser Gln Asp Gln Asn Lys Lys Glu His Val
1               5                   10                  15

Asp Lys Ser Gln Gln Lys Glu Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
            85                  90                  95

Lys Glu Glu Lys Asn Ser Asn Trp Leu Lys Tyr Pro Ser Glu Tyr His
                100                 105                 110

Val Asp Phe Gln Val Lys Arg Asn Arg Lys Thr Glu Ile Leu Asp Gln
            115                 120                 125

Leu Pro Lys Asn Lys Ile Ser Thr Ala Lys Val Asp Ser Thr Phe Ser
            130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Ile Leu Glu Lys
        275                 280                 285

Asn Lys Glu Gly Gln Arg Leu Ile Val Thr Tyr Glu Val Asp Trp Lys
    290                 295                 300

Asn Lys Thr Val Lys Val Val Asp Lys Tyr Ser Asp Asn Lys Ser Phe
305                 310                 315                 320

Arg Glu Gly

<210> SEQ ID NO 35
<211> LENGTH: 323
<212> TYPE: PRT
<213> ORGANISM: Staphylococcus aureus

<400> SEQUENCE: 35

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
            85                  90                  95

Lys Glu Glu Lys Asn Ser Asn Trp Leu Lys Tyr Pro Ser Glu Tyr His
        100                 105                 110

Val Asp Phe Gln Val Lys Arg Asn Pro Lys Thr Glu Ile Leu Asp Gln
    115                 120                 125

Leu Pro Lys Asn Lys Ile Ser Thr Ala Lys Val Asp Ser Thr Phe Ser
            130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

```
Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
            195                 200                 205

Asp Glu Leu Leu Phe Tyr Arg Asn Thr Arg Ile Ala Thr Val Glu Asn
            210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
            245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Ile Leu Glu Lys
            275                 280                 285

Asn Lys Glu Gly Gln Arg Leu Ile Val Thr Tyr Glu Val Asp Trp Lys
            290                 295                 300

Asn Lys Thr Val Lys Val Val Asp Lys Tyr Thr Asp Asn Lys Ser Phe
305                 310                 315                 320

Arg Glu Gly

<210> SEQ ID NO 36
<211> LENGTH: 323
<212> TYPE: PRT
<213> ORGANISM: Staphylococcus aureus

<400> SEQUENCE: 36

Asn Ser Ala His Lys Asp Ser Gln Asp Gln Asn Lys Lys Glu His Val
1               5                   10                  15

Asp Lys Ser Gln Gln Lys Glu Lys Arg Asn Val Thr Asn Lys Asp Lys
            20                  25                  30

Asn Ser Thr Val Pro Asp Asp Ile Gly Lys Asn Gly Lys Ile Thr Lys
            35                  40                  45

Arg Thr Glu Thr Val Tyr Asp Glu Lys Thr Asn Ile Leu Gln Asn Leu
50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
            85                  90                  95

Lys Glu Glu Lys Asn Ser Asn Trp Leu Lys Tyr Pro Ser Glu Tyr His
            100                 105                 110

Val Asp Phe Gln Val Lys Arg Asn Pro Lys Thr Glu Ile Leu Asp Gln
            115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
            165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
            195                 200                 205

Asp Glu Leu Leu Phe Tyr Arg Asn Thr Arg Ile Ala Thr Val Glu Asn
            210                 215                 220
```

-continued

```
Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
            245                 250                 255

Asn Glu Lys Thr Gln Phe Glu Val Thr Tyr Thr Arg Asn Gln Asp Ile
        260                 265                 270

Leu Lys Asn Arg Pro Gly Ile His Tyr Ala Pro Ile Leu Glu Lys
    275                 280                 285

Asn Lys Glu Gly Gln Arg Leu Ile Val Thr Tyr Glu Val Asp Trp Lys
290                 295                 300

Asn Lys Thr Val Lys Val Val Asp Lys Tyr Ser Asp Asn Lys Ser Phe
305                 310                 315                 320

Arg Glu Gly
```

<210> SEQ ID NO 37
<211> LENGTH: 324
<212> TYPE: PRT
<213> ORGANISM: Staphylococcus aureus

<400> SEQUENCE: 37

```
Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Asn Tyr
            165                 170                 175

Asp Thr Ile Ala Ser Gly Lys Asn Asn Asn Trp His Val His Trp Ser
        180                 185                 190

Val Ile Ala Asn Asp Leu Lys Tyr Gly Gly Glu Val Lys Asn Arg Asn
195                 200                 205

Asp Glu Leu Leu Phe Tyr Arg Asn Thr Arg Ile Ala Thr Val Glu Asn
        210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
            245                 250                 255

Asn Glu Lys Thr Gln Phe Glu Val Thr Tyr Thr Arg Asn Gln Asp Ile
        260                 265                 270
```

```
Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 38
<211> LENGTH: 324
<212> TYPE: PRT
<213> ORGANISM: Staphylococcus aureus

<400> SEQUENCE: 38

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Lys Tyr
                165                 170                 175

Asp Thr Ile Ala Ile Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300
```

```
Asn Lys Thr Val Lys Val Asp Lys Tyr Ser Asp Asp Asn Lys Pro
305                 310                 315                 320

Tyr Lys Glu Gly

<210> SEQ ID NO 39
<211> LENGTH: 324
<212> TYPE: PRT
<213> ORGANISM: Staphylococcus aureus

<400> SEQUENCE: 39

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 40
<211> LENGTH: 324
```

```
<212> TYPE: PRT
<213> ORGANISM: Staphylococcus aureus

<400> SEQUENCE: 40

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
            20                  25                  30

Asn Thr Pro Gly Pro Asp Asp Ile Gly Lys Asn Gly Lys Val Thr Lys
        35                  40                  45

Arg Thr Val Ser Glu Tyr Asp Lys Glu Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Arg Asn Glu Thr Asn Ala Ser Trp Leu Lys Tyr Pro Ser Glu Tyr His
            100                 105                 110

Val Asp Phe Gln Val Gln Arg Asn Pro Lys Thr Glu Ile Leu Asp Gln
        115                 120                 125

Leu Pro Lys Asn Lys Ile Ser Thr Ala Lys Val Asp Ser Thr Phe Ser
130                 135                 140

Tyr Ser Leu Gly Gly Lys Phe Asp Ser Thr Lys Gly Ile Gly Arg Thr
145                 150                 155                 160

Ser Ser Asn Ser Tyr Ser Lys Ser Ile Ser Tyr Asn Gln Gln Asn Tyr
                165                 170                 175

Asp Thr Ile Ala Ser Gly Lys Asn Asn Asn Arg His Val His Trp Ser
            180                 185                 190

Val Val Ala Asn Asp Leu Lys Tyr Gly Asn Glu Ile Lys Asn Arg Asn
        195                 200                 205

Asp Glu Phe Leu Phe Tyr Arg Asn Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Ile Ser Asn Glu Lys Thr
                245                 250                 255

Asn Asp Lys Thr Arg Phe Glu Val Thr Tyr Thr Arg Asn Gln Asp Ile
            260                 265                 270

Leu Lys Asn Lys Pro Gly Ile His Tyr Gly Gln Pro Ile Leu Glu Gln
        275                 280                 285

Asn Lys Asp Gly Gln Arg Phe Ile Val Val Tyr Glu Val Asp Trp Lys
    290                 295                 300

Asn Lys Thr Val Lys Val Val Glu Lys Tyr Ser Asp Gln Asn Lys Pro
305                 310                 315                 320

Tyr Lys Glu Gly

<210> SEQ ID NO 41
<211> LENGTH: 324
<212> TYPE: PRT
<213> ORGANISM: Staphylococcus aureus

<400> SEQUENCE: 41

Asn Ser Ala Asn Lys Asp Ser Gln Asp Gln Thr Lys Lys Glu His Val
1               5                   10                  15
```

Asp Lys Ala Gln Gln Lys Glu Lys Arg Asn Val Asn Asp Lys Asp Lys
        20                  25                  30

Asn Thr Pro Gly Pro Asp Asp Ile Gly Lys Asn Gly Lys Val Thr Lys
            35                  40                  45

Arg Thr Glu Thr Val Tyr Asp Glu Lys Thr Asn Ile Leu Gln Asn Leu
 50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Asn Asn Ser Ser Trp Leu Lys Tyr Pro Ser Glu Tyr His
            100                 105                 110

Val Asp Phe Gln Val Lys Ser Asn Arg Lys Thr Glu Ile Leu Asp Gln
        115                 120                 125

Leu Pro Lys Asn Lys Ile Ser Thr Ala Lys Val Asp Ser Thr Phe Ser
130                 135                 140

Tyr Asn Ser Gly Gly Lys Phe Asp Ser Val Lys Gly Val Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Val Ala Asn Asp Leu Lys Tyr Gly Gly Glu Val Lys Asn Arg Asn
        195                 200                 205

Asp Asp Phe Leu Phe Tyr Arg Asn Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Val
            260                 265                 270

Leu Lys Asn Lys Pro Gly Ile His Tyr Ala Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Ile Asp Lys Tyr Ser Asp Glu Asn Lys Pro
305                 310                 315                 320

Tyr Lys Glu Gly

<210> SEQ ID NO 42
<211> LENGTH: 324
<212> TYPE: PRT
<213> ORGANISM: Staphylococcus aureus

<400> SEQUENCE: 42

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
            20                  25                  30

Asn Thr Pro Gly Pro Asp Asp Ile Gly Lys Asn Gly Lys Val Thr Lys
        35                  40                  45

Arg Thr Val Ser Glu Tyr Asp Lys Glu Thr Asn Ile Leu Gln Asn Leu
50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Arg Asn Glu Thr Asn Ala Ser Trp Leu Lys Tyr Pro Ser Glu Tyr His
            100                 105                 110

Val Asp Phe Gln Val Gln Arg Asn Pro Lys Thr Glu Ile Leu Asp Gln
            115                 120                 125

Leu Pro Lys Asn Lys Ile Ser Thr Ala Lys Val Asp Ser Thr Phe Ser
130                 135                 140

Tyr Ser Leu Gly Gly Lys Phe Asp Ser Thr Lys Gly Ile Gly Arg Thr
145                 150                 155                 160

Ser Ser Asn Ser Tyr Ser Lys Ser Ile Ser Tyr Asn Gln Gln Asn Tyr
                165                 170                 175

Asp Thr Ile Ala Ser Gly Lys Asn Asn Asn Arg His Val His Trp Ser
            180                 185                 190

Val Val Ala Asn Asp Leu Lys Tyr Gly Asn Glu Ile Lys Asn Arg Asn
            195                 200                 205

Asp Glu Phe Leu Phe Tyr Arg Asn Thr Arg Leu Ser Thr Val Glu Asn
210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Ile Ser Asn Glu Lys Ser
                245                 250                 255

Asn Glu Lys Thr Arg Phe Glu Val Thr Tyr Thr Arg Asn Gln Asp Ile
            260                 265                 270

Leu Lys Asn Lys Pro Gly Ile His Tyr Gly Gln Pro Ile Leu Glu Gln
            275                 280                 285

Asn Lys Asp Gly Gln Arg Phe Ile Val Val Tyr Glu Val Asp Trp Lys
290                 295                 300

Asn Lys Thr Val Lys Val Val Glu Lys Tyr Ser Asp Gln Asn Lys Pro
305                 310                 315                 320

Tyr Lys Glu Gly

<210> SEQ ID NO 43
<211> LENGTH: 324
<212> TYPE: PRT
<213> ORGANISM: Staphylococcus aureus

<400> SEQUENCE: 43

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
                20                  25                  30

Asn Thr Pro Gly Pro Asp Asp Ile Gly Lys Asn Gly Lys Val Thr Lys
            35                  40                  45

Arg Thr Glu Thr Val Tyr Asp Glu Lys Thr Asn Ile Leu Gln Asn Leu
50                  55                  60

Gln Phe Asp Phe Ile Asp Asp Pro Thr Tyr Asp Lys Asn Ile Leu Leu
65                  70                  75                  80

Val Lys Lys Gln Gly Ser Ile His Ser Asn Leu Lys Phe Glu Ser His
                85                  90                  95

Lys Glu Glu Asn Asn Ser Ser Trp Leu Lys Tyr Pro Ser Glu Tyr His
            100                 105                 110

Val Asp Phe Gln Val Lys Arg Asn Arg Lys Thr Glu Ile Leu Asp Gln
            115                 120                 125

Leu Pro Lys Asn Lys Ile Ser Thr Ala Lys Val Asp Ser Thr Phe Ser
    130                 135                 140

Tyr Asn Ser Gly Gly Lys Phe Asp Ser Val Lys Gly Val Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Val Ala Asn Asp Leu Lys Tyr Gly Gly Glu Val Lys Asn Arg Asn
        195                 200                 205

Asp Glu Phe Leu Phe Tyr Arg Thr Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Lys Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Ile Asp Lys Tyr Ser Asp Asp Asn Lys Pro
305                 310                 315                 320

Tyr Lys Glu Gly

<210> SEQ ID NO 44
<211> LENGTH: 324
<212> TYPE: PRT
<213> ORGANISM: Staphylococcus aureus

<400> SEQUENCE: 44

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

```
Ser Ser Asn Ser Tyr Ser Lys Thr Ile Ser Tyr Asn Gln Gln Asn Tyr
                165                 170                 175

Asp Thr Ile Ala Ser Gly Lys Asn Asn Trp His Val His Trp Ser
            180                 185                 190

Val Ile Ala Asn Asp Leu Lys Tyr Gly Gly Glu Val Lys Asn Arg Asn
            195                 200                 205

Asp Glu Leu Leu Phe Tyr Arg Asn Thr Arg Ile Ala Thr Val Glu Asn
            210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Ser Ile Leu Glu Lys
            275                 280                 285

Asn Lys Asp Gly Gln Arg Leu Ile Val Thr Tyr Glu Val Asp Trp Lys
            290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 45
<211> LENGTH: 310
<212> TYPE: PRT
<213> ORGANISM: Staphylococcus aureus

<400> SEQUENCE: 45

Glu Ile Lys Ser Lys Ile Thr Thr Val Ser Gly Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Glu Pro Asn Tyr
            35                  40                  45

Asp Lys Glu Thr Val Phe Ile Lys Ala Lys Gly Thr Ile Gly Ser Gly
        50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Ser Thr Asn Val Thr Asp Phe Ala Pro Lys Asn Gln Asp Glu Ser Arg
            100                 105                 110

Glu Val Lys Tyr Thr Tyr Gly Tyr Lys Thr Gly Gly Asp Phe Ser Ile
            115                 120                 125

Asn Arg Gly Gly Leu Thr Gly Asn Ile Thr Lys Glu Lys Asn Tyr Ser
            130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
            165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
            195                 200                 205
```

```
Trp Ala Lys Asp Asn Phe Thr Pro Lys Asn Lys Met Pro Val Thr Val
            210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Lys Leu Ser Ala Leu
            275                 280                 285

Tyr Glu Val Asp Trp Lys Thr His Asp Val Lys Leu Ile Lys Thr Phe
            290                 295                 300

Asn Asp Lys Glu Lys Lys
305                 310

<210> SEQ ID NO 46
<211> LENGTH: 309
<212> TYPE: PRT
<213> ORGANISM: Staphylococcus aureus

<400> SEQUENCE: 46

Lys Ile Asn Ser Glu Ile Lys Gln Val Ser Glu Lys Asn Leu Asp Gly
1               5                   10                  15

Glu Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Lys Asn Tyr
        35                  40                  45

Asp Lys Glu Thr Val Phe Ile Lys Ala Lys Gly Thr Ile Gly Ser Gly
    50                  55                  60

Leu Arg Ile Leu Glu Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Gln Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Ile Asp Gln Pro
145                 150                 155                 160

Thr Thr Asn Lys Gly Val Ala Trp Lys Val Glu Ala His Leu Ile Asn
                165                 170                 175

Asn Met Gly His Asp His Thr Arg Gln Leu Thr Asn Asp Ser Asp Asp
            180                 185                 190

Arg Val Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255
```

Glu Phe Lys Ile Asp Trp Asn Lys His Gly Phe Trp Gly Tyr Trp Ser
            260                 265                 270

Gly Glu Asn His Val Asp Lys Lys Glu Lys Leu Ser Ala Leu Tyr
        275                 280                 285

Glu Val Asp Trp Lys Thr His Asn Val Lys Phe Ile Lys Val Leu Asn
    290                 295                 300

Asp Lys Glu Lys Lys
305

<210> SEQ ID NO 47
<211> LENGTH: 310
<212> TYPE: PRT
<213> ORGANISM: Staphylococcus aureus

<400> SEQUENCE: 47

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Lys Ile Leu Asn Pro Asn Gly Tyr Trp Asn Ser Thr Leu Thr Trp
65                  70                  75                  80

Pro Gly Ser Tyr Ser Val Ser Ile Gln Asn Val Asp Asp Asn Asn
                85                  90                  95

Ser Thr Asn Val Thr Asp Phe Ala Pro Lys Asn Gln Asp Glu Ser Arg
            100                 105                 110

Glu Val Lys Tyr Thr Tyr Gly Tyr Lys Thr Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Ile
            290                 295                 300

Asn Asp Lys Glu Gln Lys
305                 310

<210> SEQ ID NO 48
<211> LENGTH: 309
<212> TYPE: PRT
<213> ORGANISM: Staphylococcus aureus

<400> SEQUENCE: 48

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Glu Lys Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 49
<211> LENGTH: 310
<212> TYPE: PRT

<213> ORGANISM: Staphylococcus aureus

<400> SEQUENCE: 49

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
                20                  25                  30

Lys Ile Ser Gln Ser Leu Gln Phe Asn Phe Leu Thr Glu Pro Asn Tyr
            35                  40                  45

Asp Lys Glu Thr Val Phe Ile Lys Ala Lys Gly Thr Ile Gly Ser Gly
        50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Ser Thr Asn Val Thr Asp Phe Ala Pro Lys Asn Gln Asp Glu Ser Arg
                100                 105                 110

Glu Val Lys Tyr Thr Tyr Gly Tyr Lys Thr Gly Gly Asp Phe Ser Ile
            115                 120                 125

Asn Arg Gly Gly Leu Thr Gly Asn Ile Thr Lys Glu Lys Asn Tyr Ser
130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
                180                 185                 190

Asp Arg Val Lys Ser Glu Ile Phe Ser Leu Thr Arg Asn Gly Asn Leu
            195                 200                 205

Trp Ala Lys Asp Asn Phe Thr Pro Lys Asn Lys Met Pro Val Thr Val
        210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
                260                 265                 270

Ser Gly Glu Asn His Val Asp Gln Lys Glu Lys Leu Ser Ala Leu
            275                 280                 285

Tyr Glu Val Asp Trp Lys Thr His Asp Val Lys Leu Ile Lys Thr Ile
290                 295                 300

Asn Asp Lys Glu Gln Lys
305                 310

<210> SEQ ID NO 50
<211> LENGTH: 309
<212> TYPE: PRT
<213> ORGANISM: Staphylococcus aureus

<400> SEQUENCE: 50

Lys Ile Asn Ser Glu Ile Lys Ala Val Ser Glu Lys Asn Leu Asp Gly
1               5                   10                  15

Asp Thr Lys Met Tyr Thr Arg Thr Ala Thr Thr Ser Asp Ser Gln Lys
                20                  25                  30

Asn Ile Thr Gln Ser Leu Gln Phe Asn Phe Leu Thr Glu Pro Asn Tyr
            35                  40                  45

Asp Lys Glu Thr Val Phe Ile Lys Ala Lys Gly Thr Ile Gly Ser Gly
     50                  55                  60

Leu Arg Ile Leu Asp Pro Asn Gly Tyr Trp Asn Ser Thr Leu Arg Trp
 65                  70                  75                  80

Pro Gly Ser Tyr Ser Val Ser Ile Gln Asn Val Asp Asn Asn
                 85                  90                  95

Thr Asn Val Thr Asp Phe Ala Pro Lys Asn Gln Asp Glu Ser Arg Glu
             100                 105                 110

Val Lys Tyr Thr Tyr Gly Tyr Lys Thr Gly Gly Asp Phe Ser Ile Asn
         115                 120                 125

Arg Gly Gly Leu Thr Gly Asn Ile Thr Lys Glu Ser Asn Tyr Ser Glu
130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                 165                 170                 175

Asn Met Gly His Asp His Thr Arg Gln Leu Thr Asn Asp Ser Asp Asn
             180                 185                 190

Arg Thr Lys Ser Glu Ile Phe Ser Leu Thr Arg Asn Gly Asn Leu Trp
         195                 200                 205

Ala Lys Asp Asn Phe Thr Pro Lys Asp Lys Met Pro Val Thr Val Ser
     210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                 245                 250                 255

Glu Phe Lys Ile Asp Trp Asn Arg His Gly Phe Trp Gly Tyr Trp Ser
             260                 265                 270

Gly Glu Asn His Val Asp Lys Lys Glu Glu Lys Leu Ser Ala Leu Tyr
         275                 280                 285

Glu Val Asp Trp Lys Thr His Asp Val Lys Phe Val Lys Val Leu Asn
     290                 295                 300

Asp Asn Glu Lys Lys
305

<210> SEQ ID NO 51
<211> LENGTH: 309
<212> TYPE: PRT
<213> ORGANISM: Staphylococcus aureus

<400> SEQUENCE: 51

Lys Ile Asn Ser Glu Ile Lys Ala Val Ser Glu Lys Asn Leu Asp Gly
 1               5                  10                  15

Asp Thr Lys Met Tyr Thr Arg Thr Ala Thr Thr Ser Asp Ser Gln Lys
             20                  25                  30

Asn Ile Thr Gln Ser Leu Gln Phe Asn Phe Leu Thr Glu Pro Asn Tyr
         35                  40                  45

Asp Lys Glu Thr Val Phe Ile Lys Ala Lys Gly Thr Ile Gly Ser Gly
     50                  55                  60

Leu Arg Ile Leu Asp Pro Asn Gly Tyr Trp Asn Ser Thr Leu Arg Trp
 65                  70                  75                  80

Pro Gly Ser Tyr Ser Val Ser Ile Gln Asn Val Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 52
<211> LENGTH: 309
<212> TYPE: PRT
<213> ORGANISM: Staphylococcus aureus

<400> SEQUENCE: 52

Lys Ile Asn Ser Glu Ile Lys Ala Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Pro Gly Asn Ile Thr Lys Glu Ser Asn Tyr Ser Glu
            130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
            195                 200                 205

Ala Lys Asp Asn Phe Thr Pro Lys Asn Lys Met Pro Val Thr Val Ser
            210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Lys Leu Ser Ala Leu Tyr
            275                 280                 285

Glu Val Asp Trp Lys Thr His Asp Val Lys Phe Val Lys Val Leu Asn
            290                 295                 300

Asp Asn Glu Lys Lys
305

<210> SEQ ID NO 53
<211> LENGTH: 309
<212> TYPE: PRT
<213> ORGANISM: Staphylococcus aureus

<400> SEQUENCE: 53

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

```
Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 54
<211> LENGTH: 309
<212> TYPE: PRT
<213> ORGANISM: Staphylococcus aureus

<400> SEQUENCE: 54

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220
```

```
Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 55
<211> LENGTH: 309
<212> TYPE: PRT
<213> ORGANISM: Staphylococcus aureus

<400> SEQUENCE: 55

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270
```

Gly Glu Asn His Val Asp Lys Lys Glu Glu Lys Leu Ser Ala Leu Tyr
275                 280                 285

Glu Val Asp Trp Lys Thr His Asn Val Lys Phe Val Lys Val Leu Asn
290                 295                 300

Asp Asn Glu Lys Lys
305

<210> SEQ ID NO 56
<211> LENGTH: 975
<212> TYPE: DNA
<213> ORGANISM: Staphylococcus aureus
<220> FEATURE:
<221> NAME/KEY: misc_feature
<222> LOCATION: (1)..(975)
<223> OTHER INFORMATION: E.coli codon optimized nucleotide sequence
      encoding the LukA polypeptide subunit from the Newman strain of S.
      aureus

<400> SEQUENCE: 56
catatggact cacaagacca gaacaaaaaa gaacacgtcg ataaatccca acaaaaagat      60
aaacgcaatg tcaccaataa agataaaaat agcaccgcac cggatgacat tggcaaaaac    120
ggtaaaatca ccaaacgtac cgaaacggtg tatgatgaaa aaacgaatat tctgcagaac    180
ctgcaatttg atttcatcga tgacccgacc tacgacaaaa atgtcctgct ggtgaaaaaa    240
cagggcagca ttcattctaa cctgaaattc gaaagtcaca agaagagaa aaactccaac    300 tggctgaaat atccgtcaga ataccatgtt gatttccagg tcaaacgtaa tcgcaaaacc    360
gaaattctgg accaactgcc gaaaacaaa atcagtaccg ccaaagtcga tagtacgttt    420
tcctatagct ctggcggtaa attcgactct accaaaggca tcggtcgtac gagttccaac    480
tcatactcga aaccatctc gtacaaccag caaaactacg atacgatcgc aagcggcaaa    540
aacaataact ggcatgtgca ctggtctgtt attgctaacg atctgaaata tggcggtgaa    600
gttaaaaatc gcaacgacga actgctgttt taccgtaata cccgcatcgc gacggttgaa    660
aacccggaac tgtcattcgc gtcgaaatat cgttacccgg ccctggtccg cagcggtttt    720
aatccggaat tcctgaccta cctgagcaac gaaaaatcta cgaaaaaac gcagttcgaa    780 gtgacctata cgcgtaatca agatattctg aaaaaccgcc cgggcattca ctacgcaccg    840
ccgatcctgg agaaaaacaa agatggtcag cgcctgatcg tcacctatga agtggattgg    900
aaaaacaaaa cggttaaagt ggttgacaaa tattccgatg acaacaaacc gtacaaagaa    960
ggttaatgac tcgag                                                    975

<210> SEQ ID NO 57
<211> LENGTH: 945
<212> TYPE: DNA
<213> ORGANISM: Staphylococcus aureus
<220> FEATURE:
<221> NAME/KEY: misc_feature
<222> LOCATION: (1)..(945)
<223> OTHER INFORMATION: E.coli codon optimized nucleotide sequence
      encoding the LukB polypeptide subunit from the Newman strain of S.
      aureus

<400> SEQUENCE: 57
catatgaaaa tcaactcaga aatcaaacaa gtctccgaaa aaacctgga tggcgacacc      60 aaaatgtata cccgcacggc gaccacgagc gactcgcaga aaaacatcac gcagagcctg    120
caatttaatt tcctgaccga accgaactac gataaagaaa cggtgttcat caaagcaaaa    180
ggcaccatcg gctcaggtct gcgtattctg gacccgaatg gctactggaa ctcgacccg    240

```
cgctggccgg gtagctattc tgtcagtatt cagaatgtgg atgacaacaa taacaccaac    300
gtgacggatt ttgctccgaa aaatcaagac gaaagtcgtg aagttaaata tacctacggc    360
tataaaacgg gcggtgattt ctctatcaat cgcggcggtc tgaccggtaa tattacgaaa    420
gaatcgaact atagcgaaac catctcctac cagcaaccgt catatcgtac cctgctggat    480
cagtccacgt cacataaagg cgtgggttgg aaagttgaag cgcacctgat caataacatg    540
ggccatgatc acacccgtca actgacgaat gatagcgaca accgcacgaa atctgaaatt    600
tttagtctga cccgcaatgg taacctgtgg gcgaaagata acttcacgcc gaaagacaaa    660
atgccggtca ccgtgtccga aggctttaat ccggaattcc tggccgtcat gtctcatgat    720
aaaaaagaca aaggtaaaag tcagtttgtg gttcactaca aacgttccat ggatgaattc    780
aaaatcgact ggaaccgcca tggcttctgg ggttactgga gcggtgaaaa ccacgttgat    840
aaaaaagaag aaaaactgtc tgcactgtat gaagttgact ggaaaaccca taacgtcaaa    900
ttcgttaaag tcctgaacga taacgagaaa aaataatgac tcgag                    945
```

<210> SEQ ID NO 58
<211> LENGTH: 308
<212> TYPE: PRT
<213> ORGANISM: Artificial Sequence
<220> FEATURE:
<223> OTHER INFORMATION: Synthetic HlgB-LukB fusion sequence
<220> FEATURE:
<221> NAME/KEY: MISC_FEATURE
<222> LOCATION: (1)..(29)
<223> OTHER INFORMATION: N terminus of HlgB swapped for N terminus of LukB
<220> FEATURE:
<221> NAME/KEY: MISC_FEATURE
<222> LOCATION: (30)..(308)
<223> OTHER INFORMATION: remainder C terminus of LukB

<400> SEQUENCE: 58

```
Ala Glu Gly Lys Ile Thr Pro Val Ser Val Lys Lys Val Asp Asp Lys
1               5                   10                  15

Val Thr Leu Tyr Lys Thr Thr Ala Thr Ala Asp Ser Asp Gln Lys Asn
            20                  25                  30

Ile Thr Gln Ser Leu Gln Phe Asn Phe Leu Thr Glu Pro Asn Tyr Asp
        35                  40                  45

Lys Glu Thr Val Phe Ile Lys Ala Lys Gly Thr Ile Gly Ser Gly Leu
    50                  55                  60

Arg Ile Leu Asp Pro Asn Gly Tyr Trp Asn Ser Thr Leu Arg Trp Pro
65                  70                  75                  80

Gly Ser Tyr Ser Val Ser Ile Gln Asn Val Asp Asp Asn Asn Asn Thr
                85                  90                  95

Asn Val Thr Asp Phe Ala Pro Lys Asn Gln Asp Glu Ser Arg Glu Val
            100                 105                 110

Lys Tyr Thr Tyr Gly Tyr Lys Thr Gly Gly Asp Phe Ser Ile Asn Arg
        115                 120                 125

Gly Gly Leu Thr Gly Asn Ile Thr Lys Glu Ser Asn Tyr Ser Glu Thr
    130                 135                 140

Ile Ser Tyr Gln Gln Pro Ser Tyr Arg Thr Leu Leu Asp Gln Ser Thr
145                 150                 155                 160

Ser His Lys Gly Val Gly Trp Lys Val Glu Ala His Leu Ile Asn Asn
                165                 170                 175
```

```
Met Gly His Asp His Thr Arg Gln Leu Thr Asn Asp Ser Asp Asn Arg
            180                 185                 190

Thr Lys Ser Glu Ile Phe Ser Leu Thr Arg Asn Gly Asn Leu Trp Ala
            195                 200                 205

Lys Asp Asn Phe Thr Pro Lys Asp Lys Met Pro Val Thr Val Ser Glu
            210                 215                 220

Gly Phe Asn Pro Glu Phe Leu Ala Val Met Ser His Asp Lys Lys Asp
225                 230                 235                 240

Lys Gly Lys Ser Gln Phe Val Val His Tyr Lys Arg Ser Met Asp Glu
            245                 250                 255

Phe Lys Ile Asp Trp Asn Arg His Gly Phe Trp Gly Tyr Trp Ser Gly
            260                 265                 270

Glu Asn His Val Asp Lys Lys Glu Lys Leu Ser Ala Leu Tyr Glu
            275                 280                 285

Val Asp Trp Lys Thr His Asn Val Lys Phe Val Lys Val Leu Asn Asp
            290                 295                 300

Asn Glu Lys Lys
305

<210> SEQ ID NO 59
<211> LENGTH: 913
<212> TYPE: DNA
<213> ORGANISM: Escherichia coli
<220> FEATURE:
<221> NAME/KEY: misc_feature
<222> LOCATION: (1)..(913)
<223> OTHER INFORMATION: sequence of the p15a origin used to construct
      P15a origin LukB pET24a(+)

<400> SEQUENCE: 59
gcgctagcgg agtgtatact ggcttactat gttggcactg atgagggtgt cagtgaagtg      60
cttcatgtgg caggagaaaa aaggctgcac cggtgcgtca gcagaatatg tgatacagga     120
tatattccgc ttcctcgctc actgactcgc tacgctcggt cgttcgactg cggcgagcgg     180
aaatggctta cgaacggggc ggagatttcc tggaagatgc caggaagata cttaacaggg     240
aagtgagagg gccgcggcaa agccgttttt ccataggctc cgccccctg acaagcatca      300 cgaaatctga cgctcaaatc agtggtggcg aaacccgaca ggactataaa gataccaggc     360
gtttccccct ggcggctccc tcgtgcgctc tcctgttcct gcctttcggt ttaccggtgt     420
cattccgctg ttatggccgc gtttgtctca ttccacgcct gacactcagt tccgggtagg     480
cagttcgctc caagctggac tgtatgcacg aaccccccgt tcagtccgac cgctgcgcct     540
tatccggtaa ctatcgtctt gagtccaacc cggaaagaca tgcaaaagca ccactggcag     600
cagccactgg taattgattt agaggagtta gtcttgaagt catgcgccgg ttaaggctaa     660
actgaaagga caagttttgg tgactgcgct cctccaagcc agttacctcg gttcaaagag     720
ttggtagctc agagaacctt cgaaaaaccg ccctgcaagg cggttttttc gttttcagag     780
caagagatta cgcgcagacc aaaacgatct caagaagatc atcttattaa tcagataaaa     840
tatttctaga tttcgtgca atttatctct tcaaatgtag cacctgaagt cagccccata      900
cgatataagt tgt                                                        913
```